(12) United States Patent
Wang et al.

(10) Patent No.: US 6,980,865 B1
(45) Date of Patent: Dec. 27, 2005

(54) IMPLANTABLE SHIELDED MEDICAL DEVICE

(75) Inventors: Xingwu Wang, Wellsville, NY (US);
Jeffrey L. Helfer, Webster, NY (US);
Howard J. Greenwald, Rochester, NY (US)

(73) Assignee: Nanoset, LLC, East Rochester, NY (US)

( * ) Notice: Subject to any disclaimer, the term of this patent is extended or adjusted under 35 U.S.C. 154(b) by 522 days.

(21) Appl. No.: 10/313,847

(22) Filed: Dec. 7, 2002

Related U.S. Application Data

(63) Continuation-in-part of application No. 10/054,407, filed on Jan. 22, 2002, now Pat. No. 6,506,972, and a continuation-in-part of application No. 10/090,553, filed on Mar. 4, 2002, now Pat. No. 6,930,242, and a continuation-in-part of application No. 10/229,183, filed on Aug. 26, 2002, now Pat. No. 6,876,886, and a continuation-in-part of application No. 10/242,969, filed on Sep. 13, 2002, now Pat. No. 6,844,492, and a continuation-in-part of application No. 10/260,247, filed on Sep. 30, 2002, now Pat. No. 6,673,999, and a continuation-in-part of application No. 10/273,738, filed on Oct. 18, 2002, now Pat. No. 6,906,256, and a continuation-in-part of application No. 10/303,264, filed on Nov. 25, 2002, now Pat. No. 6,713,671.

(51) Int. Cl.[7] .................................. A61N 1/05
(52) U.S. Cl. ................ 607/121; 607/116; 607/122; 174/36
(58) Field of Search .................. 607/116, 121, 122; 128/901; 174/36, 113 R, 102 SC, 102 P, 174/35 MS; 428/217, 218, 323, 402; 361/816, 361/818; 333/12

(56) References Cited

U.S. PATENT DOCUMENTS

| | | |
|---|---|---|
| 4,180,600 A | 12/1979 | Feldstein |
| 5,643,670 A | 7/1997 | Chung |
| 5,783,570 A | 7/1998 | Yokota et al. |
| 5,817,017 A | 10/1998 | Young et al. |
| 5,827,997 A | 10/1998 | Chung et al. |
| 5,938,979 A * | 8/1999 | Kambe et al. ............. 252/500 |
| 6,265,466 B1 | 7/2001 | Glatkowski et al. |

* cited by examiner

*Primary Examiner*—Kennedy Schaetzle
(74) *Attorney, Agent, or Firm*—Howard J. Greenwald

(57) ABSTRACT

An implantable device that contains a power source, a device for producing electrical signals, and a conductor assembly for communicating the electrical signals to biological matter. The conductor assembly contains of a conductor that is capable of being flexed at least about 15 degrees and that has a resistivity at 20 degrees Centigrade of from about 1 to about 100 micro ohm-centimeters. The conductor assembly also contains a magnetic shield located above the flexible conductor; the magnetic shield contains an antithrombogenic composition. The magnetic shield also contains a magnetic shielding material that has a magnetic shielding factor of at least about 0.5.

18 Claims, 39 Drawing Sheets

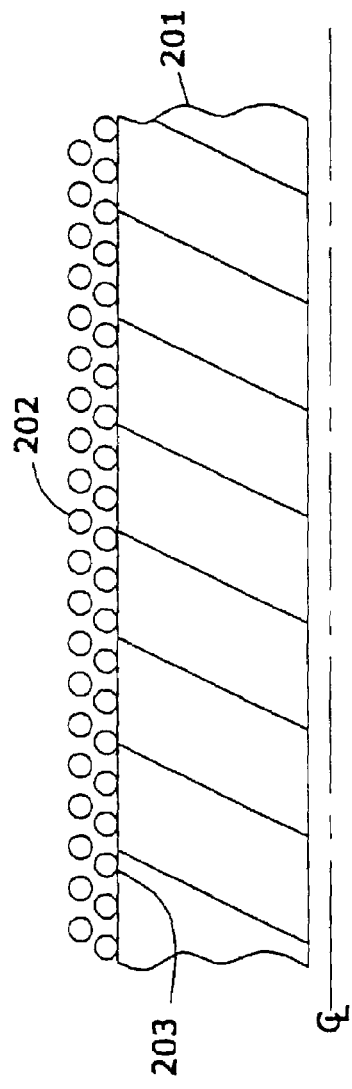
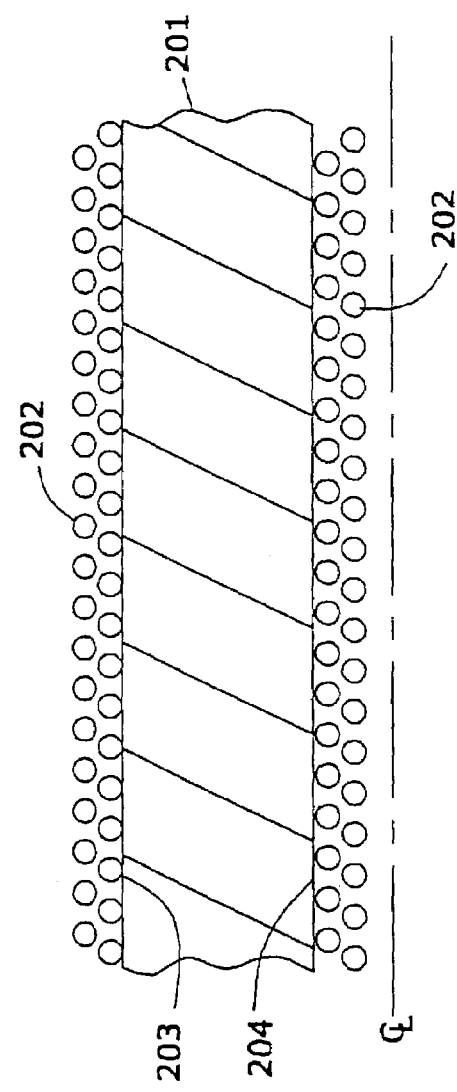
FIG.8A
FIG.8B

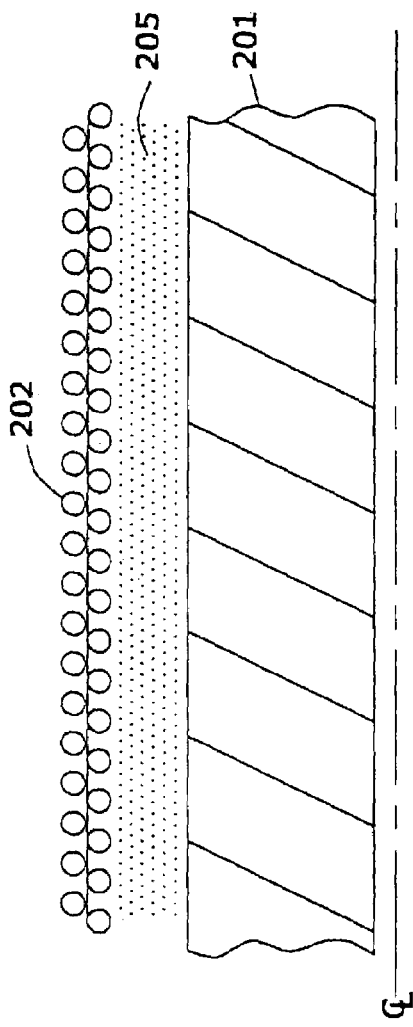
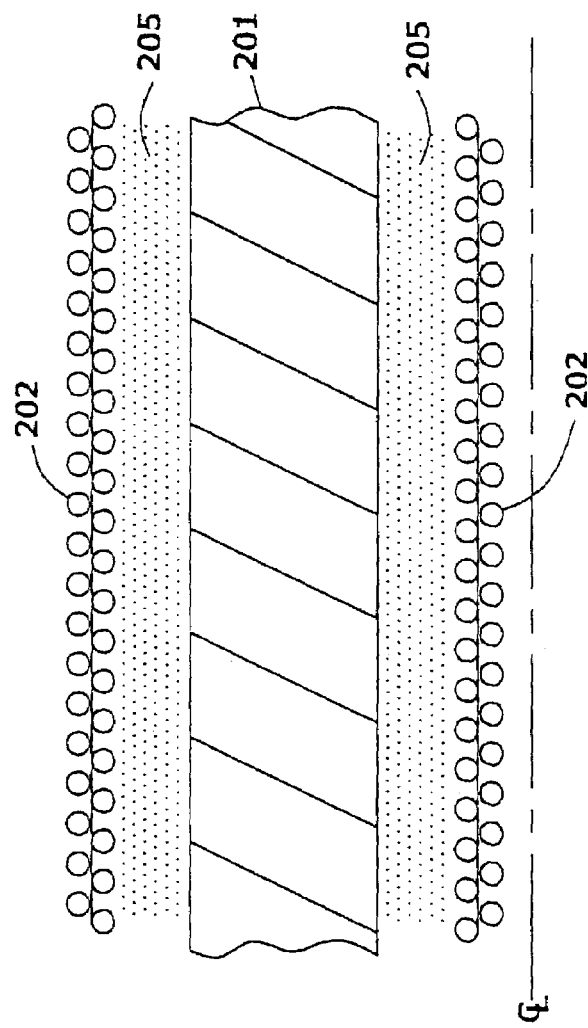

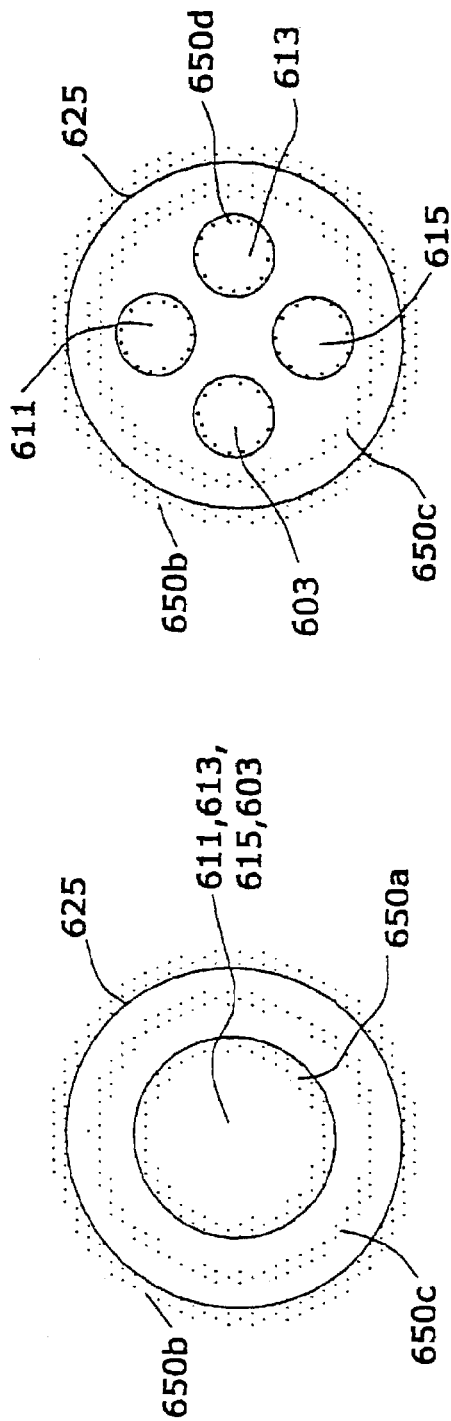
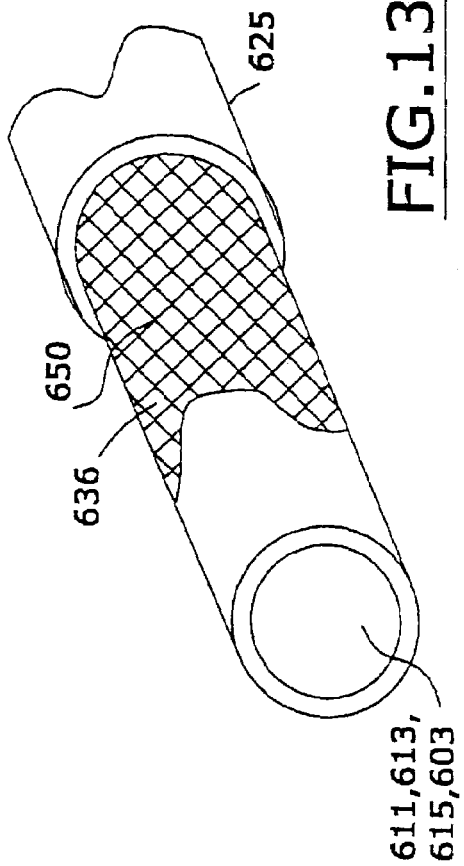
FIG.13B
FIG.13A
FIG.13C

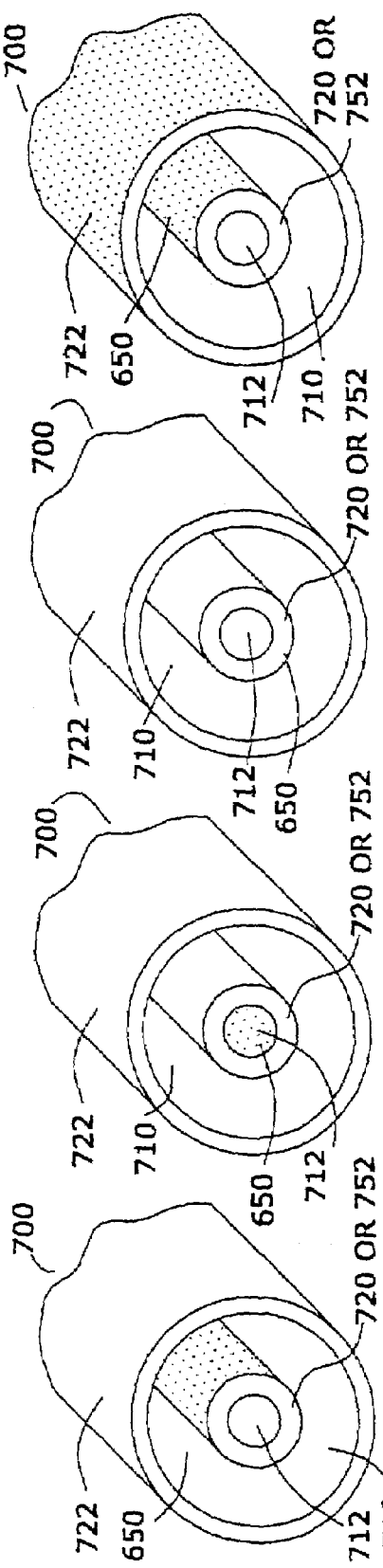

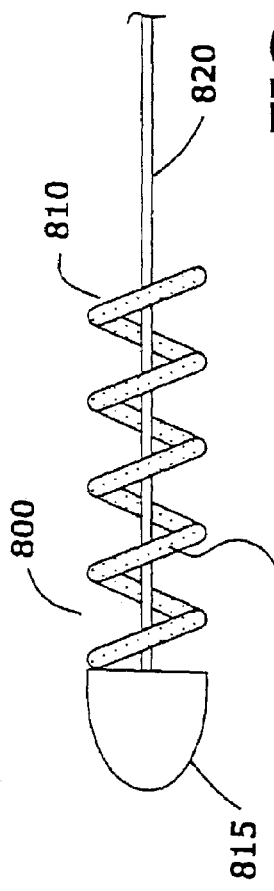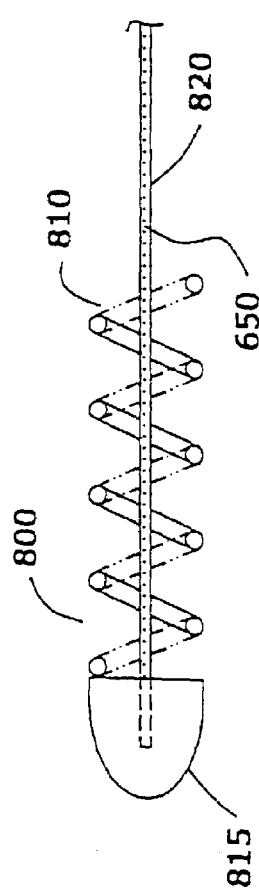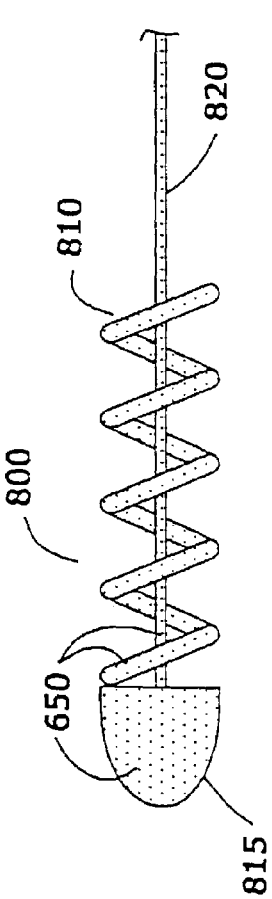

IMPLANTABLE SHIELDED MEDICAL DEVICE

REFERENCE TO RELATED PATENT APPLICATIONS

This application is a continuation-in-part of applicants' patent applications U.S. Ser. No. 10/054,407 (filed on Jan. 22, 2002), now U.S. Pat. No. 6,506,972, Ser. No. 10/090,553 (filed on Mar. 4, 2002), now U.S. Pat No. 6,930,242, Ser. No. 10/229,183 (filed on Aug. 26, 2002), now U.S. Pat. No. 6,876,886, Ser. No. 10/242,969 (filed on Sep. 13, 2002), now U.S. Pat. No. 6,844,492, Ser. No. 10/260,247 (filed on Sep. 30, 2002), now U.S. Pat. No. 6,673,999, Ser. No. 10/273,738 (filed on Oct. 18, 2002), now U.S. Pat. No. 6,906,256, and Ser. No. 10/303,264 (filed on Nov. 25, 2002), now U.S. Pat. No. 6,713,671.

FIELD OF THE INVENTION

A implantable device containing a pulse generator and a shielded conductor assembly, wherein the conductor assembly is comprised of an antithrombogenic composition.

BACKGROUND OF THE INVENTION

Many implanted medical devices that are powered by electrical energy have been developed. Some of these devices comprise a power source, one or more conductors, and a load. Others of these implantable medical device are passive, with no active energy source.

When a patient with one of these implanted devices is subjected to high intensity magnetic fields, on the order of at least about 1 Tesla, currents are often induced in the implanted conductors. The large current flows so induced often create substantial amounts of heat. Because living organisms can generally only survive within a relatively narrow range of temperatures, these large current flows are dangerous.

Furthermore, implantable devices, such as implantable pulse generators (IPGs) and cardioverter/defibrillator/pacemaker (CDPs), are sensitive to a variety of forms of electromagnetic interference (EMI). These devices include sensing and logic systems that respond to low-level signals from the heart. Because the sensing systems and conductive elements of these implantable devices are responsive to changes in local electromagnetic fields, they are vulnerable to external sources of severe electromagnetic noise, and in particular to electromagnetic fields emitted during magnetic resonance imaging (MRI) procedures. Therefore, patients with implantable devices are generally advised not to undergo magnetic resonance imaging (MRI) procedures, which often generate static magnetic fields of from between about 0.5 to about 10 Teslas and corresponding time-varying magnetic fields of about 20 megahertz to about 430 megahertz, as dictated by the Lamor frequency (see, e.g., page 1007 of Joseph D. Bronzino's "The Biomedical Engineering Handbook," CRC Press, Hartford, Conn., 1995). Typically, the strength of the magnetic component of such a time-varying magnetic field is about 1 to about 1,000 microTesla. In addition to the aforementioned static magnetic field and radio frequency magnetic fields, the use of MRI procedures also produces a magnetic gradient field, which allows for spatial resolution required by the MRI diagnosis.

One additional problem with conductors implanted within a living biological organism is that, when they are conducting electricity and are simultaneously subjected to large magnetic fields, a Lorentz force is created which often causes the conductor to move. This movement may damage body tissue.

Furthermore, the MRI procedures often induce a voltage within the living biological organism. This induced voltage is caused by the change of magnetic flux as a function of time. Thus, when the implanted conductor and the body tissue/fluid with which it is in electrical connection form a loop, this loop occupies an area within the body. The change of magnetic flux within such area induces a voltage which often is on the order of from about 0.1 to about 1.0 volts. As little as 0.4 volts is often sufficient to excite muscle (and other) cells and cause them to involuntarily move and/or react, a consequence which is often undesirable.

Several attempts have been made to provide effective shielding. Thus, e.g., in U.S. Pat. No. 6,265,466 an electromagnetic shielding composite having nanotubes is disclosed. This shield is adapted to shield relatively weak alternating electromagnetic fields with magnetic fields strengths of less than about 10 Gauss; but there is no disclosure that such shields would be effective against larger magnetic fields of at least about 0.5 Tesla.

It is an object of this invention to provide an implantable device which is at least partially shielded against strong magnetic fields.

SUMMARY OF THE INVENTION

In accordance with this invention, there is provided an implantable device comprised of a power source, means for generating electrical signals, means for communicating said electrical signals with biological matter in a biological organism, and a conductor assembly electrically connected to said biological matter. The conductor assembly is comprised of a conductor that is capable of being flexed at least about 15 degrees and that has a resistivity at 20 degrees Centigrade of from about 1 to about 100 micro ohm-centimeters. The conductor assembly is comprised of a magnetic shield disposed above said flexible conductor, wherein said magnetic shield is comprised of an antithrombogenic composition, wherein said magnetic shield is comprised of a layer of magnetic shielding material, and wherein said layer of magnetic shielding material, when exposed to a magnetic field with an intensity of at least about 0.5 Teslas, has a magnetic shielding factor of at least about 0.5. The conductor (c) said conductor assembly has a heat shielding factor of at least about 0.2 when tested in accordance with A.S.T.M. Standard Test F-2182-02.

BRIEF DESCRIPTION OF THE DRAWINGS

The invention will be described by reference to the following drawings, in which like numerals refer to like elements, and in which:

FIGS. 8A, 8B, 8C, and 8D are schematic sectional views of a substrate, such as one of the specific medical devices described in this application, coated with nanomagnetic particulate matter on its exterior surface;

FIGS. 13A, 13B, and 13C are schematic views of an implantable catheter coated with nanomagnetic particulate material;

FIGS. 14A through 14G are schematic views of an implantable, steerable catheter coated with nanomagnetic particulate material;

FIGS. 15A, 15B and 15C are schematic views of an implantable guide wire coated with nanomagnetic particulate material;

DESCRIPTION OF THE PREFERRED EMBODIMENTS

Figure 1:
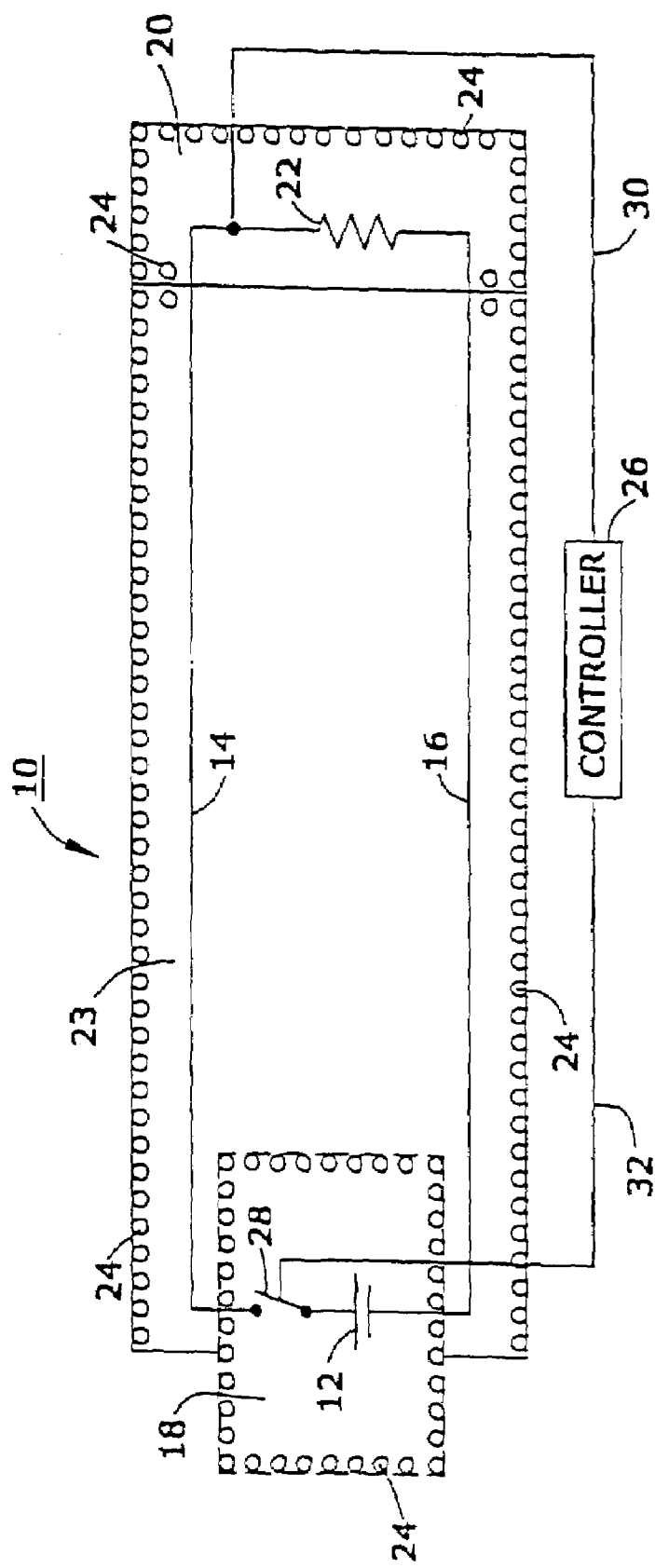
FIG. 1 is a schematic sectional view of a shielded implanted device comprised of one preferred conductor assembly of the invention.

FIG. 1 is a schematic sectional view of one preferred device 10 that, in one embodiment, is implanted in a living biological organism. Referring to FIG. 1, it will be seen that device 10 is comprised of a power source 12, a first conductor 14, a second conductor 16, a first insulative shield 18 disposed about power source 12, a second insulative shield 20 disposed about a load 22, a third insulative shield 23 disposed about a first conductor 14, and a second conductor 16, and a multiplicity of nanomagentic particles 24 disposed on said first insulative shield, said second insulative shield, and said third insulative shield.

In one embodiment, the device 10 is a an implantable device used to monitor and maintain at least one physiologic function, which is capable of operating in the presence of damaging electromagnetic interference; see, e.g., United States published patent application U.S. 20020038135, the entire disclosure of which is hereby incorporated by reference into this specification.

In one aspect of this embodiment, the device 10 is an implantable pacemaker. These pacemakers are well known to those skilled in the art. Reference may be had, e.g., to U.S. Pat. Nos. 5,697,959, 5,697,956 (implantable stimulation device having means for optimizing current drawin), U.S. Pat. No. 5,456,692 (method for nonivasively altering the function of an implanted pacemaker), U.S. Pat. No. 5,431, 691 (system for recording and displaying a sequential series of pacing events), U.S. Pat. No. 5,984,005 (multi-event bin heart rate histogram for use with an implantable pacemaker), U.S. Pat. Nos. 5,176,138, 5,003,975, 6,324,427, 5,788,717, 5,417,718, 5,228,438, and the like. The entire disclosure of each of these United States patents is hereby incorporated by reference into this specification.

In the embodiment depicted in FIG. 1, and referring again to FIG. 1, the power source 12 is a battery 12 that is operatively connected to a controller 26. In the embodiment depicted, controller 26 is operatively connected to the load 22 and the switch 28. Depending upon the information furnished to controller 26, it may deliver no current, direct current, and/or current pulses to the load 22.

In one embodiment, not shown, some or all of the controller 26 and/or the wires 30 and 32 are shielded from magnetic radiation. In another embodiment, not shown, one or more connections between the controller 26 and the switch 28 and/or the load 22 are made by wireless means such as, e.g., telemetry means.

In one embodiment, not shown, the power source 12 provides a source of alternating current. In another embodiment, the power source 12 in conjunction with the controller 26 provides pulsed direct current.

The load 22 may be any of the implanted devices known to those skilled in the art. Thus, e.g., as described hereinabove, the load 22 may be a pacemaker. Thus, e.g., load 22 may be an artificial heart. Thus, e.g., load 22 may be a heart-massaging device. Thus, e.g., load 22 may be a defibrillator.

The conductors 14 and 16 may be any conductive material(s) that have a resistivity at 20 degrees Centigrade of from about 1 to about 100 microohm-centimeters. Thus, e.g., the conductive material(s) may be silver, copper, aluminum, alloys thereof, mixtures thereof, and the like.

In one embodiment, the conductors 14 and 16 consist essentially of such conductive material. Thus, e.g., it is preferred not to use, e.g., copper wire coated with enamel. The use of such typical enamel coating on the conductor does not work well in the instant invention.

In the first step of one embodiment of the process of this invention, step 40, the conductive wires 14 and 16 are coated with electrically insulative material. Suitable insulative materials include nano-sized silicon dioxide, aluminum oxide, cerium oxide, yttrium-stabilized zirconia, silicon carbide, silicon nitride, aluminum nitride, and the like. In general, these nano-sized particles will have a particle size distribution such that at least about 90 weight percent of the particles have a maximum dimension in the range of from about 10 to about 100 nanometers.

The coated conductors 14 and 16 may be prepared by conventional means such as, e.g., the process described in U.S. Pat. No. 5,540,959, the entire disclosure of which is hereby incorporated by reference into this specification. This patent describes and claims a process for preparing a coated substrate, comprising the steps of: (a) creating mist particles from a liquid, wherein: 1. said liquid is selected from the group consisting of a solution, a slurry, and mixtures thereof, 2. said liquid is comprised of solvent and from 0.1 to 75 grams of solid material per liter of solvent, 3. at least 95 volume percent of said mist particles have a maximum dimension less than 100 microns, and 4. said mist particles are created from said first liquid at a rate of from 0.1 to 30 milliliters of liquid per minute; (b) contacting said mist particles with a carrier gas at a pressure of from 761 to 810 millimeters of mercury; (c) thereafter contacting said mist particles with alternating current radio frequency energy with a frequency of at least 1 megahertz and a power of at least 3 kilowatts while heating said mist particles to a temperature of at least about 100 degrees centigrade, thereby producing a heated vapor; (d) depositing said heated vapor onto a substrate, thereby producing a coated substrate; and (e) subjecting said coated substrate to a temperature of from about 450 to about 1,400 degrees centigrade for at least about 10 minutes.

By way of further illustration, one may coat conductors 14 and 16 by means of the processes disclosed in a text by D. Satas on "Coatings Technology Handbook" (Marcel Dekker, Inc., New York, N.Y., 1991). As is disclosed in such text, one may use cathodic arc plasma deposition (see pages 229 et seq.), chemical vapor deposition (see pages 257 et seq.), sol-gel coatings (see pages 655 et seq.), and the like. One may also use one or more of the processes disclosed in this book for preparing other coated members such as, e.g., sheath 4034 (see FIGS. 35 and 36).

Figure 2:
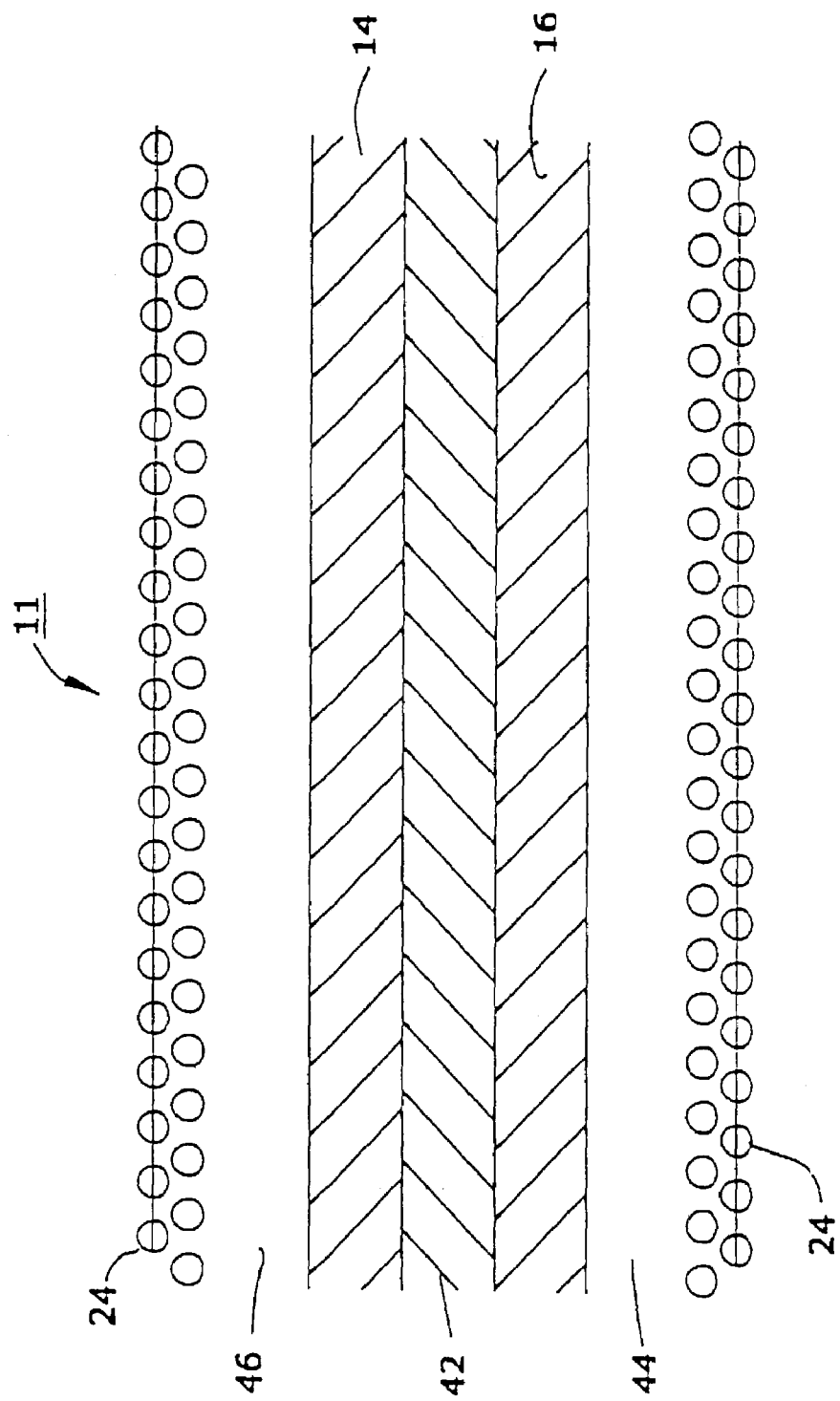
FIG. 2 is an enlarged sectional view of a portion of the conductor assembly of FIG. 1.
Figure 3:
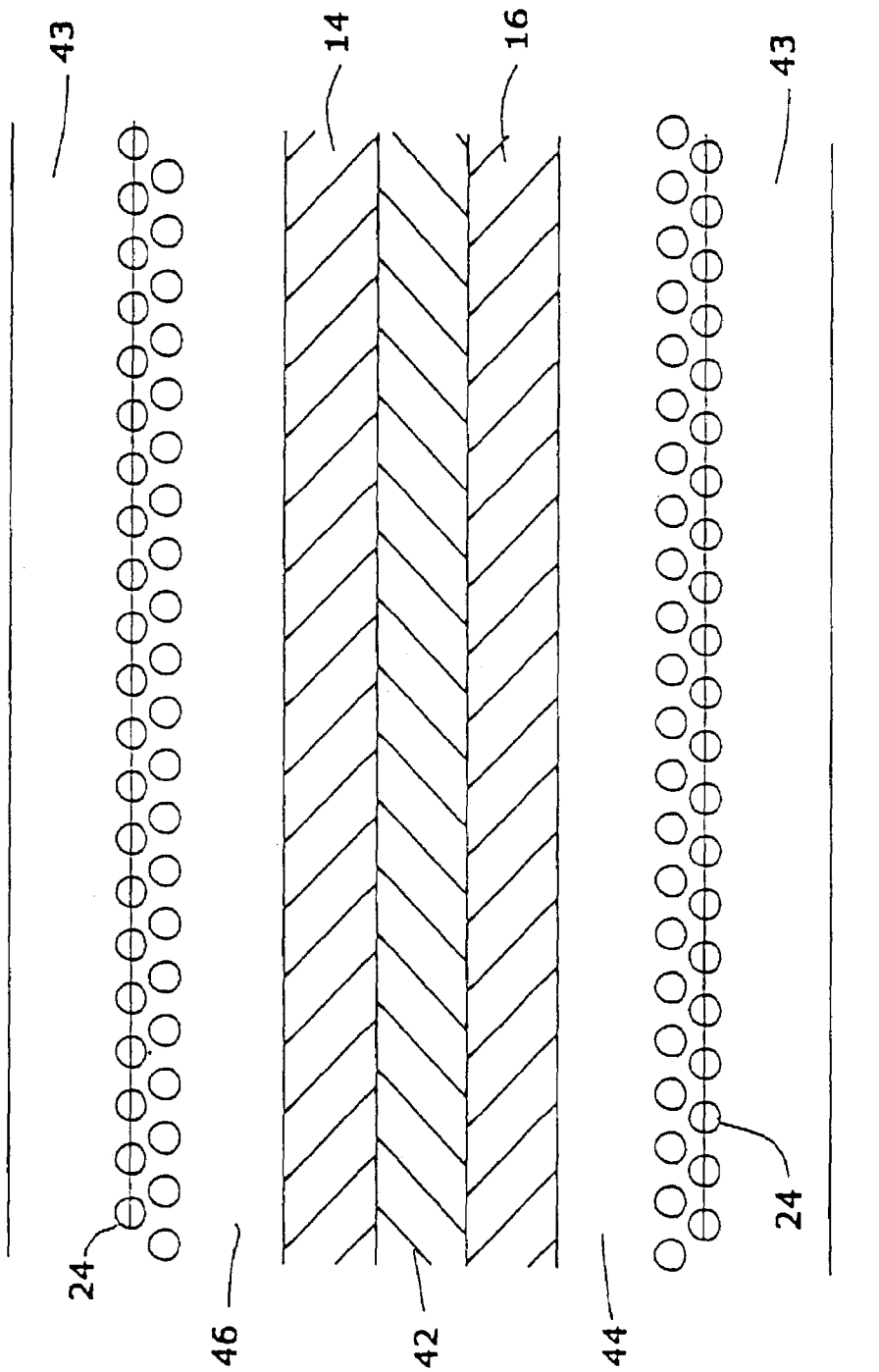
FIG. 3 is a sectional view of another conductor assembly of this invention.
Figure 4:
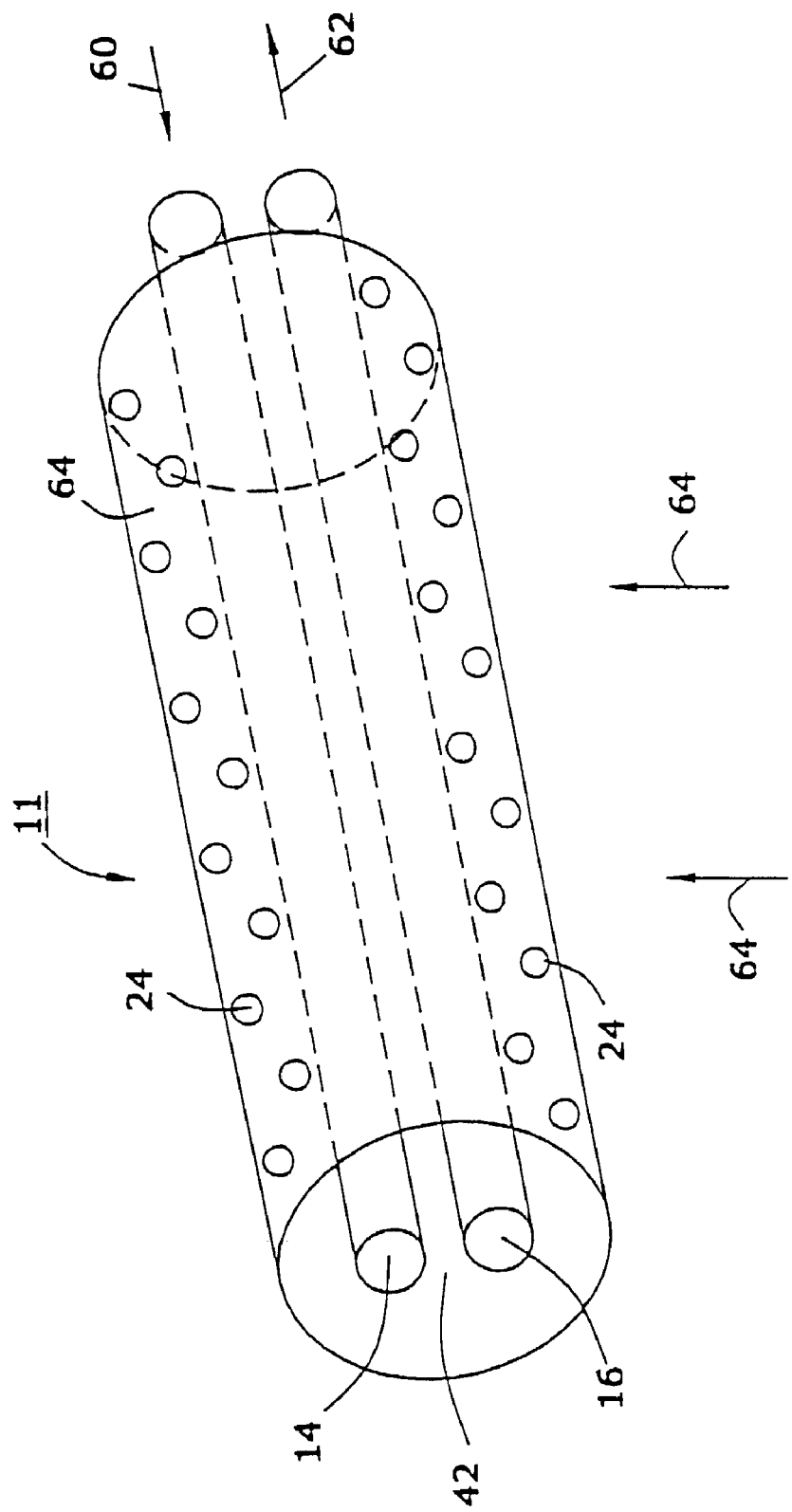
FIG. 4 is a schematic view of the conductor assembly of FIG. 2.

FIG. 2 is a sectional view of the coated conductors 14/16 of the device of FIG. 1. Referring to FIG. 2, and in the preferred embodiment depicted therein, it will be seen that conductors 14 and 16 are separated by insulating material 42. In order to obtain the structure depicted in FIG. 2, one may simultaneously coat conductors 14 and 16 with the insulating material so that such insulators both coat the conductors 14 and 16 and fill in the distance between them with insulation.

The insulating material 42 that is disposed between conductors 14/16, may be the same as the insulating material 44/46 that is disposed above conductor 14 and below conductor 16. Alternatively, and as dictated by the choice of processing steps and materials, the insulating material 42 may be different from the insulating material 44 and/or the insulating material 46. Thus, step 48 of the process describes disposing insulating material between the coated conductors 14 and 16. This step may be done simultaneously with step 40; and it may be done thereafter.

The insulating material 42, the insulating material 44, and the insulating material 46 each generally has a resistivity of from about 1,000,000,000 to about 10,000,000,000,000 ohm-centimeters.

After the insulating material 42/44/46 has been deposited, and in one embodiment, the coated conductor assembly is preferably heat treated in step 50. This heat treatment often is used in conjunction with coating processes in which the heat is required to bond the insulative material to the conductors 14/16.

The heat-treatment step may be conducted after the deposition of the insulating material 42/44/46, or it may be conducted simultaneously therewith. In either event, and when it is used, it is preferred to heat the coated conductors 14/16 to a temperature of from about 200 to about 600 degrees Centigrade for from about 1 minute to about 10 minutes.

Figure 1A:
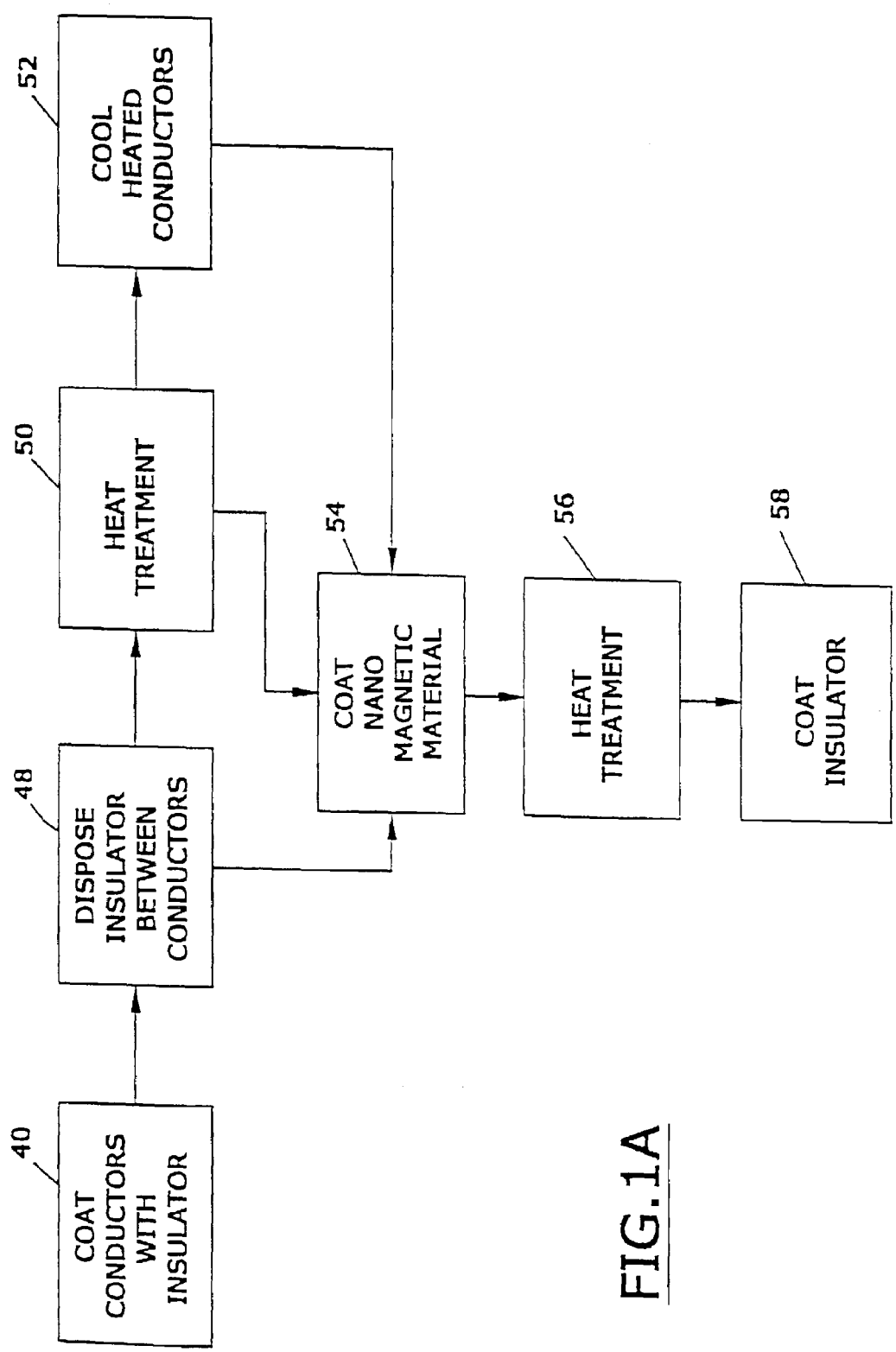
FIG. 1A is a flow diagram of a preferred process of the invention.

Referring again to FIG. 1A, and in step 52 of the process, after the coated conductors 14/16 have been subjected to heat treatment step 50, they are allowed to cool to a temperature of from about 30 to about 100 degrees Centigrade over a period of time of from about 3 to about 15 minutes.

One need not invariably heat treat and/or cool. Thus, referring to FIG. 1A, one may immediately coat nanomagnetic particles onto to the coated conductors 14/16 in step 54 either after step 48 and/or after step 50 and/or after step 52.

In step 54, nanomagnetic materials are coated onto the previously coated conductors 14 and 16. This is best shown in FIG. 2, wherein the nanomagnetic particles are identified as particles 24.

In general, and as is known to those skilled in the art, nanomagnetic material is magnetic material which has an average particle size less than 100 nanometers and, preferably, in the range of from about 2 to 50 nanometers. Reference may be had, e.g., to U.S. Pat. No. 5,889,091 (rotationally free nanomagnetic material), U.S. Pat. Nos. 5,714,136, 5,667,924, and the like. The entire disclosure of each of these United States patents is hereby incorporated by reference into this specification.

The nanomagnetic materials may be, e.g., nano-sized ferrites such as, e.g., the nanomagnetic ferrites disclosed in U.S. Pat. No. 5,213,851, the entire disclosure of which is hereby incorporated by reference into this specification. This patent claims a process for coating a layer of ferritic material with a thickness of from about 0.1 to about 500 microns onto a substrate at a deposition rate of from about 0.01 to about 10 microns per minute per 35 square centimeters of substrate surface, comprising the steps of: (a) providing a solution comprised of a first compound and a second compound, wherein said first compound is an iron compound and said second compound is selected from the group consisting of compounds of nickel, zinc, magnesium, strontium, barium, manganese, lithium, lanthanum, yttrium, scandium, samarium, europium, terbium, dysprosium, holmium, erbium, ytterbium, lutetium, cerium, praseodymium, thulium, neodymium, gadolinium, aluminum, iridium, lead, chromium, gallium, indium, chromium, samarium, cobalt, titanium, and mixtures thereof, and wherein said solution is comprised of from about 0.01 to about 1,000 grams of a mixture consisting essentially of said compounds per liter of said solution; (b) subjecting said solution to ultrasonic sound waves at a frequency in excess of 20,000 hertz, and to an atmospheric pressure of at least about 600 millimeters of mercury, thereby causing said solution to form into an aerosol; (c) providing a radio frequency plasma reactor comprised of a top section, a bottom section, and a radio-frequency coil; (d) generating a hot plasma gas within said radio frequency plasma reactor, thereby producing a plasma region; (e) providing a flame region disposed above said top section of said radio frequency plasma reactor; (f) contacting said aerosol with said hot plasma gas within said plasma reactor while subjecting said aerosol to an atmospheric pressure of at least about 600 millimeters of mercury and to a radio frequency alternating current at a frequency of from about 100 kilohertz to about 30 megahertz, thereby forming a vapor; (g) providing a substrate disposed above said flame region; and (h) contacting said vapor with said substrate, thereby forming said layer of ferritic material.

By way of further illustration, one may use the techniques described in an article by M. De Marco, X. W. Wang, et al. on "Mossbauer and magnetization studies of nickel ferrites" published in the Journal of Applied Physics 73 (10), May 15, 1993, at pages 6287–6289.

In general, the thickness of the layer of nanomagnetic material deposited onto the coated conductors 14/16 is less than about 5 microns and generally from about 0.1 to about 3 microns.

After the nanomagnetic material is coated in step 54, the coated assembly may be optionally heat-treated in step 56. In this optional step 56, it is preferred to subject the coated conductors 14/16 to a temperature of from about 200 to about 600 degrees Centigrade for from about 1 to about 10 minutes.

In one embodiment, illustrated in FIG. 3, one or more additional insulating layers 43 are coated onto the assembly depicted in FIG. 2, by one or more of the processes disclosed hereinabove. This is conducted in optional step 58 (see FIG. 1A).

FIG. 4 is a partial schematic view of the assembly 11 of FIG. 2, illustrating the current flow in such assembly. Referring go FIG. 4, it will be seen that current flows into conductor 14 in the direction of arrow 60, and it flows out of conductor 16 in the direction of arrow 62. The net current flow through the assembly 11 is zero; and the net Lorentz force in the assembly 11 is thus zero. Consequently, even high current flows in the assembly 11 do not cause such assembly to move.

In the embodiment depicted in FIG. 4, conductors 14 and 16 are substantially parallel to each other. As will be apparent, without such parallel orientation, there may be some net current and some net Lorentz effect.

In the embodiment depicted in FIG. 4, and in one preferred aspect thereof, the conductors 14 and 16 preferably have the same diameters and/or the same compositions and/or the same length.

Referring again to FIG. 4, the nanomagnetic particles 24 are present in a density sufficient so as to provide shielding from magnetic flux lines 64. Without wishing to be bound to any particular theory, applicant believes that the nanomagnetic particles 24 trap and pin the magnetic lines of flux 64.

In order to function optimally, the nanomagnetic particles 24 have a specified magnetization. As is known to those skilled in the art, magnetization is the magnetic moment per unit volume of a substance. Reference may be had, e.g., to U.S. Pat. Nos. 4,169,998, 4,168,481, 4,166,263, 5,260,132, 4,778,714, and the like. The entire disclosure of each of these United States patents is hereby incorporated by reference into this specification.

Referring again to FIG. 4, the layer of nanomagnetic particles 24 preferably has a saturation magnetization, at 25 degrees Centigrade, of from about 1 to about 36,000 Gauss, or higher. In one embodiment, the saturation magnetization at room temperature of the nanomagentic particles is from about 500 to about 10,000 Gauss. For a discussion of the saturation magnetization of various materials, reference may be had, e.g., to U.S. Pat. Nos. 4,705,613, 4,631,613, 5,543, 070, 3,901,741 (cobalt, samarium, and gadolinium alloys), and the like. The entire disclosure of each of these United States patents is hereby incorporated by reference into this specification. As will be apparent to those skilled in the art, especially upon studying the aforementioned patents, the saturation magnetization of thin films is often higher than the saturation magnetization of bulk objects.

In one embodiment, it is preferred to utilize a thin film with a thickness of less than about 2 microns and a saturation magnetization in excess of 20,000 Gauss. The thickness of the layer of nanomagentic material is measured from the bottom surface of the layer that contains such material to the top surface of such layer that contains such material; and such bottom surface and/or such top surface may be contiguous with other layers of material (such as insulating material) that do not contain nanomagnetic particles.

Thus, e.g., one may make a thin film in accordance with the procedure described at page 156 of Nature, Volume 407, Sep. 14, 2000, that describes a multilayer thin film has a saturation magnetization of 24,000 Gauss.

By the appropriate selection of nanomagnetic particles, and the thickness of the films deposited, one may obtain saturation magnetizations of as high as at least about 36,000.

In the preferred embodiment depicted in FIG. 4, the nanomagnetic particles 24 are disposed within an insulating matrix so that any heat produced by such particles will be slowly dispersed within such matrix. Such matrix, as indicated hereinabove, may be made from ceria, calcium oxide, silica, alumina. In general, the insulating material 42 preferably has a thermal conductivity of less than about 20 (caloriescentimeters/square centimeters–degree second) ×10,000. See, e.g., page E-6 of the $63^{rd}$ Edition of the "Handbook of Chemistry and Physics" (CRC Press, Inc., Boca Raton, Fla., 1982).

The nanomagnetic materials 24 typically comprise one or more of iron, cobalt, nickel, gadolinium, and samarium atoms. Thus, e.g., typical nanomagnetic materials include alloys of iron and nickel (permalloy), cobalt, niobium, and zirconium (CNZ), iron, boron, and nitrogen, cobalt, iron, boron, and silica, iron, cobalt, boron, and fluoride, and the like. These and other materials are descried in a book by J. Douglas Adam et al. entitled "Handbook of Thin Film Devices" (Academic Press, San Diego, Calif., 2000). Chapter 5 of this book beginning at page 185, describes "magnetic films for planar inductive components and devices;" and Tables 5.1 and 5.2 in this chapter describe many magnetic materials.

Figure 5:
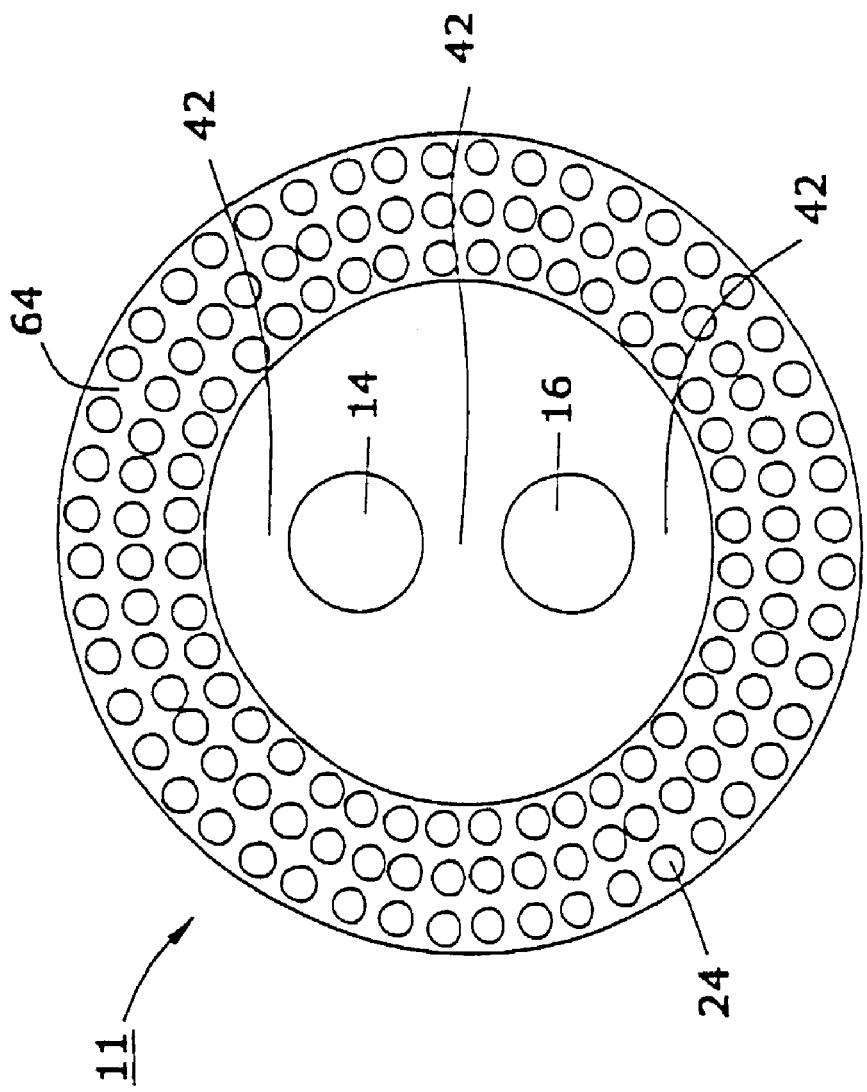
FIG. 5 is a sectional view of the conductor assembly of FIG. 2.

FIG. 5 is a sectional view of the assembly 11 of FIG. 2. The device of FIG. 5, and of the other Figures of this application, is preferably substantially flexible. As used in this specification, the term flexible refers to an assembly that can be bent to form a circle with a radius of less than 2 centimeters without breaking. Put another way, the bend radius of the coated assembly 11 can be less than 2 centimeters. Reference may be had, e.g., to U.S. Pat. Nos. 4,705,353, 5,946,439, 5,315,365, 4,641,917, 5,913,005, and the like. The entire disclosure of each of these United States patents is hereby incorporated by reference into this specification.

In another embodiment, not shown, the shield is not flexible. Thus, in one aspect of this embodiment, the shield is a rigid, removable sheath that can be placed over an endoscope or a biopsy probe used inter-operatively with magnetic resonance imaging.

As will be apparent, even when the magnetic insulating properties of the assembly of this invention are not 100 percent effective, the assembly still prevents the rapid dissipation of heat to bodily tissue.

In another embodiment of the invention, there is provided a magnetically shielded conductor assembly comprised of a conductor and a film of nanomagnetic material disposed above said conductor. In this embodiment, the conductor has a resistivity at 20 degrees Centigrade of from about 1 to about 2,000 micro ohm-centimeters and is comprised of a first surface exposed to electromagnetic radiation. In this embodiment, the film of nanomagnetic material has a thickness of from about 100 nanometers to about 10 micrometers and a mass density of at least about about 1 gram per cubic centimeter, wherein the film of nanomagnetic material is disposed above at least about 50 percent of said first surface exposed to electromagnetic radiation, and the film of nanomagnetic material has a saturation magnetization of from about 1 to about 36,000 Gauss, a coercive force of from about 0.01 to about 5,000 Oersteds, a relative magnetic permeability of from about 1 to about 500,000, and a magnetic shielding factor of at least about 0.5. In this embodiment, the nanomagnetic material has an average particle size of less than about 100 nanometers.

Figure 6:
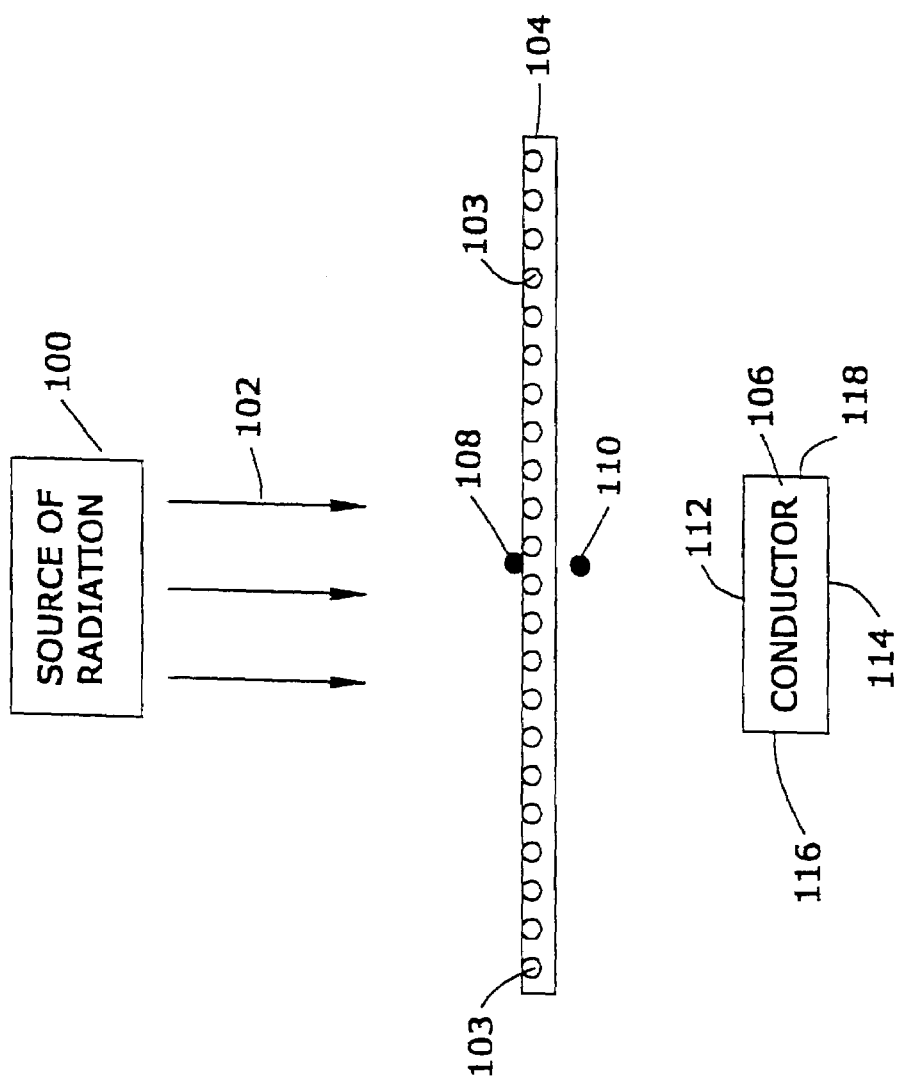
FIG. 6 is a schematic of another preferred shielded conductor assembly.

In the preferred embodiment of this invention, a film of nanomagnetic is disposed above at least one surface of a conductor. Referring to FIG. 6, and in the schematic diagram depicted therein, a source of electromagnetic radiation 100 emits radiation 102 in the direction of film 104. Film 104 is disposed above conductor 106, i.e., it is disposed between conductor 106 of the electromagnetic radiation 102.

The film 104 is adapted to reduce the magnetic field strength at point 108 (which is disposed less than 1 centimeter above film 104) by at least about 50 percent. Thus, if one were to measure the magnetic field strength at point 108, and thereafter measure the magnetic field strength at point 110 (which is disposed less than 1 centimeter below film 104), the latter magnetic field strength would be no more than about 50 percent of the former magnetic field strength. Put another way, the film 104 has a magnetic shielding factor of at least about 0.5.

In one embodiment, the film 104 has a magnetic shielding factor of at least about 0.9, i.e., the magnetic field strength at point 110 is no greater than about 10 percent of the magnetic field strength at point 108. Thus, e.g., the static magnetic field strength at point 108 can be, e.g., one Tesla, whereas the static magnetic field strength at point 110 can be, e.g., 0.1 Tesla. Furthermore, the time-varying magnetic field strength of a 100 milliTesla would be reduced to about 10 milliTesla of the time-varying field.

Referring again to FIG. 6, the nanomagnetic material 103 in film 104 has a saturation magnetization of form about 1 to about 36,000 Gauss. This property has been discussed elsewhere in this specification. In one embodiment, the nanomagnetic material 103 a saturation magnetization of from about 200 to about 26,000 Gauss.

The nanomagnetic material 103 in film 104 also has a coercive force of from about 0.01 to about 5,000 Oersteds. The term coercive force refers to the magnetic field, H, which must be applied to a magnetic material in a symmetrical, cyclicly magnetized fashion, to make the magnetic induction, B, vanish; this term often is referred to as magnetic coercive force. Reference may be had, e.g., to U.S. Pat. Nos. 4,061,824, 6,257,512, 5,967,223, 4,939,610, 4,741,953, and the like. The entire disclosure of each of these United States patents is hereby incorporated by reference into this specification.

In one embodiment, the nanomagnetic material 103 has a coercive force of from about 0.01 to about 3,000 Oersteds. In yet another embodiment, the nanomagnetic material 103 has a coercive force of from about 0.1 to about 10.

Referring again to FIG. 6, the nanomagnetic material 103 in film 104 preferably has a relative magnetic permeability of from about 1 to about 500,000; in one embodiment, such material 103 has a relative magnetic permeability of from about 1.5 to about 260,000. As used in this specification, the term relative magnetic permeability is equal to B/H, and is also equal to the slope of a section of the magnetization curve of the film. Reference may be had, e.g., to page 4–28 of E. U. Condon et al.'s "Handbook of Physics" (McGraw-Hill Book Company, Inc., New York, 1958).

Reference also may be had to page 1399 of Sybil P. Parker's "McGraw-Hill Dictionrary of Scientific and Technical Terms," Fourth Edition (McGraw Hill Book Company, New York, 1989). As is disclosed on this page 1399, permeability is " . . . a factor, characteristic of a material, that is proportional to the magnetic induction produced in a material divided by the magnetic field strength; it is a tensor when these quantities are not parallel.

Reference also may be had, e.g., to U.S. Pat. Nos. 6,181,232, 5,581,224, 5,506,559, 4,246,586, 6,390,443, and the like. The entire disclosure of each of these United States patents is hereby incorporated by reference into this specification.

In one embodiment, the nanomagnetic material 103 in film 104 has a relative magnetic permeability of from about 1.5 to about 2,000.

Referring again to FIG. 6, the nanomagnetic material 103 in film 104 preferably has a mass density of at least about 0.001 grams per cubic centimeter; in one embodiment, such mass density is at least about 1 gram per cubic centimeter. As used in this specification, the term mass density refers to the mass of a give substance per unit volume. See, e.g., page 510 of the aforementioned "McGraw-Hill Dictionary of Scientific and Technical Terms." In one embodiment, the film 104 has a mass density of at least about 3 grams per cubic centimeter. In another embodiment, the nanomagnetic material 103 has a mass density of at least about 4 grams per cubic centimeter.

In the embodiment depicted in FIG. 6, the film 104 is disposed above 100 percent of the surfaces 112, 114, 116, and 118 of the conductor 106. In the embodiment depicted in FIG. 2, by comparison, the nanomagnetic film is disposed around the conductor.

Figure 7:
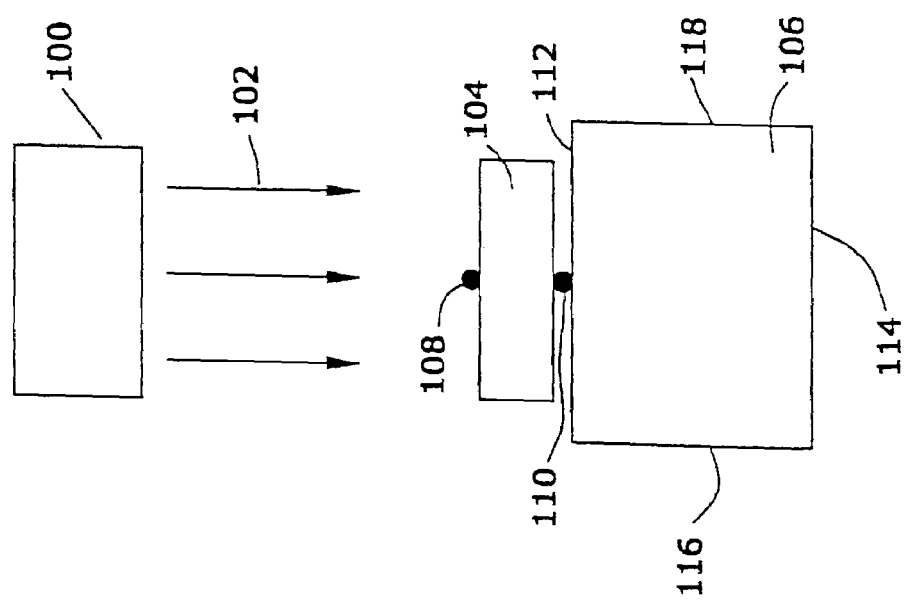
FIG. 7 is a schematic of yet another configuration of a shielded conductor assembly.

Yet another embodiment is depicted in FIG. 7. In the embodiment depicted in FIG. 7, the film 104 is not disposed in front of either surface 114, or 116, or 118 of the conductor 106. Inasmuch as radiation is not directed towards these surfaces, this is possible.

What is essential, however, is that the film 104 be interposed between the radiation 102 and surface 112. It is preferred that film 104 be disposed above at least about 50 percent of surface 112. In one embodiment, film 104 is disposed above at least about 90 percent of surface 112.

In the remainder of this specification, the use of film 104 with various medical devices will be discussed.

Many implanted medical devices have been developed to help medical practitioners treat a variety of medical conditions by introducing an implantable medical device, partly or completely, temporarily or permanently, into the esophagus, trachea, colon, biliary tract, urinary tract, vascular system or other location within a human or veterinary patient. For example, many treatments of the vascular system entail the introduction of a device such as a guidewire, catheter, stent, arteriovenous shunt, angioplasty balloon, a cannula or the like. Other examples of implantable medical devices include, e.g., endoscopes, biopsy probes, wound drains, laparoscopic equipment, urethral inserts, and implants. Most such implantable medical devices are made in whole or in part of metal, and are not part of an electrical circuit.

When a patient with one of these implanted devices is subjected to high intensity magnetic fields, such as during magnetic resonance imaging (MRI), electrical currents are induced in the metallic portions of the implanted devices. The electrical currents so induced often create substantial amounts of heat. The heat can cause extensive damage to the tissue surrounding the implantable medical device.

Furthermore, when a patient with one of these implanted devices undergoes MRI, signal loss and disruption the diagnostic image often occur as a result of the presence of a metallic object, which causes a disruption of the local magnetic field. This disruption of the local magnetic field alters the relationship between position and frequency, which are crucial for proper image reconstruction. Therefore, patients with implantable medical devices are generally advised not to undergo MRI procedures. In many cases, the presence of such a device is a strict contraindication for MRI (See Shellock, F. G., Magnetic Resonance Procedures: Health Effects and Safety, 2001 Edition, CRC Press, Boca Raton, Fla., and Food and Drug Administration, Magnetic Resonance Diagnostic Device: Panel Recommendation and Report on Petitions for MR Reclassification, Federal register, 1988, 53, 7575–7579). Any contraindication such as this, whether a strict or relative contraindication, is serious problem since it deprives the patient from undergoing an MRI examination, or even using MRI to guide other therapies, such as proper placement of diagnostic and/or therapeutics devices including angioplasty balloons, RF ablation catheters for treatment of cardiac arrythmias, sensors to assess the status of pharmacological treatment of tumors, or verification of proper placement of other permanently implanted medical devices. The rapidly growing capabilities and use of MRI in these and other areas prevent an increasingly large group of patients from benefiting from this powerful diagnostic and intra-operative tool.

The use of implantable medical devices is well known in the prior art. Thus, e.g., U.S. Pat. No. 4,180,600 discloses and claims an implantable medical device comprising a shielded conductor wire consisting of a conductive copper core and a magnetically soft alloy metallic sheath metallurgically secured to the conductive core, wherein the sheath consists essentially of from 2 to 5 weight percent of molybdenum, from about 15 to about 23 weight percent of iron, and from about 75 to about 85 weight percent of nickel. Although the device of this patent does provide magnetic shielding, it still creates heat when it interacts with strong magnetic fields, and it can still disrupt and distort magnetic resonance images.

Thus, e.g., U.S. Pat. No. 5,817,017 discloses and claims an implantable medical device having enhanced magnetic image visibility. The magnetic images are produced by known magnetic imaging techniques, such as MRI. The invention disclosed in the '017 patent is useful for modifying conventional catheters, stents, guide wires and other implantable devices, as well as interventional devices, such as for suturing, biopsy, which devices may be temporarily inserted into the body lumen or tissue; and it is also useful for permanently implantable devices.

As is disclosed in the '017 patent, paramagnetic ionic particles are fixedly incorporated and dispersed in selective portions of an implantable medical device such as, e.g., a catheter. When the catheter coated with paramagnetic ionic particles is inserted into a patient undergoing magnetic resonance imaging, the image signal produced by the catheter is of higher intensity. However, paramagnetic implants, although less susceptible to magnetization than ferromagnetic implants, can produce image artifacts in the presence of a strong magnetic field, such as that of a magnetic resonant imaging coil, due to eddy currents generated in the implants by time-varying electromagnetic fields that, in turn, disrupt the local magnetic field and disrupt the image.

Any electrically conductive material, even a non-metallic material, and even if not in an electrical circuit, will develop eddy currents and thus produce electrical potential and thermal heating in the presence of a time-varying electromagnetic field or a radio frequency field.

Thus, there is a need to provide an implantable medical device, which is shielded from strong electromagnetic fields, which does not create large amounts of heat in the presence of such fields, and which does not produce image artifacts when subjected to such fields. It is one object of the present invention to provide such a device, including a shielding device that can be reversibly attached to an implantable medical device.

FIGS. 8A, 8B, 8C, and 8D are schematic sectional views of a substrate 201, which is preferably a part of an implantable medical device.

Referring to FIG. 8A, it will be seen that substrate 201 is coated with nanomagnetic particles 202 on the exterior surface 203 of the substrate.

Referring to FIG. 8B, and in the embodiment depicted therein, the substrate 201 is coated with nanomagnetic particulate 202 on both the exterior surface 203 and the interior surface 204.

Referring to FIG. 8C, and in the preferred embodiment depicted therein, a layer of insulating material 205 separates substrate 201 and the layer of nanomagnetic coating 202.

Referring to FIG. 8D, it will be seen that one or more layers of insulating material 205 separate the inside and outside surfaces of substrate 201 from respective layers of nanomagnetic coating 202.

Figure 9:
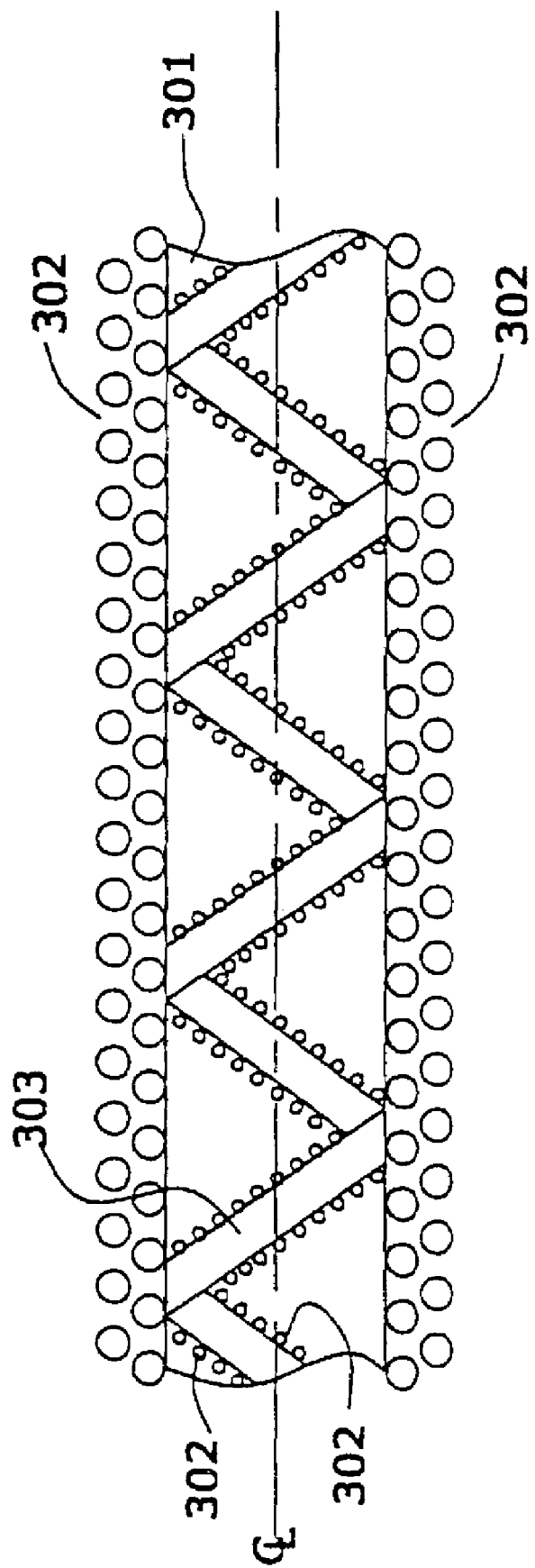
FIG. 9 is a schematic sectional view of an elongated cylinder, similar to the specific medical devices described in this application, coated with nanomagnetic particulate (the cylinder encloses a flexible, expandable helical member, which is also coated with nanomagnetic particulate material)

FIG. 9 is a schematic sectional view of a substrate 301 which is part of an implantable medical device (not shown). Referring to FIG. 9, and in the embodiment depicted therein, it will be seen that substrate 301 is coated with nanomagnetic material 302, which may differ from nanomagnetic material 202.

In one embodiment, the substrate 301 is in the shape of a cylinder, such as an enclosure for a medical catheter, stent, guide wire, and the like. In one aspect of this embodiment, the cylindrical substrate 301 encloses a helical member 303, which is also coated with nanomagnetic particulate material 302.

In another embodiment (not shown), the cylindrical substrate 301 depicted in FIG. 9 is coated with multiple layers of nanomagnetic materials. In one aspect of this embodiment, the multiple layers of nanomagnetic particulate are insulated from each other. In another aspect of this embodiment, each of such multiple layers is comprised of nanomagnetic particles of different sizes and/or densities and/or chemical densities. In one aspect of this embodiment, not shown, each of such multiple layers may have different thickness. In another aspect of this embodiment, the frequency response and degree of shielding of each such layer differ from that of one or more of the other such layers.

Figure 10:
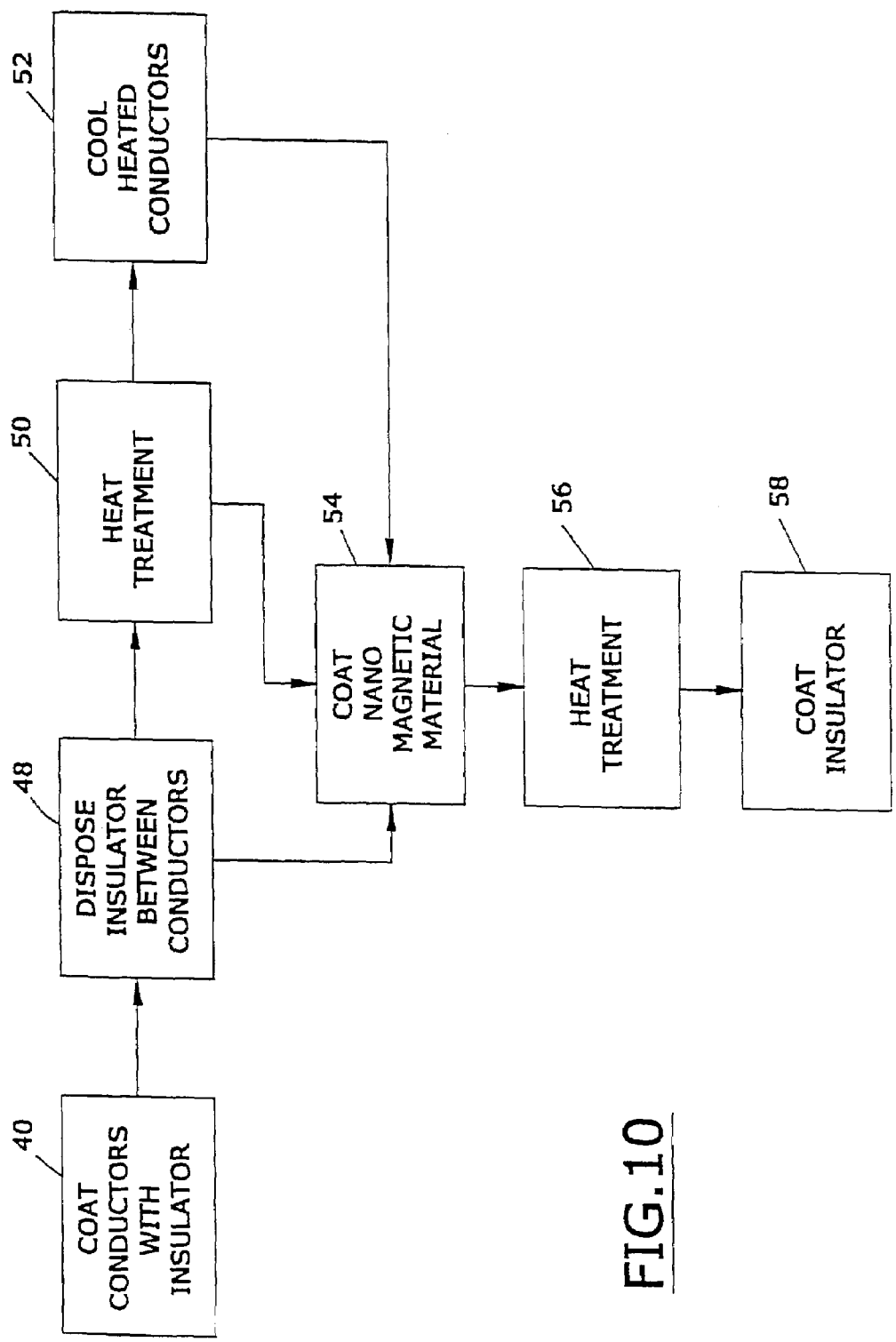
FIG. 10 is a flow diagram of a preferred process of the invention.

FIG. 10 is a flow diagram of a preferred process of the invention. In FIG. 2, reference is made to one or more conductors as being the substrate(s); it is to be understood, however, that other substrate(s) material(s) and/or configurations also may be used.

In the first step of this process depicted in FIG. 10, step 240, the substrate 201 (see FIG. 8A) is coated with electrical insulative material. Suitable insulative materials include nano-sized silicon dioxide, aluminum oxide, cerium oxide, yttrium-stabilized zirconium, silicon carbide, silicon nitride, aluminum nitride, and the like. In general, these nano-sized particles will have a particle distribution such that at least 90 weight percent of the particles have a dimension in the range of from about 10 to about 100 nanometers.

The coated substrate 201 may be prepared by conventional means such as, e.g., the process described in U.S. Pat. No. 5,540,959, the entire disclosure of which is incorporated by reference into this specification. This patent describes and claims a process for preparing a coated substrate, comprising the steps of: (a) creating mist particles from a liquid, wherein: 1. said liquid is selected from the group consisting of a solution, a slurry, and mixtures thereof, 2. said liquid is comprised of solvent and from 0.1 to 75 grams of solid material per liter of solvent, 3. at least 95 volume percent of said mist particles have a maximum dimension less than 100 microns, and 4. said mist particles are created from said first liquid at a rate of from 0.1 to 30 milliliters of liquid per minute; (b) contacting said mist particles with a carrier gas at a pressure of from 761 to 810 millimeters of mercury; (c) thereafter contacting said mist particles with alternating current radio frequency energy with a frequency of at least 1 megahertz and a power of at least 3 kilowatts while heating said mist to a temperature of at least 100 degree centigrade, thereby producing a heated vapor; (d) depositing said heated vapor onto a substrate, thereby producing a coated substrate; and (e) subjecting said coated substrate to a temperature of from about 450 to about 1,400 degree centigrade for at least 10 minutes.

By way of further illustration, one may coat substrate 201 by means of the process disclosed in a text by D. Satas on "Coatings Technology Handbook" (Marcel Dekker, Inc., New York, N.Y., 1991). As is disclosed in such text, one may use cathodic arc plasma deposition (see pages 229 et seq.), chemical vapor deposition (see pages 257 et seq.), sol-gel coatings (see pages 655 et seq.), and the like.

Referring again to FIGS. 8C and 8D, and by way of illustration and not limitation, these Figures are sectional views of the coated substrate 201. It will be seen that, in the embodiments depicted, insulating material 205 separates the substrate and the layer of nanomagnetic material 202. In order to obtain the structure depicted in FIGS. 8C and 8D, one may first coat the substrate with insulating material 205, and then apply a coat of nanomagnetic material 202 on top of the insulating material 205; see, e.g., step 248 of FIG. 10.

The insulating material 205 that is disposed between substrate 201 and the layer of nanomagnetic coating 202 preferably has an electrical resistivity of from about 1,000, 000,000 to about 10,000,000,000,000 ohm-centimeter.

After the insulating material 205 has been deposited, and in one preferred embodiment, the coated substrate is heat-treated in step 250 of FIG. 10. The heat treatment often is preferably used in conjunction with coating processes in which heat is required to bond the insulative material to the substrate 201.

The heat-treatment step 250 may be conducted after the deposition of the insulating material 205, or it may be conducted simultaneously therewith. In either event, and when it is used, it is preferred to heat the coated substrate 201 to a temperature of from about 200 to about 600 degree Centigrade for about 1 minute to about 10 minutes.

Referring again to FIG. 10, and in step 252 of the process, after the coated substrate 201 has been subjected to heat treatment step 250, the substrate is allowed to cool to a temperature of from about 30 to about 100 degree Centigrade over a period of time of from about 3 to about 15 minutes.

One need not invariably heat-treat and/or cool. Thus, referring to FIG. 10, one may immediately coat nanomagnetic particulate onto the coated substrate in step 254, after step 248 and/or after step 250 and/or after step 252.

In step 254, nanomagnetic material(s) are coated onto the previously coated substrate 201. This is best shown in FIGS. 8C and 8D, wherein the nanomagnetic materials are identified as 202.

Nanomagnetic material is magnetic material which has an average particle size less than 100 nanometers and, preferably, in the range of from about 2 to about 50 nanometers. Reference may be had, e.g., to U.S. Pat. No. 5,889,091 (Rotationally Free Nanomagnetic Material), U.S. Pat. Nos. 5,714,136, 5,667,924, and the like. The entire disclosure of each of these United States patents is hereby incorporated by reference into this specification.

Figure 11:
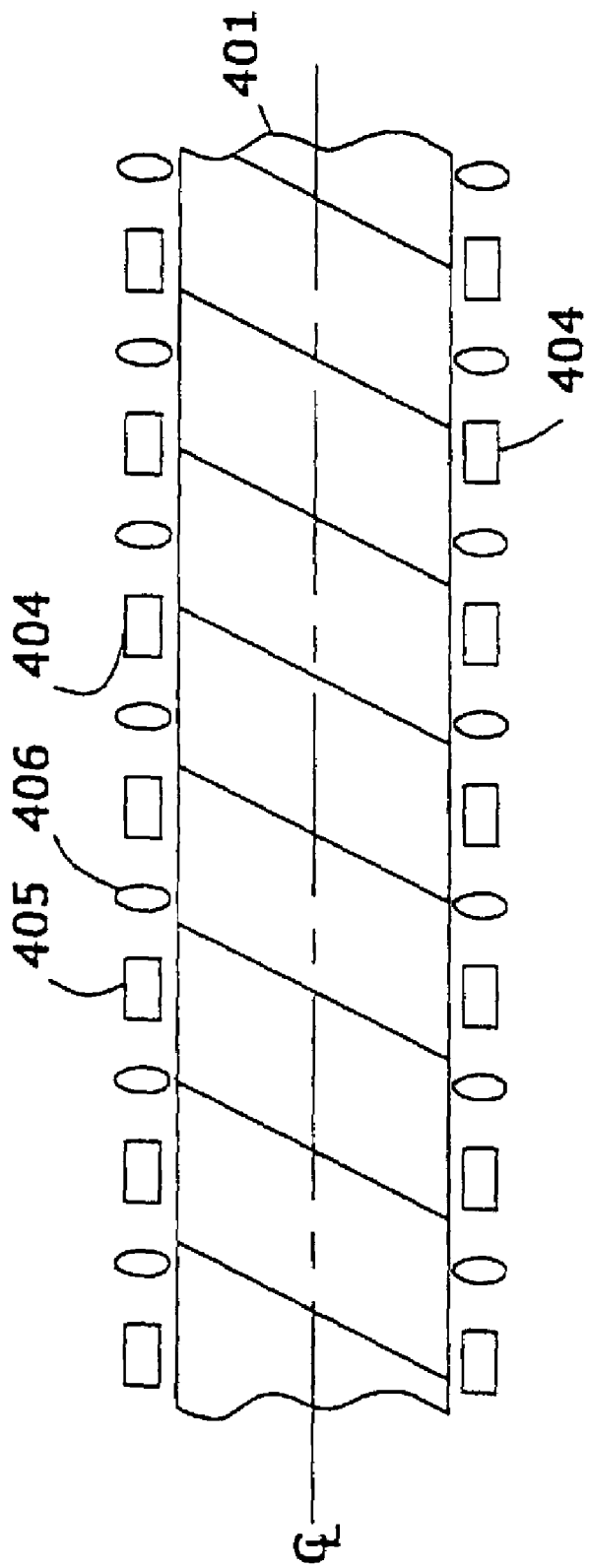
FIG. 11 is a schematic sectional view of a substrate, similar to the specific medical devices described in this application, coated with two different populations of elongated nanomagnetic particulate material.

The nanomagnetic material may be, e.g., nano-sized ferrites such as, e.g., the nanomagnetic ferrites disclosed in U.S. Pat. No. 5,213,851, the entire disclosure of which is hereby incorporated by reference into this specification. This patent discloses and claim a process for coating a layer of ferrite material with a thickness of from about 0.1 to about 500 microns onto a substrate at a deposition rate of from about 0.01 to about 10 microns per minute per 35 square centimeters of substrate surface, comprising the steps of: (a) providing a solution comprised of a first compound and a second compound, wherein said first compound is an iron compound and said second compound is selected from the group consisting of compound of nickel, zinc, magnesium, strontium, barium, manganese, lithium, lanthanum, yttrium, scandium, samarium, europium, terbium, dysprosium, holmium, erbium, ytterbium, lutetium, cerium, praseodymium, thulium, neodymium, gadolinium, aluminum, iridium, lead, chromium, gallium, indium, cobalt, titanium, and mixtures thereof, and wherein said solution is comprised of from about 0.01 to about 1 kilogram of a mixture consisting essentially of said compounds per liter of said solution; (b) subjecting said solution to ultrasonic sound waves at a frequency in excess of 20 kilohertz, and to an atmospheric pressure of at least about 600 millimeters of mercury, thereby causing said solution to form into an aerosol; (c) providing a radio frequency plasma reactor comprised of a top section, a bottom section, and a radio frequency coil; (d) generating a hot plasma gas within said radio frequency plasma reactor, thereby producing a plasma region; (e) providing a flame region disposed above said top section of said radio frequency plasma reactor; (f) contacting said aerosol with said hot plasma gas within said plasma reactor while subjecting said aerosol to an atmospheric pressure of at least 600 millimeters of mercury, and to a radio frequency alternating current at a frequency of from about 100 kilohertz to about 30 megahertz, thereby forming a vapor; (g) providing a substrate disposed above said flame region; and (h) contacting said vapor with said substrate, thereby forming said layer of ferrite material.

By way of further illustration, one may use the techniques described in an article by M. De Marco, X. W. Wang, et al. on "Mossbauer and Magnetization Studies of Nickel Ferrites", published in the Journal of Applied Physics 73 (10), May 15, 1993, at pages 6287–6289.

In general, the thickness of the layer of nanomagnetic material deposited onto the coated substrate 201 is from about 100 nanometers to about 10 micrometers and, more preferably, from about 0.1 to 3 microns.

Referring again to FIG. 10, after the nanomagnetic material is coated in step 254, the coated substrate may be heat-treated in step 256. In this optional step 256, it is preferred to subject the coated substrate 201 to a temperature of from about 200 to about 600 degree Centigrade for from about 1 to about 10 minutes.

In one embodiment (not shown) additional insulating layers may be coated onto the substrate 201, by one or more of the processes disclosed hereinabove; see, e.g., optional step 258 of FIG. 10.

Without wishing to be bound to any particular theory, the applicants believe that the nanomagnetic particles 202 trap and pin magnetic lines of flux impinging on substrate 201, while at the same time minimizing or eliminating the flow of electrical currents through the coating and/or substrate.

In order to function optimally, the nanomagnetic material(s) 202 preferably have a specified magnetization. As is know to those skilled in the art, magnetization is the magnetic moment per unit volume of a substance. Reference may be had, e.g., to U.S. Pat. Nos. 4,169,998, 4,168,481, 4,166,263, 5,260,132, 4,778,714, and the like. The entire disclosure of each of these United States patents is hereby incorporated by reference into this specification.

Referring again to FIGS. 8A, 8B, 8C, and 8D, the layer of nanomagnetic particles 202 preferably has a saturation magnetization, at 25 degree Centigrade, of from about 1 to about 36,000 Gauss. and preferably from about 1 to about 26,000 Gauss. In one embodiment, the saturation magnetization at room temperature of the nanomagnetic particles is from about 500 to about 10,000 Gauss. For a discussion of the saturation magnetization of various materials, reference may be had, e.g., to U.S. Pat. Nos. 4,705,613, 4,631,613, 5,543, 070, 4,901,741 (cobalt, samarium, and gadolinium alloys), and the like. The entire disclosure of each of these United States patents is hereby incorporated by reference into this specification. As will be apparent to those skilled in the art, especially upon studying the aforementioned patents, the saturation magnetization of thin films is often higher than the saturation magnetization of bulk objects.

In one embodiment, it is preferred to utilize a thin film with a thickness of less than about 2 microns and a saturation magnetization in excess of 20,000 Gauss. The thickness of the layer of nanomagnetic material is measured from the bottom surface of such layer that contains such material to the top surface of such layer that contain such material; and such bottom surface and/or such top surface may be contiguous with other layers of material (such as insulating material) that do not contain nanomagnetic particles. Thus, e.g., one may make a thin film in accordance with the procedure described at page 156 of Nature, Volume 407, Sep. 14, 2000, that describes a multiplayer thin film that has a saturation magnetization of 24,000 Gauss.

By the appropriate selection of nanomagnetic particles, and the thickness of the film deposited, one may obtain saturation magnetizations of as high as at least about 36,000 Gauss.

In the preferred embodiment depicted in FIG. 8A, the nanomagnetic material 202 may be disposed within an insulating matrix (not shown) so that any heat produced by such particles will be slowly dispersed within such matrix. Such matrix, as indicated hereinabove, may be made from ceria, calcium oxide, silica, alumina, and the like. In general, the insulating material 202 preferably has a thermal conductivity of less than about 20 (calories centimeters/square centimeters-degree second)×10,000. See, e.g., page E-6 of the $63^{rd}$. Edition of the "Handbook of Chemistry and Physics" (CRC Press, Inc. Boca Raton, Fla., 1982).

The nanomagnetic material 202 typically comprises one or more of iron, cobalt, nickel, gadolinium, and samarium atoms. Thus, e.g., typical nanomagnetic materials include alloys of iron, and nickel (permalloy), cobalt, niobium and zirconium (CNZ), iron, boron, and nitrogen, cobalt, iron, boron and silica, iron, cobalt, boron, and fluoride, and the like. These and other materials are described in a book by J. Douglass Adam et al. entitled "Handbook of Thin Film Devices" (Academic Press, San Diego, Calif., 2000). Chapter 5 of this book beginning at page 185 describes "magnetic films for planar inductive components and devices;" and Tables 5.1. and 5.2 in this chapter describes many magnetic materials.

Some of the devices described in this application are substantially flexible. As used in this specification, the term flexible refers to an assembly that can be bent to form a circle with a radius of less than 2 centimeters without braking. Put another way, the bend radius of the coated assembly can be less than 2 centimeters. Reference may be had, e.g., to U.S. Pat. Nos. 4,705,353, 5,946,439, 5,315,365, 4,641,917, 5,913,005, and the like. The entire disclosure of each of these United States patents is hereby incorporated by reference into this specification.

Some of the devices described in this specification are substantially rigid. One such device is a rigid sheath that is adapted to be placed over an endoscope or biopsy probe used inter-operatively with magnetic resonance imaging.

As will be apparent, even when the magnetic insulating properties of the assembly of this invention are not absolutely effective, the assembly still reduces the amount of electromagnetic energy that is transferred to the coated substrate, prevents the rapid dissipation of heat to bodily tissue, and minimization of disruption to the magnetic resonance image.

FIG. 11 is a schematic sectional view of a substrate 401, which is part of an implantable medical device (not shown). Referring to FIG. 11, and in the preferred embodiment depicted therein, it will be seen that substrate 401 is coated with a layer 404 of nanomagnetic material(s). The layer 404, in the embodiment depicted, is comprised of nanomagnetic particulate 405 and nanomagnetic particulate 406. Each of the nanomagnetic particulate 405 and nanomagnetic particulate 406 preferably has an elongated shape, with a length that is greater than its diameter. In one aspect of this embodiment, nanomagnetic particles 405 have a different size than nanomagnetic particles 406. In another aspect of this embodiment, nanomagnetic particles 405 have different magnetic properties than nanomagnetic particles 406. Referring again to FIG. 11, and in the preferred embodiment depicted therein, nanomagnetic particulate material 405 and nanomagnetic particulate material 406 are designed to respond to an static or time-varying electromagnetic fields or effects in a manner similar to that of liquid crystal display (LCD) materials. More specifically, these nanomagnetic particulate materials 405 and nanomagnetic particulate materials 406 are designed to shift alignment and to effect switching from a magnetic shielding orientation to a non-magnetic shielding orientation. As will be apparent, the magnetic shield provided by layer 404, can be turned "ON" and "OFF" upon demand. In yet another embodiment (not shown), the magnetic shield is turned on when heating of the shielded object is detected.

Figure 12:
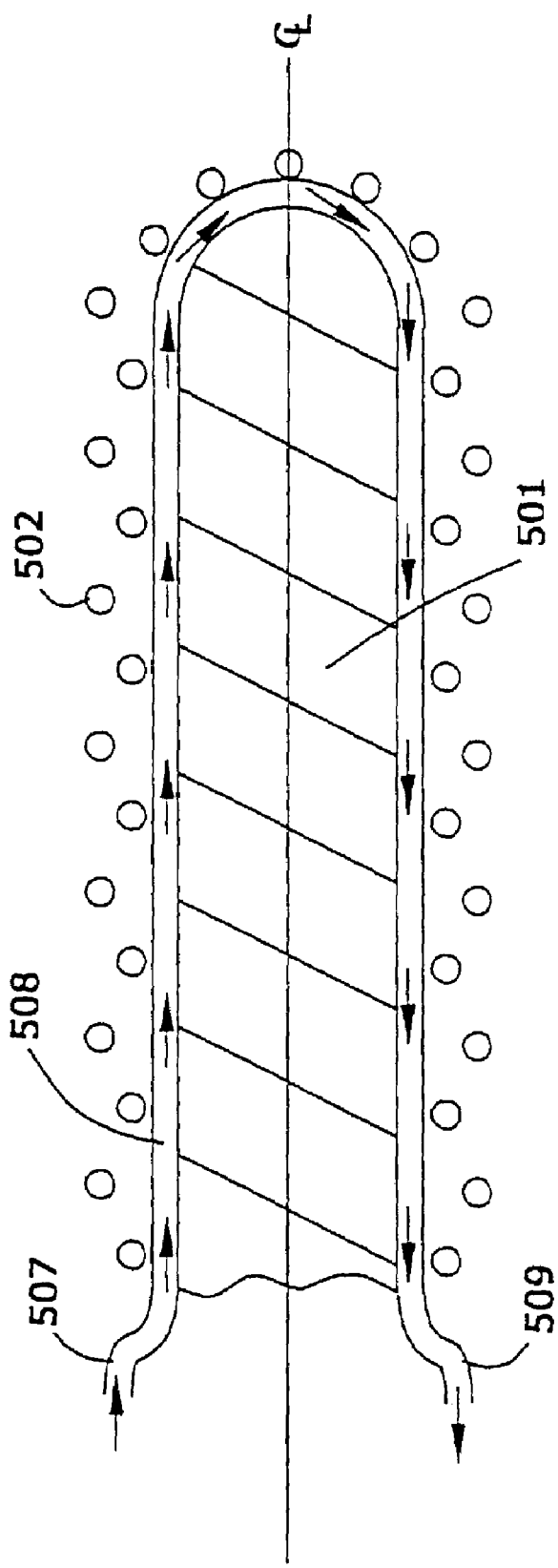
FIG. 12 is a schematic sectional view of an elongated cylinder, similar to the specific medical devices described in this application, coated with nanomagnetic particulate, wherein the cylinder includes a channel for active circulation of a heat dissipation fluid.

FIG. 12 is a schematic sectional view of substrate 501, which is part of an implantable medical device (not shown). Referring to FIG. 12, and to the embodiment depicted therein, it will be seen that substrate 501 is coated with nanomagnetic particulate material 502 which may differ from particulate material 202 and/or particulate material 302. In the embodiment depicted in FIG. 12, the substrate 501 may be a cylinder, such as an enclosure for a catheter, medical stent, guide wire, and the like. The assembly depicted in FIG. 12 includes a channel 508 located on the periphery of the medical device. An actively circulating, heat-dissipating fluid (not shown) can be pumped into channel 508 through port 507, and exit channel 508 through port 509. The heat-dissipation fluid (not shown) will draw heat to another region of the device, including regions located outside of the body where the heat can be dissipated at a faster rate. In the embodiment depicted, the heat-dissipating flow flows internally to the layer of nanomagnetic particles 502.

In another embodiment, not shown, the heat dissipating fluid flows externally to the layer of nanomagnetic particulate material 502.

In another embodiment (not shown), one or more additional polymer layers (not shown) are coated on top of the layer of nomagnetic particulate 502. In one aspect of this embodiment, a high thermal conductivity polymer layer is coated immediately over the layer of nanomagnetic particulate 502; and a low thermal conductivity polymer layer is coated over the high thermal conductivity polymer layer. It is preferred that neither the high thermal conductivity polymer layer nor the low thermal conductivity polymer layer be electrically or magnetically conductive. In the event of the occurrence of "hot spots" on the surface of the medical device, heat from the localized "hot spots" will be conducted along the entire length of the device before moving radially outward through the insulating outer layer. Thus, heat is distributed more uniformly.

Many different devices advantageously incorporate the nanomagnetic film of this invention. In the following section of the specification, various additional devices that incorporate the such film are described.

The disclosure in the following section of the specification relates generally to an implantable medical device that is immune or hardened to electromagnetic insult or interference. More particularly, the invention is directed to implantable medical devices that are not part of an electrical circuit, and that utilize shielding to harden or make these devices immune from electromagnetic insult (i.e. minimize or eliminate the amount of electromagnetic energy transferred to the device), namely magnetic resonance imaging (MRI) insult.

Magnetic resonance imaging (MRI) has been developed as an imaging technique to obtain images of anatomical features of human patients as well as some aspects of the functional activities of biological tissue; reference may be had, e.g., to John D. Enderle's "Introduction to Biomedical Engineering", Academic Press, San Diego, Calif., 2000 and, in particular, pages 783–841 thereof. Reference may also be had to Joseph D. Bronzino's "The Biomedical Engineering Handbook", CRC Press, Boca Raton, Fla., 1995, and in particular pages 1006–1045 thereof. These images have medical diagnostic value in determining the state of the health of the tissue examined.

In an MRI process, a patient is typically aligned to place the portion of the patient's anatomy to be examined in the imaging volume of the MRI apparatus. Such a MRI apparatus typically comprises a primary magnet for supplying a constant magnetic field, Bo, which is typically of from about 0.5 to about 10.0 Tesla, and by convention, is along the z-axis and is substantially homogenous over the imaging volume, and secondary magnets that can provide magnetic field gradients along each of the three principal Cartesian axis in space (generally x, y, and z or x1, x2, and x3, respectively). A magnetic field gradient refers to the variation of the field along the direction parallel to Bo with respect to each of the three principal Cartesian Axis. The apparatus also comprises one or more radio frequency (RF) coils, which provide excitation for and detection of the MRI signal. The RF excitation signal is an electromagnetic wave with an electrical field E and magnetic field B1, and is typically transmitted at frequencies of 3–100 megahertz.

The use of the MRI process with patients who have implanted medical assist devices, such as guide wires, catheters, or stents, often presents problems. These implantable devices are sensitive to a variety of forms of electromagnetic interference (EMI), because the aforementioned devices contain metallic parts that can receive energy from the very intensive EMI fields used in magnetic resonance imaging. The above-mentioned devices may also contain sensing and logic and control systems that respond to low-level electrical signals emanating from the monitored tissue region of the patient. Since these implanted devices are responsive to changes in local electromagnetic fields, the implanted devices are vulnerable to sources of electromagnetic noise. The implanted devices interact with the time-varying radio-frequency (RF) magnetic field (B1), which are emitted during the MRI procedure. This interaction can result in damage to the implantable device, or it can result in heating of the device, which in turn can harm the patient or physician using the device. This interaction can also result in degradation of the quality of the image obtained by the MRI process.

Signal loss and disruption of a magnetic resonance image can be caused by disruption of the local magnetic field, which perturbs the relationship between position and image, which are crucial for proper image reconstruction. More specifically, the spatial encoding of the MRI signal provided by the linear magnetic field can be disrupted, making image reconstruction difficult or impossible. The relative amount of artifact seen on an MR image due to signal disruption is dependent upon such factors as the magnetic susceptibility of the materials used in the implantable medical device, as well as the shape, orientation, and position of the medical device within the body of the patient, which is very often difficult to control.

All non-permanently magnetized materials have non-zero magnetic susceptibilities and are to some extent magnetic. Materials with positive magnetic susceptibilities less than approximately 0.01 are referred to as paramagnetic and are not overly responsive to an applied magnetic field. They are often considered non-magnetic. Materials with magnetic susceptibilities greater than 0.01 are referred to as ferromagnetic. These materials can respond very strongly to an applied magnetic field and are also referred as soft magnets as their properties do not manifest until exposed to an external magnetic field.

Paramagnetic materials (e.g. titanium), are frequently used to encapsulate and shield and protect implantable medical devices due to their low magnetic susceptibilities. These enclosures operate by deflecting electromagnetic fields. However, although paramagnetic materials are less susceptible to magnetization than ferromagnetic materials, they can also produce image artifacts due to eddy currents generated in the implanted medical device by externally applied magnetic fields, such as the radio frequency fields used in the MRI procedures. These eddy currents produce localized magnetic fields, which disrupt and distort the magnetic resonance image. Furthermore, the implanted medical device shape, orientation, and position within the body make it difficult to control image distortion due to eddy currents induced by the RF fields during MRI procedures. Also, since the paramagnetic materials are electrically conductive, the eddy currents produced in them can result in ohmic heating and injury to the patient. The voltages induced in the paramagnetic materials can also damage the medical device, adversely interact with the operation of the device. Typical adverse effects can include improper stimulation of internal tissues and organs, damage to the medical device (melting of implantable catheters while in the MR coil have been reported in the literature), and/or injury to the patient.

Thus, it is desirable to provide protection against electromagnetic interference, and to also provide fail-safe protection against radiation produced by magnetic-resonance imaging procedures. Moreover, it is desirable to provide devices that prevent the possible damage that can be done at the tissue interface due to induced electrical signals and due to thermal tissue damage. Furthermore, it is desirable to provide devices that do not interact with RF fields which are emitted during magnetic-resonance imaging procedures and which result in degradation of the quality of the images obtained during the MRI process.

In one embodiment, there is provided a coating of nanomagnetic particles that consists of a mixture of aluminum oxide (AlO3), iron, and other particles that have the ability to deflect electromagnetic fields while remaining electrically non-conductive. Preferably the particle size in such a coating is approximately 10 nanometers. Preferably the particle packing density is relatively low so as to minimize electrical conductivity. Such a coating when placed on a fully or partially metallic object (such as a guide wire, catheter, stent, and the like) is capable of deflecting electromagnetic fields, thereby protecting sensitive internal components, while also preventing the formation of eddy currents in the metallic object or coating. The absence of eddy currents in a metallic medical device provides several advantages, to wit: (1) reduction or elimination of heating, (2) reduction or elimination of electrical voltages which can damage the device and/or inappropriately stimulate internal tissues and organs, and (3) reduction or elimination of disruption and distortion of a magnetic-resonance image.

FIG. 13 is a schematic view of a catheter assembly 600 similar to the assembly depicted in FIG. 2 of U.S. Pat. No. 3,995,623; the entire disclosure of such patent is hereby incorporated by reference into this specification. Referring to FIG. 6 of such patent, it will be seen that catheter tube 625 contains multiple lumens 603, 611, 613, and 615, which can be used for various functions such as inflating balloons, enabling electrical conductors to communicate with the distal end of the catheter, etc. While four lumens are shown, it is to be understood that this invention applies to a catheter with any number of lumens.

The similar catheter disclosed and claimed in U.S. Pat. No. 3,995,623 may be shielded by coating it in whole or in part with a coating of nanomagnetic particulate, in any of the following manners:

In FIG. 13A, a nanomagnetic material 650 is applied to either the interior wall 650*a* or exterior wall 650*b* of lumens 603, 611, 613, and 615, or imbibed 650*c* into the walls of these lumens within catheter 625, or any combination of these locations.

In FIG. 13B, a nanomagnetic material 650 is applied to the interior walls 650*d* of multiple lumens within a single catheter 625 or the common exterior wall 650*b* or imbibed 650*c* into the common wall.

In FIG. 13C, a nanomagnetic material 650 is applied to the mesh-like material 636 used within the wall of catheter 625 to give it desired mechanical properties.

In another embodiment (not shown) a sheath coated with nanomagnetic material on its internal surface, exterior surface, or imbibed into the wall of sheath is placed over the catheter to shield it from electromagnetic interference. In this manner, existing catheters can be made MRI safe and compatible. The modified catheter assembly thus produced is resistant to electromagnetic radiation.

FIGS. 14A through 14G are schematic views of a catheter assembly consisting of multiple concentric elements. While two elements are shown; 720 and 722, it is to be understood that any number of over-lapping elements may be used, either concentrically or planarly positioned with respect to each other.

Referring to FIGS. 14A–14G, it will be seen that catheter assembly 700 comprises an elongated tubular construction having a single, central or axial lumen 710. The exterior catheter body 722 and concentrically positioned internal catheter body 720 with internal lumen 712 are preferably flexible, i.e., bendable, but substantially non-compressible along its length. The catheter bodies 720 and 722 may be made of any suitable material. A presently preferred construction comprises an outer wall 722 and inner wall 720 made of a polyurethane, silicone, or nylon. The outer wall 722 preferably comprises an imbedded braided mesh of stainless steel or the like to increase torsional stiffness of the catheter assembly 700 so that, when a control handle, not shown, is rotated, the tip sectionally of the catheter will rotate in corresponding manner. The catheter assembly 700 may be shielded by coating it in whole or in part with a coating of nanomagnetic particulate, in any one or more of the following manners:

Referring to FIG. 14A, a nanomagnetic material may be coated on the outside surface of the inner concentrically positioned catheter body 720.

Referring to FIG. 14B, a nanomagnetic material may be coated on the inside surface of the inner concentrically positioned catheter body 720.

Referring to FIG. 14C, a nanomagnetic material may be imbibed into the walls of the inner concentrically positioned catheter body 720 and externally positioned catheter body 722. Although not shown, a nanomagnetic material may be imbibed solely into either inner concentrically positioned catheter body 720 or externally positioned catheter body 722.

Referring to FIG. 14D, a nanomagnetic material may be coated onto the exterior wall of the inner concentrically positioned catheter body 720 and external catheter body 722.

Referring to FIG. 14E, a nanomagnetic material may be coated onto the interior wall of the inner concentrically positioned catheter body 720 and externally wall of externally positioned catheter body 722.

Referring to FIG. 14F, a nanomagnetic material may be coated on the outside surface of the externally positioned catheter body 722.

Referring to FIG. 14G, a nanomagnetic material may be coated onto the exterior surface of an internally positioned solid element 727.

By way of further illustration, one may apply nanomagnetic particulate material to one or more of the catheter assemblies disclosed and claimed in U.S. Pat. Nos. 5,178,803, 5,041,083, 6,283,959, 6,270,477, 6,258,080, 6,248,092, 6,238,408, 6,208,881, 6,190,379, 6,171,295, 6,117,064, 6,019,736, 6,017,338, 5,964,757, 5,853,394, and 6,235,024, the entire disclosure of which is hereby incorporated by reference into this specification. The catheters assemblies disclosed and claimed in the above-mentioned United States patents may be shielded by coating them in whole or in part with a coating of nanomagmetic particulate. The modified catheter assemblies thus produced are resistant to electromagnetic radiation.

FIGS. 15A, 15B, and 15C are schematic views of a guide wire assembly 800 for insertion into vascular vessel (not shown), and it is similar to the assembly depicted in U.S. Pat. No. 5,460,187, the entire disclosure of such patent is incorporated by reference into this specification. Referring to FIG. 15A, a coiled guide wire 810 is formed of a proximal section (not shown) and central support wire 820 which terminates in hemispherical shaped tip 815. The proximal end has a retaining device (not shown) enables the person operating the guide wire to turn an orient the guide wire within the vascular conduit.

The guide wire assembly may be shielded by coating it in whole or in part with a coating of nanomagnetic particulate, in any of the following manners:

Referring to FIG. 15A; the nanomagnetic material 650 is coated on the exterior surface of the coiled guidewire 810.

Referring to FIG. 15B; the nanomagnetic material 650 is coated on the exterior surface of the central support wire 820.

Referring to FIG. 15C; the nanomagnetic material 650 is coated on all guide wire assembly components including coiled guide wire 810, tip 815, and central support wire 820.

The modified guide wire assembly thus produced is resistant to electromagnetic radiation.

By way of further illustration, one may coat with nanomagnetic particulate matter the guide wire assemblies disclosed and claimed in U.S. Pat. Nos.: 5,211,183, 6,168,604, 6,093,157, 6,019,737, 6,001,068, 5,938,623, 5,797,857, 5,588,443, and 5,452,726 the entire disclosure of which is hereby incorporated by reference into this specification. The modified guide wire assemblies thus produced are resistant to electromagnetic radiation.

Figure 16A:
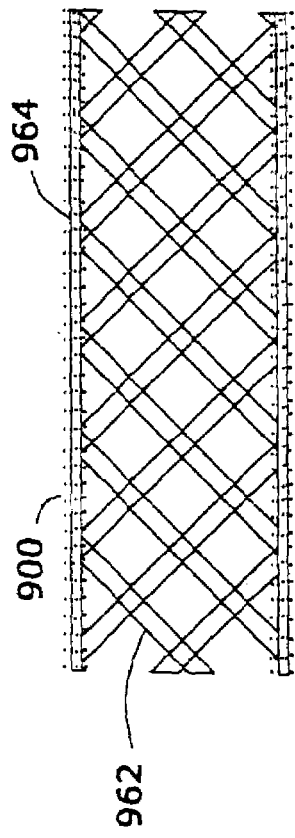
FIGS. 16A and 16B are schematic views of an implantable stent coated with nanomagnetic particulate material.
Figure 16B:
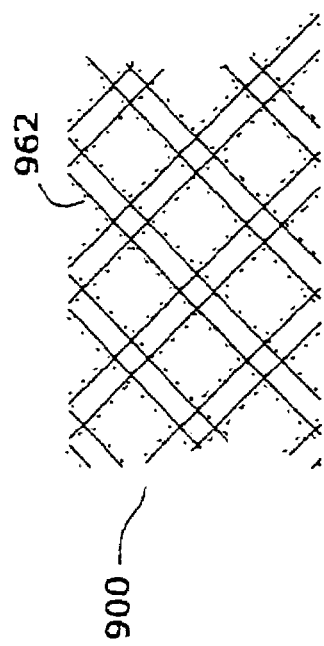

FIGS. 16A and 16B are schematic views of a medical stent assembly 900 similar to the assembly depicted in FIG. 15 of U.S. Pat. No. 5,443,496; the entire disclosure of such patent is hereby incorporated by reference into this specification.

Referring to FIG. 16A, a self-expanding stent 900 comprising joined metal stent elements 962 are shown. The stent 960 also comprises a flexible film 964. The flexible film 964 can be applied as a sheath to the metal stent elements 962 after which the stent 960 can be compressed, attached to a catheter, and delivered through a body lumen to a desired location. Once in the desired location, the stent 960 can be released from the catheter and expanded into contact with the body lumen, where it can conform to the curvature of the body lumen. The flexible film 964 is able to form folds, which allow the stent elements to readily adapt to the curvature of the body lumen. The medical stent assembly disclosed and claimed in U.S. Pat. No. 5,443,496 may be shielded by coating it in whole or in part with a nanomagnetic coating in any of the following manners:

Referring to FIG. 16A, flexible film 964 may be coated with a nanomagnetic coating on its inside or outside surfaces, or within the film itself.

In one embodiment, a stent (not shown) is coated with a nanomagnetic material.

It is to be understood that any one of the above embodiments may be used independently or in conjunction with one another within a single device.

In yet another embodiment (not shown), a sheath (not shown), coated or imbibed with a nanomagnetic material is placed over the stent, particularly the flexible film 964, to shield it from electromagnetic interference. In this manner, existing stents can be made MRI safe and compatible.

By way of illustration and not limitation, one may coat one or more of the medical stent assemblies disclosed and claimed in U.S. Pat. Nos. 6,315,794, 6,190,404, 5,968,091, 4,969,458, 6,342,068, 6,312,460, 6,309,412, and 6,305,436, the entire disclosure of each of which is hereby incorporated by reference into this specification. The medical stent assemblies disclosed and claimed in the above-mentioned United States patents may be shielded by coating them in whole or in part with a coating of nanomagmetic particulate, as described above. The modified medical stent assemblies thus produced are resistant to electromagnetic radiation.

Figure 17:
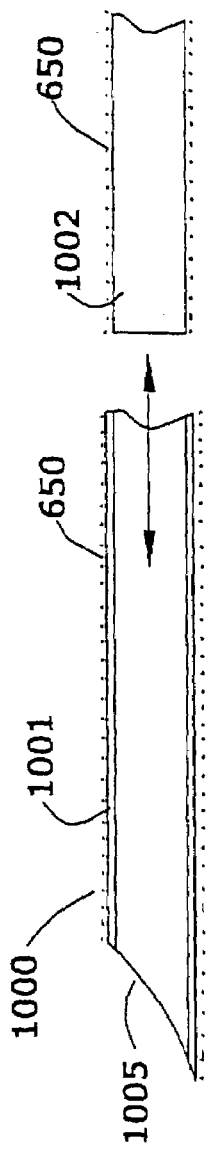
FIG. 17 is a schematic view of a biopsy probe coated with nanomagnetic particulate material.

FIG. 17 is a schematic view of a biopsy probe assembly 1000 similar to the assembly depicted in FIG. 1 of U.S. Pat. No. 5,005,585 the entire disclosure of such patent is hereby incorporated by reference into this specification.

Referring to FIG. 17, the biopsy probe assembly is composed of three separate components, a hollow tubular cannula or needle 1001, a solid intraluminar rod-like stylus 1002, and a clearing rod or probe (not shown).

The components of the assembly are preferably formed of an alloy, such as stainless steel, which is corrosion resistant and non-toxic. Cannula 1001 has a proximal end (not shown) and a distal end 1005 that is cut at an acute angle with respect to the longitudinal axis of the cannula and provides an annular cutting edge.

By way of further illustration, biopsy probe assemblies are disclosed and claimed in U.S. Pat. Nos.: 4,671,292, 5,437,283, 5,494,039, 5,398,690, and 5,335,663, the entire disclosure of each of which is hereby incorporated by reference into this specification. The biopsy probe assemblies disclosed and claimed in the above-mentioned United States patents may be shielded by coating them in whole or in part with a coating of nanomagmetic particulate, in any of the following manners: Cannula 1001 may be coated, intraluminar stylus 1002 may be coated, and/or the clearing rod may be coated.

In one variation on this design (not shown), a biocompatible sheath is placed over the coated cannula 1001 to protect the nanomagnetic coating from abrasion and from contacting body fluids.

In one variation on this design (not shown), the biocompatible sheath has on its interior surface or within its walls a nanomagnetic coating.

In yet another embodiment (not shown), a sheath (not shown), coated or imbibed with a nanomagnetic material is placed over the biopsy probe, to shield it from electromagnetic interference. In this manner, existing stents can be made MRI safe and compatible.

The modified biopsy probe assemblies thus produced are resistant to electromagnetic radiation.

Figure 18B:
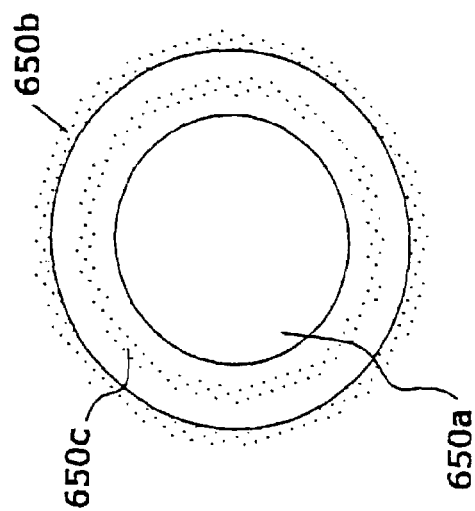
FIGS. 18A and 18B are schematic views of a tube of an endoscope coated with nanomagnetic particulate material.
Figure 18A:
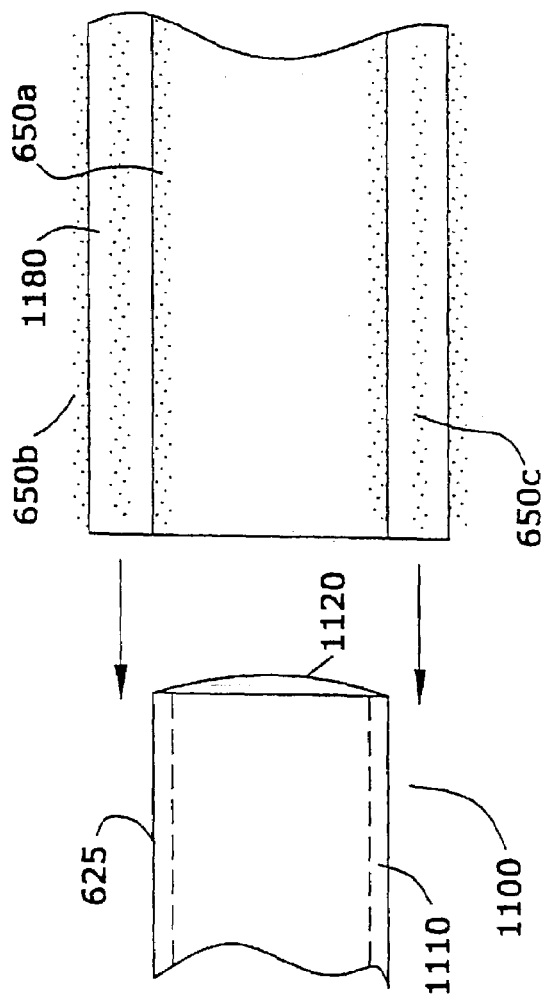

FIGS. 18A and 18B are schematic views of a flexible tube endoscope assembly 1180 similar to the assembly depicted in FIG. 1 of U.S. Pat. No. 5,058,567 the entire disclosure of such patent is hereby incorporated by reference into this specification.

MRI is increasingly being used interoperatively to guide the placement of medical devices such as endsocpes which are very good at treating or examining tissues close up, but generally cannot accurately determine where the tissues being examined are located within the body.

Referring to FIG. 18A, the endoscope 1100 employs a flexible tube 1110 with a distally positioned objective lens 1120. Flexible tube 1110 is preferably formed in such manner that the outer side of a spiral tube is closely covered with a braided-wire tube (not shown) formed by weaving fine metal wires into a braid. The spiral tube is formed using a precipitation hardening alloy material, for example, beryllium bronze (copper-beryllium alloy).

By way of further illustration, endoscope tube assemblies are disclosed and claimed in U.S. Pat. Nos. 4,868,015, 4,646,723, 3,739,770, 4,327,711, and 3,946,727, the entire disclosure of each of which is hereby incorporated by reference into this specification. The endoscope tube assemblies disclosed and claimed in the above-mentioned United States patents may be shielded by coating them in whole or in part with a coating of nanomagmetic particulate, in any of the following manners:

Referring to FIG. 18A; sheath 1180 is a sheath coated with nanomagnetic material on its inside surface 650a, exterior surface 650b, or imbibed into its structure 650c; and such sheath is placed over the endoscope, particularly the flexible tube 1110, to shield it from electromagnetic interference.

In yet another embodiment (not shown), flexible tube 1110 is coated with nanomagnetic materials on its internal surface, or imbibed with nanomagnetic materials within its wall.

In another embodiment (not shown), the braided-wire element within flexible tube 1110 is coated with a nanomagnetic material.

In this manner, existing endoscopes can be made MRI safe and compatible. The modified endoscope tube assemblies thus produced are resistant to electromagnetic radiation.

Figure 19A:
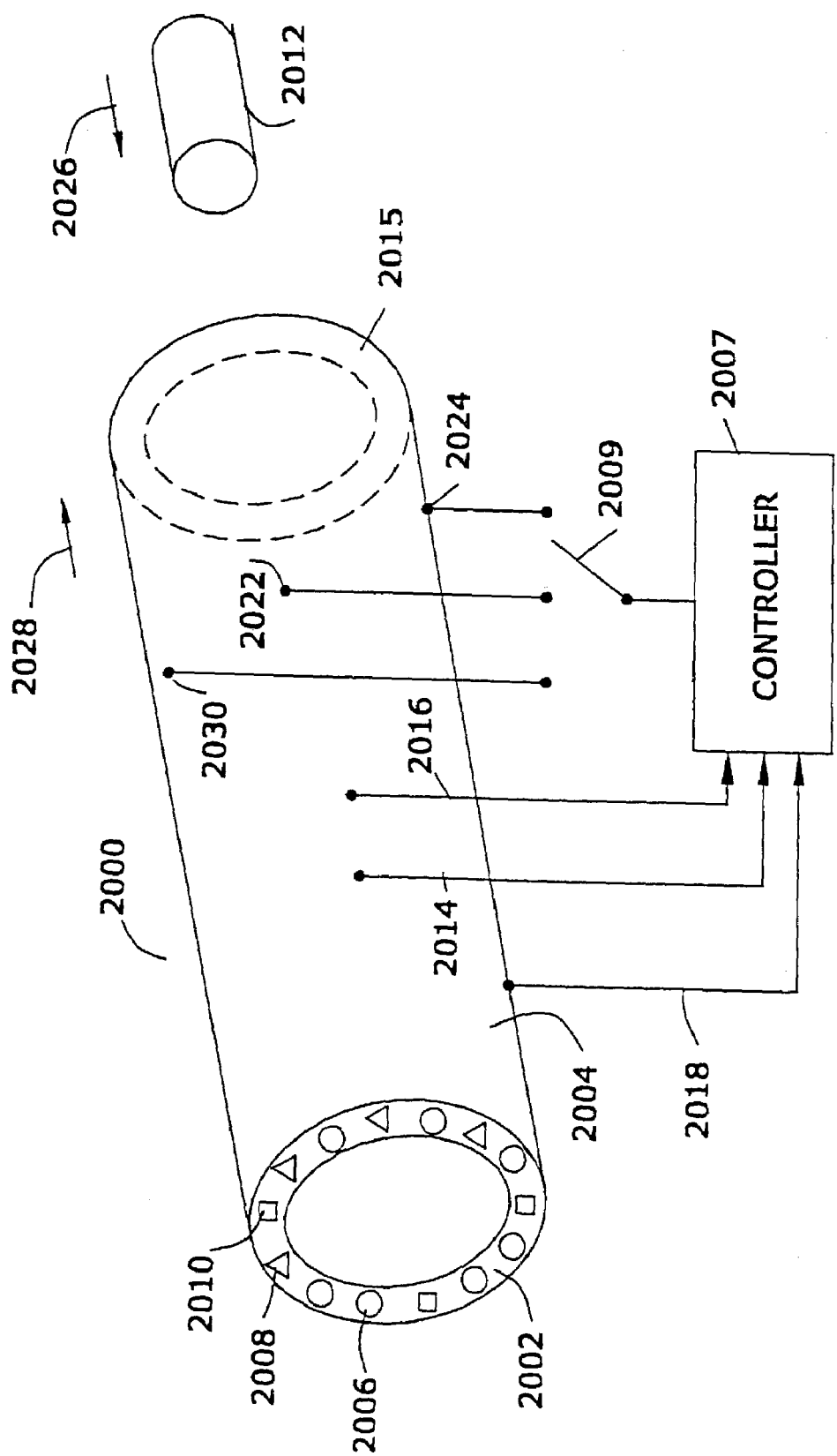
FIGS. 19A and 19B are schematics f one embodiment of the magnetically shielding assembly of this invention.

FIG. 19 is a schematic illustration of a sheath assembly 2000 comprised of a sheath 2002 whose surface 2004 is comprised of a multiplicity of nanomagnetic material 2006, 2008, and 2010. In one embodiment, the nanomagnetic material consists of or comprises nanomagnetic liquid crystal material. Additionally, nanomagnetic materials 2006, 2008, and 2010 may be placed on the inside surface of sheath 2002, imbibed into the wall of sheath 2002, or any combination of these locations.

The sheath 2002 may be formed from electrically conductive materials that include metals, carbon composites, carbon nanotubes, metal-coated carbon filaments (wherein the metal may be either a ferromagnetic material such as nickel, cobalt, or magnetic or non-magnetic stainless steel; a paramagnetic material such as titanium, aluminum, magnesium, copper, silver, gold, tin, or zinc; a diamagnetic material such as bismuth, or well known superconductor materials), metal-coated ceramic filaments (wherein the metal may be one of the following metals: nickel, cobalt, magnetic or non-magnetic stainless steel, titanium, aluminum, magnesium, copper, silver, gold, tin, zinc, bismuth, or well known superconductor materials, a composite of metal-coated carbon filaments and a polymer (wherein the polymer may be one of the following: polyether sulfone, silicone, polymide, polyvinylidene fluoride, epoxy, or urethane), a composite of metal-coated ceramic filaments and a polymer (wherein the polymer may be one of the following: polyether sulfone, silicone, polymide, polyvinylidene fluoride, epoxy, or urethane), a composite of metal-coated carbon filaments and a ceramic (wherein the ceramic may be one of the following: cement, silicates, phosphates, silicon carbide, silicon nitride, aluminum nitride, or titanium diboride), a composite of metal-coated ceramic filaments and a ceramic (wherein the ceramic may be one of the following: cement, silicates, phosphates, silicon carbide, silicon nitride, aluminum nitride, or titanium diboride), or a composite of metal-coated (carbon or ceramic) filaments (wherein the metal may be one of the following metals: nickel, cobalt, magnetic or non-magnetic stainless steel, titanium, aluminum, magnesium, copper, silver, gold, tin, zinc, bismuth, or well known superconductor materials), and a polymer/ceramic combination (wherein the polymer may be one of the following: polyether sulfone, silicone, polymide, polyvinylidene fluoride, or epoxy and the ceramic may be one of the following: cement, silicates, phosphates, silicon carbide, silicon nitride, aluminum nitride, or titanium diboride).

In one preferred embodiment, the sheath 2002 is comprised of at least about 50 volume percent of the nanomagnetic material described elsewhere in this specification.

As is known to those skilled in the art, liquid crystals are nonisotrpic materials (that are neither crystalline nor liquid) composed of long molecules that, when aligned, are parallel to each other in long clusters. These materials have properties intermediate those of crystalline solids and liquids. See, e.g., page 479 of George S. Brady et al.'s "Materials Handbook," Thirteenth Edition (McGraw-Hill, Inc., New York, 1991).

Ferromagnetic liquid crystals are known to those in the art, and they are often referred to as FMLC. Reference may be had, e.g., to U.S. Pat. Nos. 4,241,521, 6,451,207, 5,161, 030, 6,375,330, 6,130,220, and the like. The entire disclosure of each of these United States patents is hereby incorporated by reference into this specification.

Reference also may be had to U.S. Pat. No. 5,825,448, which describes a reflective liquid crystalline diffractive light valve. The figures of this patent illustrate how the orientations of the magnetic liquid crystal particles align in response to an applied magnetic field.

Referring again to FIG. 19A, and in the embodiment depicted therein, it will be seen that sheath 2002 may be disposed in whole or in part over medical device 2012. In the embodiment depicted, the sheath 2002 is shown as being bigger that the medical device 2012. It will be apparent that such sheath 2002 may be smaller than the medical device 2012, may be the same size as the medical device 2012, may have a different cross-sectional shape than the medical 2012, and the like.

In one preferred embodiment, the sheath 2002 is disposed over the medical device 2012 and caused to adhere closely thereto. One may create this adhesion either by use of adhesive(s) and/or by mechanical shrinkage.

In one embodiment, shrinkage of the sheath 2012 is caused by heat, utilizing well known shrink tube technology. Reference may be had, e.g., to U.S. Pat. Nos. 6,438,229, 6,245,053, 6,082,760, 6,055,714, 5,903,693, and the like. The entire disclosure of each of these United States patents is hereby incorporated by reference into this specification.

In another embodiment of the invention, the sheath 2002 is a rigid or flexible tube formed from polytetrafluoroethylene that is heat shrunk into resilient engagement with the implantable medical device. The sheath can also be formed from heat shrinkable polymer materials e.g., low density polyethylene (LDPE), linear low-density polyethylene (LL-DPE), ethylene vinyl acrylate (EVA), ethylene methacrylate (EMA), ethylene methacrylate acid (EMAA) and ethyl glycol methacrylic acid (EGMA). The polymer material of the heat shrinkable sheath should have a Vicat softening point less than 50 degrees Centigrade and a melt index less than 25. A particularly suitable polymer material for the sheath of the invention is a copolymer of ethylene and methyl acrylate which is available under the trademark Lotryl 24MA005 from Elf Atochem. This copolymer contains 25% methyl acrylate, has a Vicat softening point of about 43 degree centigrade and a melt index of about 0.5.

In another embodiment of the invention, the sheath 2002 is a collapsible tube that can be extended over the implantable medical device such as by unrolling or stretching.

In yet another embodiment of the invention, the sheath 2002 contains a tearable seam along its axial length, to enable the sheath to be withdrawn and removed from the implantable device without explanting the device or disconnecting the device from any attachments to its proximal end, thereby enabling the electromagnetic shield to be removed after the device is implanted in a patient. This is a preferable feature of the sheath, since it eliminates the need to disconnect any devices connected to the proximal (external) end of the device, which could interrupt the function of the implanted medical device. This feature is particularly critical if the shield is being applied to a life-sustaining device, such as a temporary implantable cardiac pacemaker.

The ability of the sheath 1180 or 2002 to be easily removed, and therefore easily disposed, without disposing of the typically much more expensive medical device being shielded, is a preferred feature since it prevents cross-contamination between patients using the same medical device.

In still another embodiment of the invention, an actively circulating, heat-dissipating fluid can be pumped into one or more internal channels within the sheath. The heat-dissipation fluid will draw heat to another region of the device, including regions located outside of the body where the heat can be dissipated at a faster rate. The heat-dissipating flow may flow internally to the layer of nanomagnetic particles, or external to the layer of nanomagnetic particulate material.

Figure 19B:
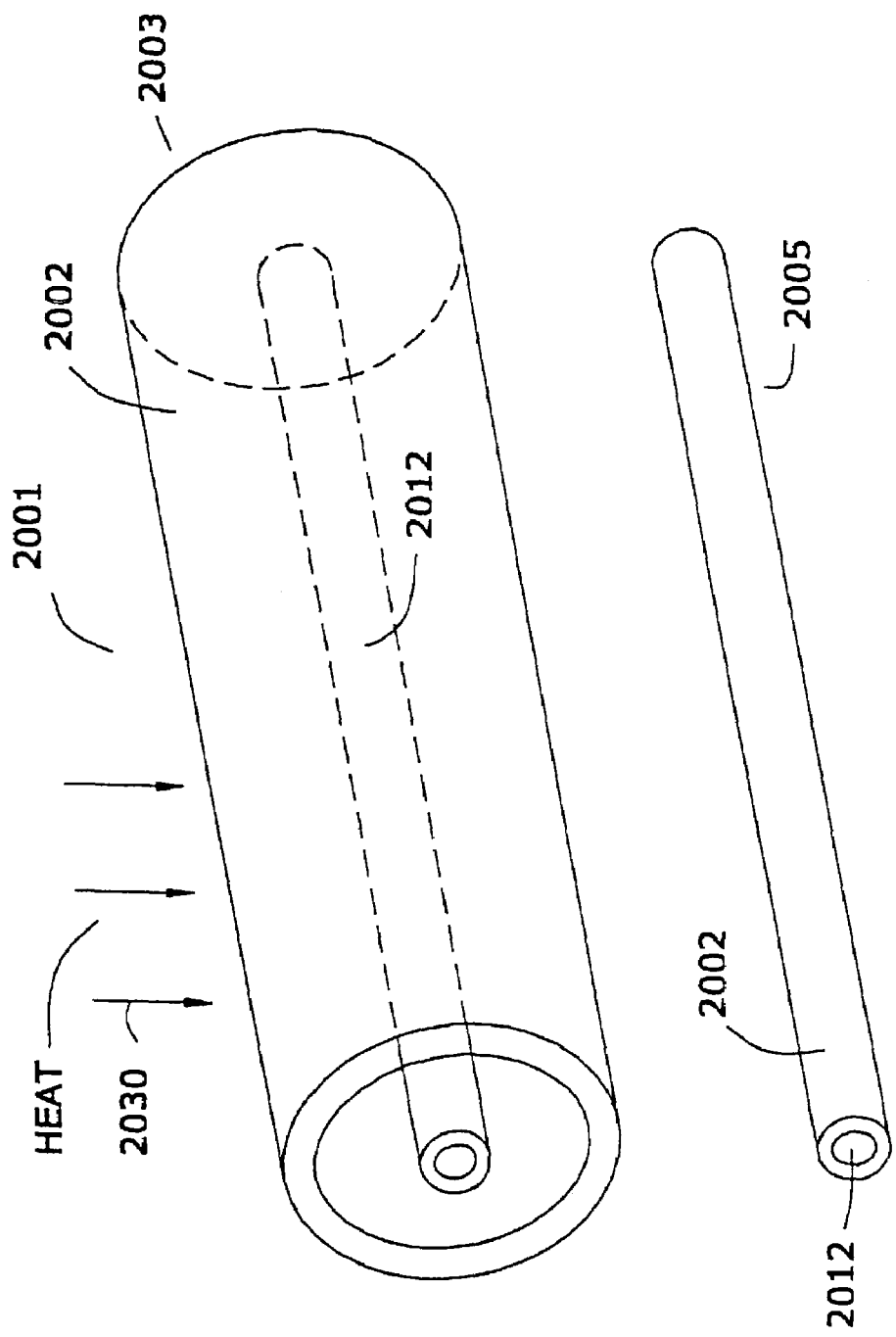

FIG. 19B illustrates a process 2001 in which heat 2030 is applied to a shrink tube assembly 2003 to produce the final product 2005. For the sake of simplicity of representation, the controller 2007 has been omitted from FIG. 19B.

Referring again to FIG. 19A, and in the preferred embodiment depicted therein, it will be seen that a controller 2007 is connected by switch 2009 to the sheath 2002. The controller 2007. A multiplicity of sensors 2014 and 2016, e.g., can detect the effectiveness of sheath 2002 by measuring, e.g., the temperature and/or the electromagnetic field strength within the shield 2012. One or more other sensors 2018 are adapted to measure the properties of sheath 2012 at its exterior surface 2004.

For the particular sheath embodiment utilizing a liquid crystal nanomagnetic particle construction, and depending upon the data received by controller 2007, the controller 2007, may change the shielding properties of shield 2012 by delivering electrical and/or magnetic energy to locations 2020, 2022, 2024, etc. The choice of the energy to be delivered, and its intensity, and its location, and its duration, will vary depending upon the status of the sheath 2012.

In the embodiment depicted in FIG. 19, the medical device may be moved in the direction of arrow 2026, while sheath may be moved in the direction of arrow 2028, to produce the assembly 2001 depicted in FIG. 19B. Thereafter, heat may be applied to this assembly to produce the assembly 2005 depicted in FIG. 19B.

In one embodiment, not shown, the sheath 2002 is comprised of an elongated element consisting of a proximal end and a distal end, containing one or more internal hollow lumens, whereby the lumens at said distal end may be open or closed, is used to temporarily or permanently encase an implantable medical device.

In this embodiment, the elongated hollow element is similar to the sheath disclosed and claimed in U.S. Pat. No. 5,964,730; the entire disclosure of which is hereby incorporated by reference into this specification.

Referring again to FIG. 19A, and in the embodiment depicted therein, the sheath 2002 is preferably coated and/or impregnated with nanomagnetic shielding material 2006/2008/2010 that comprises at least 50 percent of its external surface, and/or comprises at least 50 percent of one or more lumen internal surfaces, or imbibed within the wall 2015 of sheath 2002, thereby protecting at least fifty percent of the surface area of one or more of its lumens, or any combination of these surfaces or areas, thus forming a shield against electromagnetic interference for the encased medical device.

Figure 20A:
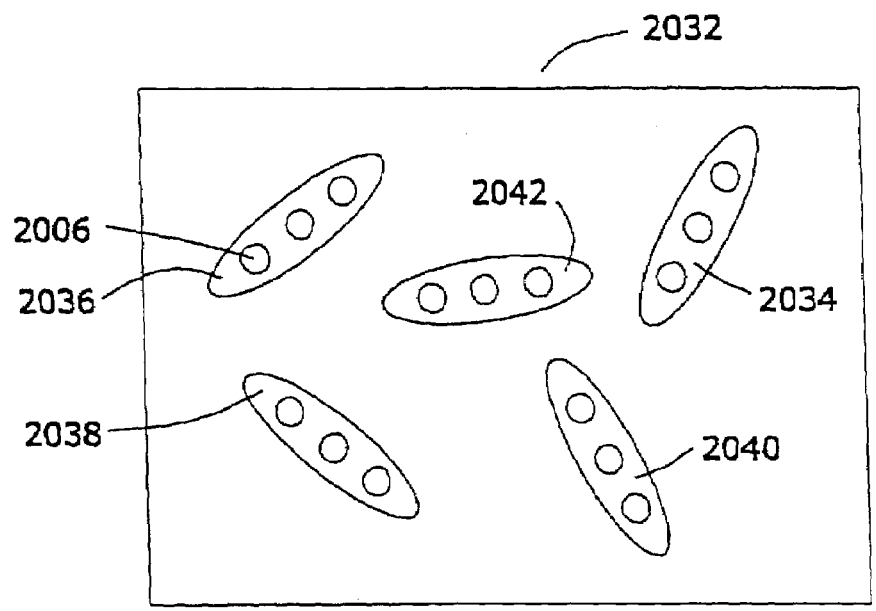
FIGS. 20A, 20B, 20C, 20D, 20E, and 20F are enlarged sectional views of a portion of a shielding assembly illustrating nonaligned and magnetically aligned nanomagnetic liquid crystal materials in different configurations.

FIG. 20A is a schematic of a multiplicity of liquid crystals 2034, 2036, 2038, 2040, and 2042 disposed within a matrix 2032. As will be apparent, each of these liquid crystals is comprised of nanomagnetic material 2006. In the configuration illustrated in FIG. 20A, the liquid crystals 2034 et seq. are not aligned.

Figure 20B:
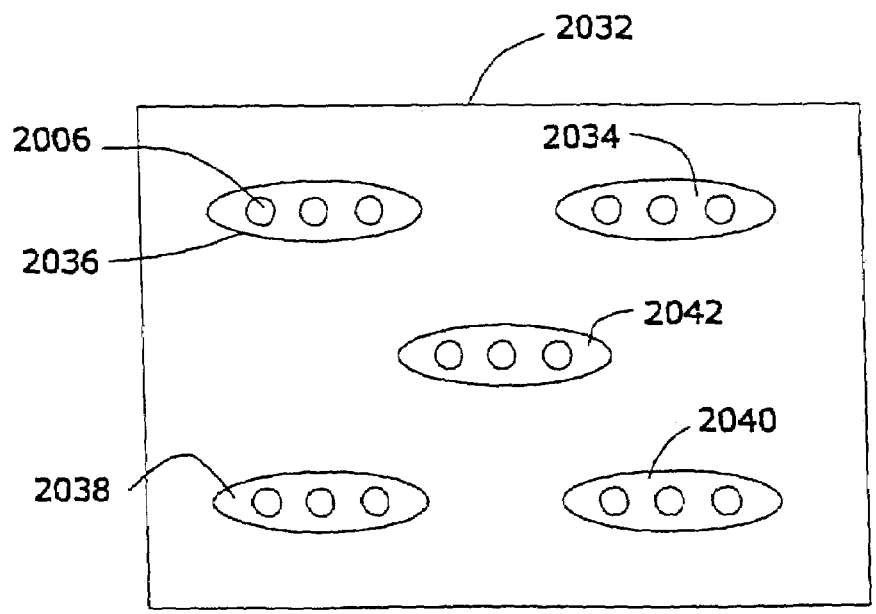

By comparison, in the configuration depicted in FIG. 20B, such liquid crystals 2034 are aligned. Such alignment is caused by the application of an external energy field (not shown).

Figure 20C:
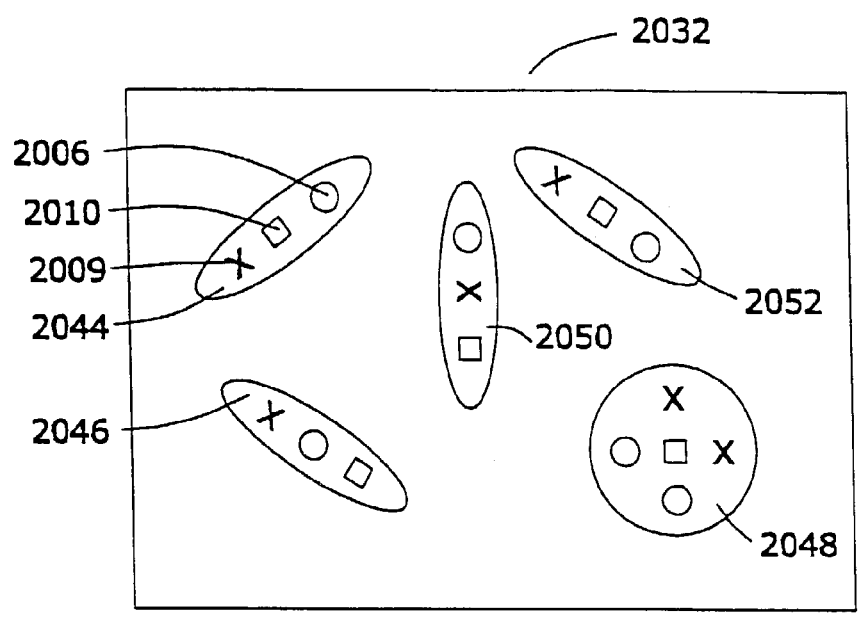
Figure 20D:
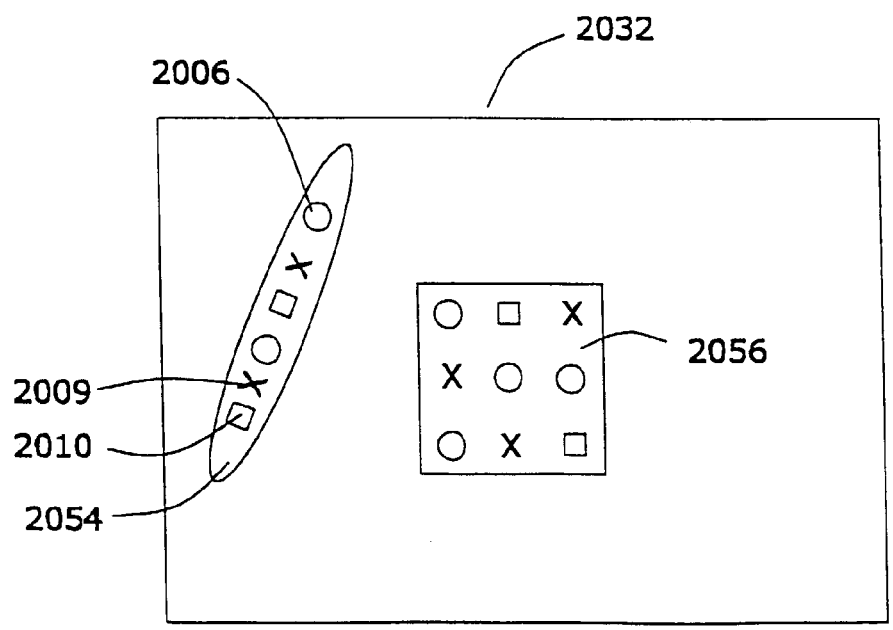
Figure 20E:
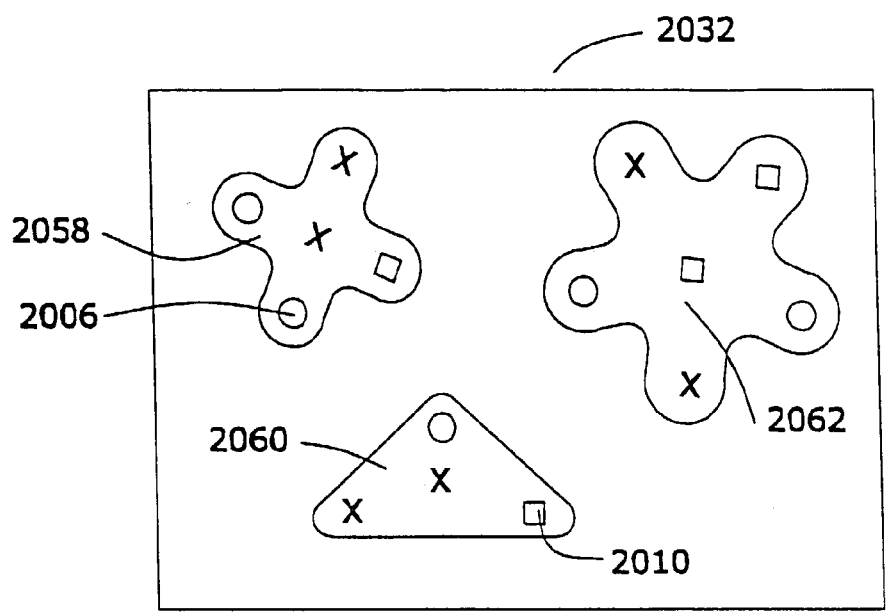
Figure 20F:
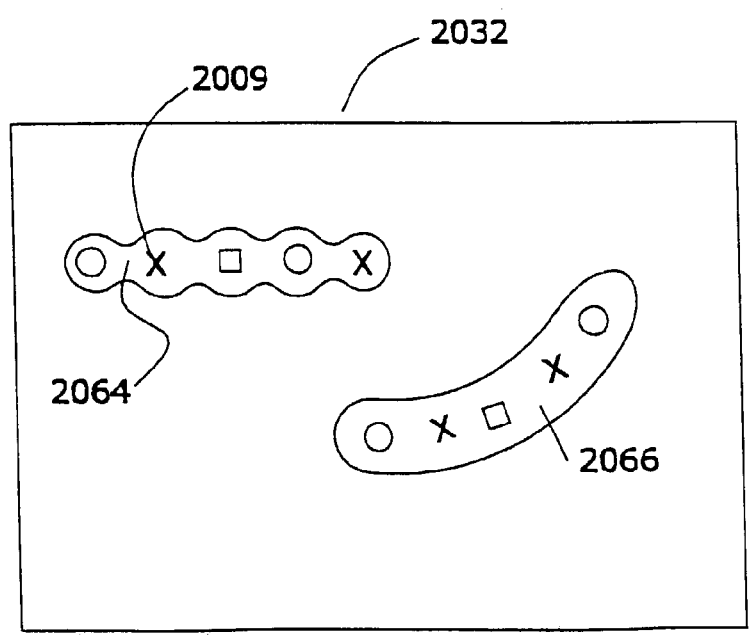

The liquid crystals disposed within the matrix 2032 may have different concentrations and/or compositions of nanomagnetic particles 2006, 2009, and/or 2010; see FIG. 20C and liquid crystals 2044, 2046, 2048, 2050, and 2052. Alternatively, or additionally, the liquid crystals may have different shapes; see FIGS. 20D, 20E, and 20F and liquid crystals 2054 and 2056, 2058, 2060, 2062, 2064, and 2066. As will be apparent, by varying the size, shape, number, location, and/or composition of such liquid crystals, one may custom design any desired response.

Figure 21:
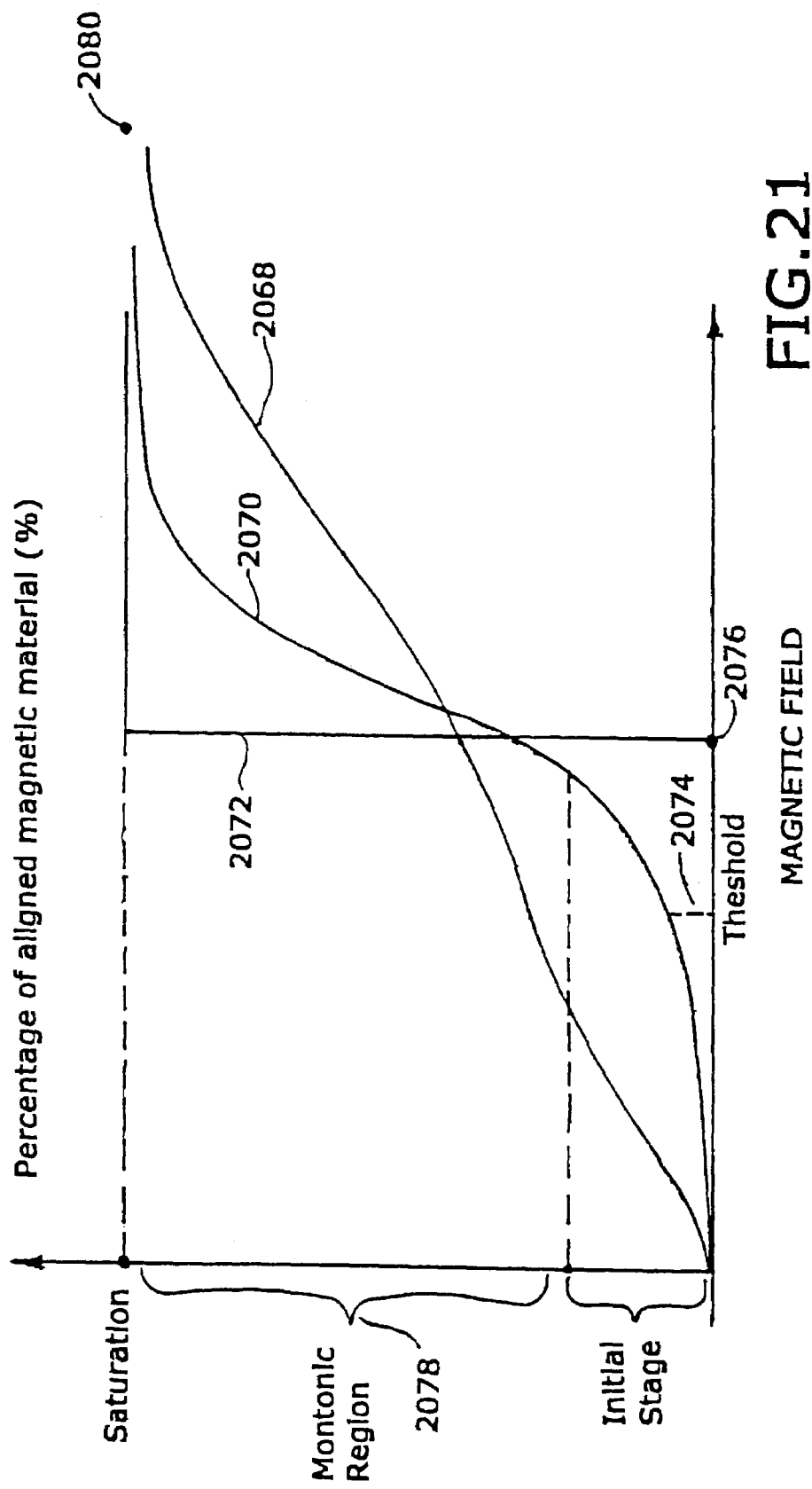
FIG. 21 is a graph showing the relationship of the alignment of the nanomagnetic liquid crystal material of FIGS. 20A and 20B with magnetic field strength.

FIG. 21 is a graph of the response of a typical matrix 2032 comprised of nanomagnetic liquid crystals. Three different curves, curves 2068, 2070, and 2072, are depicted, and they correspond to the responses of three different nanomagnetic liquid crystal materials have different shapes and/or sizes and/or compositions.

Referring to FIG. 21, and for each of curves 2068 through 2072, it will be seen that there is often a threshold point 2074 below which no meaningful response to the applied magnetic field is seen; see, e.g., the response for curve 2070.

It should be noted, however, that some materials have a low threshold before they start to exhibit response to the applied magnetic field; see, e.g., curve 2068. On the other hand, some materials have a very large threshold; see, e.g., threshold 2076 for curve 2072.

One may produce any desired response curve by the proper combination of nanomagnetic material composition, concentration, and location as well as liquid crystal geometries, materials, and sizes. Other such variables will be apparent to those skilled in the art.

Referring again to FIG. 21, it will be seen that there often is a monotonic region 2078 in which the increase of alignment of the nanomagnetic material is monotonic and often directly proportional; see, e.g., curve 2070.

There also is often a saturation point 2080 beyond which an increase in the applied magnetic field does not substantially increase the alignment.

As will be seen from the curves in FIG. 21, the process often is reversible. One may go from a higher level of alignment to a lower level by reducing the magnetic field applied.

Figure 22:
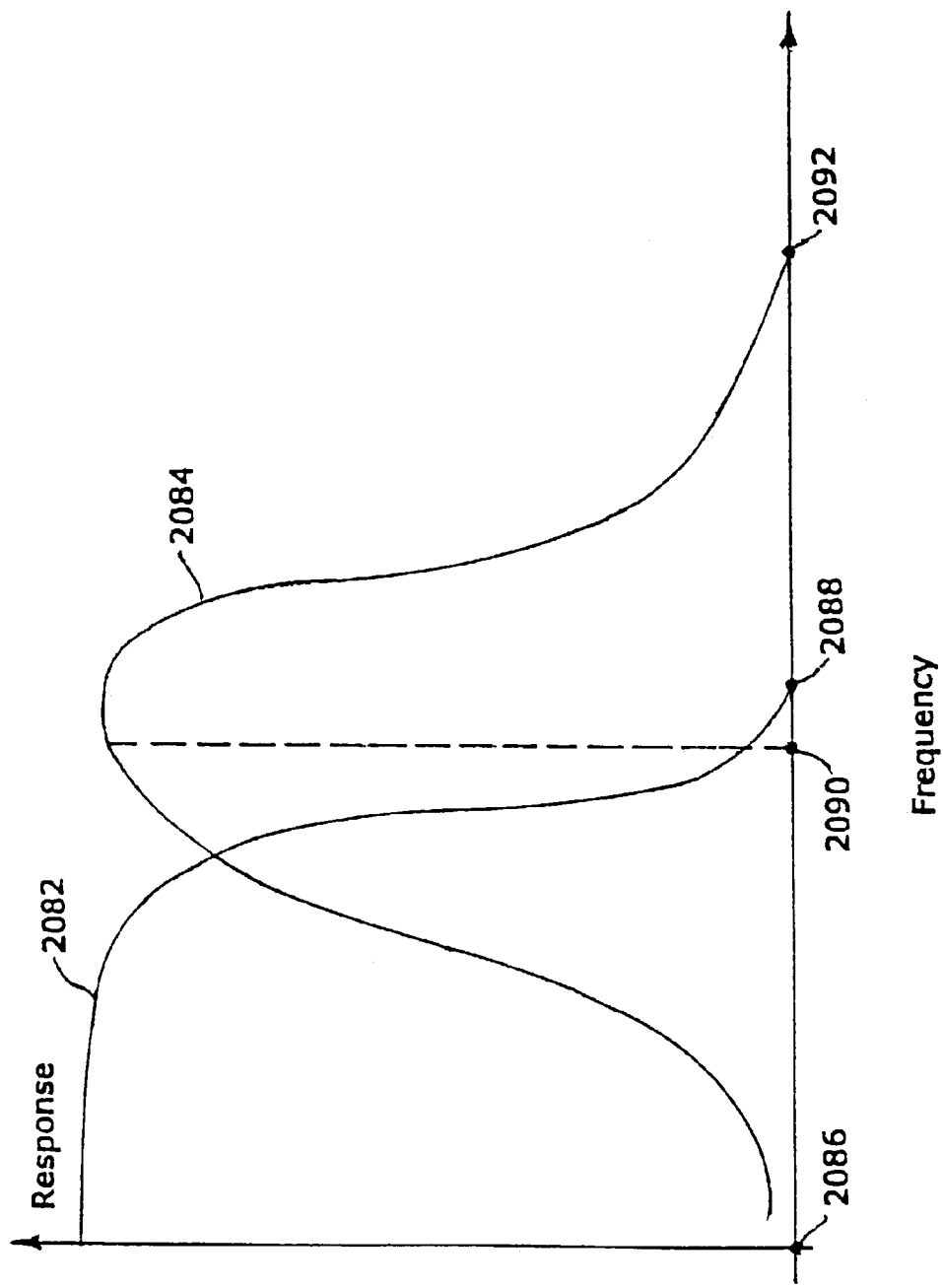
FIG. 22 is a graph showing the relationship of the attenuation provided by the shielding device of this invention as a function of frequency of the applied magnetic field.

The frequency of the magnetic field applied also influences the degree of alignment. As is illustrated in FIG. 22, for one nanomagnetic liquid crystal material (curve 2082), the response is at a maximum at an initial frequency 2086 but then decreases to a minimum at frequency 2088. By comparison, for another such curve (curve 2090), the response is minimum at frequency 1086, increases to a maximum at point 2098, and then decreases to a minimum at point 2092.

Thus, one may influence the response of a particular nanomagnetic liquid crystal material by varying its type of nanomagnetic material, and/or its concentration, and/or its shape, and/or the frequency to which it is subjected. Referring again to FIG. 19A, one may affect the shielding effectiveness of shield 2002 by supplying a secondary magnetic field (from controller 2007) at the secondary frequencies which will elicit the desired shielding effect.

Figure 23:
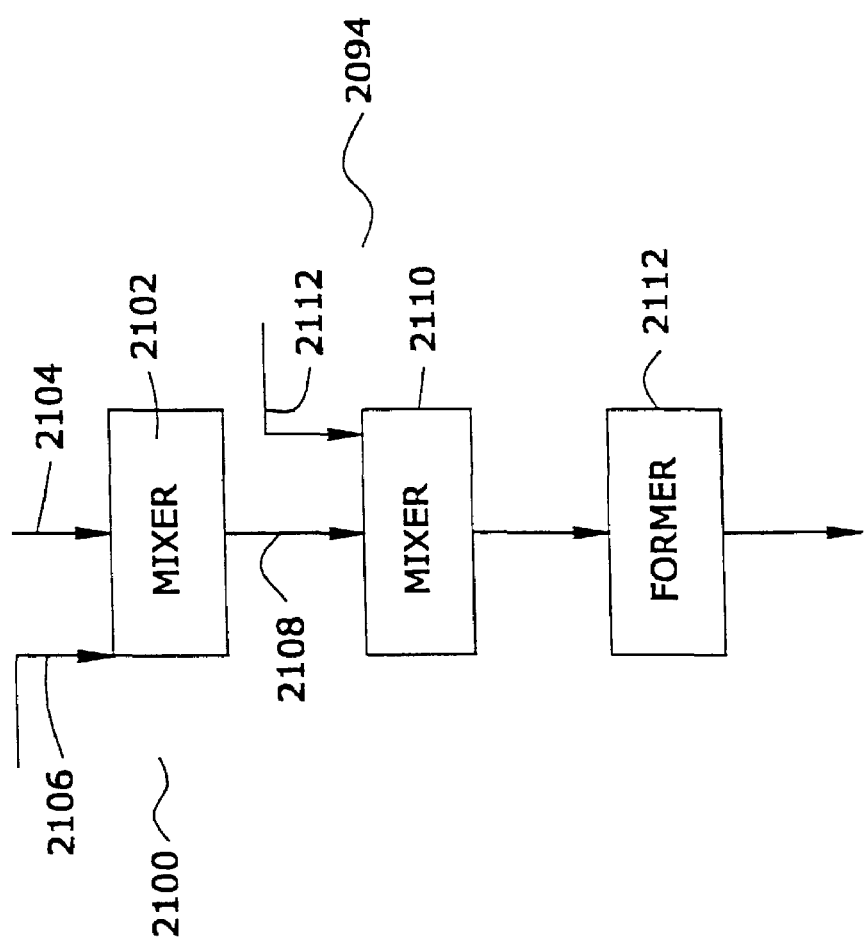
FIG. 23 is a flow diagram of one preferred process for preparing the nanomagnetic liquid crystal compositions of this invention.

FIG. 23 is a flow diagram illustrating a preferred process 2094 for making nanomagnetic liquid crystal material.

Referring to FIG. 23, and in step 2100, the nanomagnetic material of this invention is charged to a mixer 2102 via line 2104. Thereafter, suspending medium is also charged to the mixer 2102 via line 2106.

The suspending medium may be any medium in which the nanomagnetic material is dispersible. Thus, e.g., the suspending medium may be a gel, it may be an aqueous solution, it may be an organic solvent, and the like. In one embodiment, the nanomagnetic material is not soluble in the suspending medium; in this embodiment, a slurry is produced. For the sake of simplicity of description, the use of a polymer will be described in the rest of the process.

Referring again to FIG. 23, the slurry from mixer 2102 is charged via line 2108 to mixer 2110. Thereafter, or simultaneously, polymeric precursor of liquid crystal material is also charged to mixer 2108 via line 2112.

As is known to those skilled in the art, aromatic polyesters (liquid crystals) may b used as such polymeric precursor. These aromatic polyesters are commercially available as, e.g., Vectra (sold by Hoechst Celanese Engineering Plastic), Xydur (sold by Amoco Performance Plastics), Granlar (sold by Granmont), and the like. Reference may be had, e.g., to pages 649–650 of the aforementioned "Materials Handbook." Reference also may be had, e.g., to U.S. Pat. Nos. 4,738,880, 5,142,017, 5,006,402, 4,935,833, and the like. The entire disclosure of each of these United States patents is hereby incorporated by reference into this specification.

Referring again to FIG. 23, the liquid crystal polymer is mixed with the nanomagnetic particles for a time sufficient to produce a substantially homogeneous mixture. Typically, mixing occurs from about 5 to about 60 minutes.

The polymeric material formed in mixer 2110 then is formed into a desired shape in former 2112. Thus, and referring to Joel Frados' "Plastics Engineering Handbook," Fourth Edition (Van Nostrand Reinhold Company, New York, N.Y., 1976), one may form the desired shape by injection molding, extrusion, compression and transfer molding, cold molding, blow molding, rotational molding, casting, machining, joining, and the like. Other such forming procedures are well known to those skilled in the art.

One may prepare several different nanomagnetic structures and join them together to form a composite structure. One such composite structure is illustrated in FIG. 24.

Figure 24:
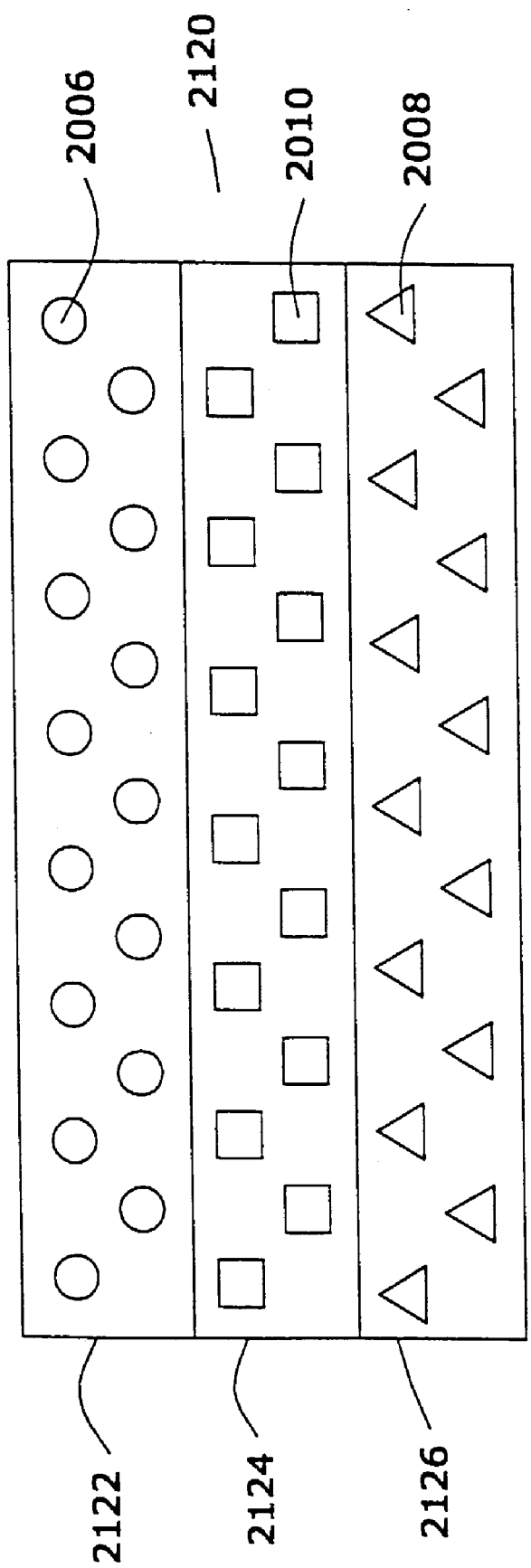
FIG. 24 is a sectional view of a multiplayer structure comprised of different nanomagnetic materials.

Referring to FIG. 24, assembly 2120 is comprised of nanomagnetic particles 2006, 2010, and 2008 disposed in layers 2122, 2124, and 2126, respectively. In the embodiment depicted, the layers 2122, 2124, and 2126 are contiguous with each, thereby forming a continuous assembly of nanomagnetic material, with different concentrations and compositions thereof at different points. The response of assembly 2120 to any particular magnetic field will vary depending upon the location at which such response is measured.

Figure 25:
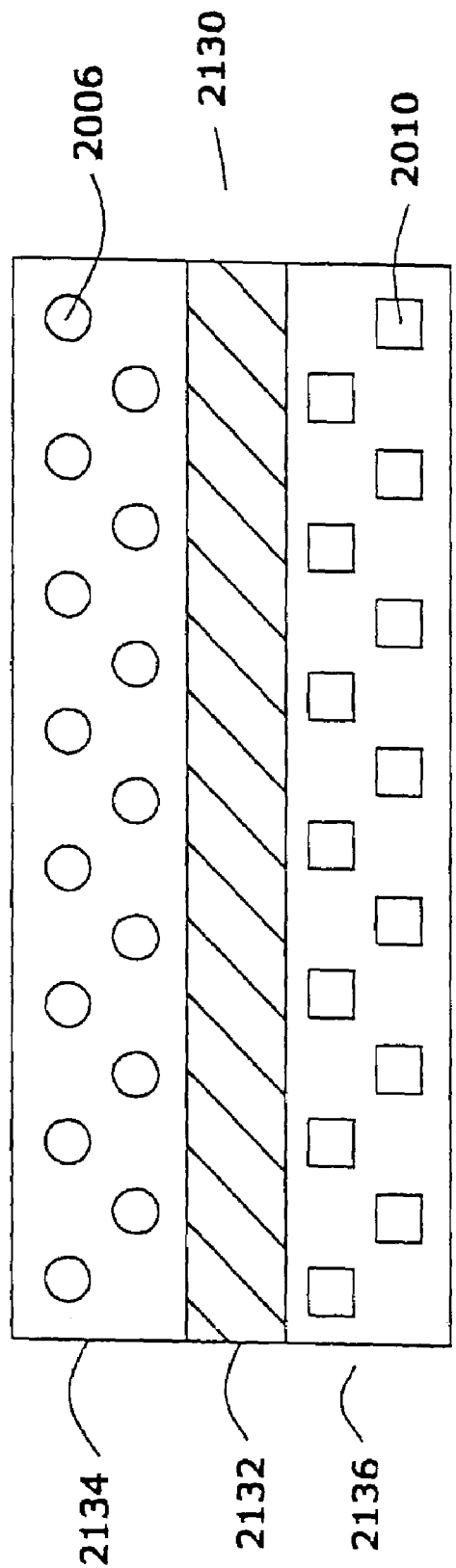
FIG. 25 is a sectional view of another multilayer structure comprised of different nanomagnetic materials and an electrical insulating layer.

FIG. 25 illustrates an assembly 2130 that is similar to assembly 2120 but that contains an insulating layer 2132 disposed between nanomagnetic layers 2134 and 2136.

The assembly 2130

The insulating layer 2132 may be either electrically insulative and/or thermally insulative.

Figure 26:
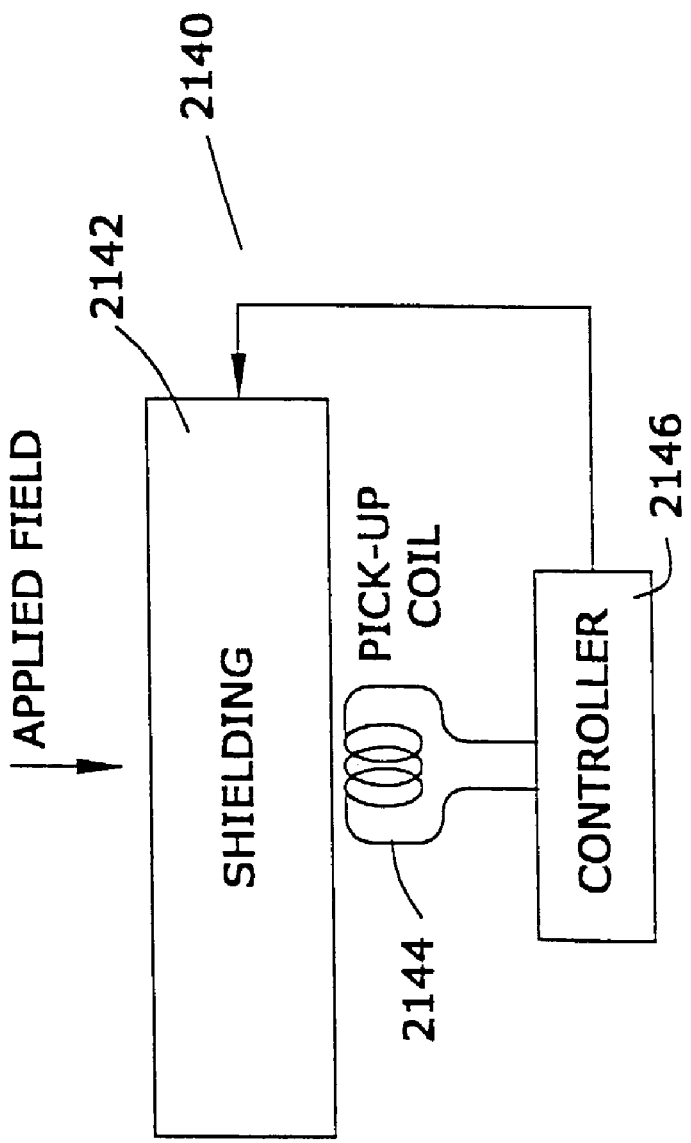
FIG. 26 is a schematic view of yet another multilayer structure comprised of nanomagnetic material.

FIG. 26 illustrates an assembly 2140 in which the response of nanomagnetic material 2142 is sensed by sensor 2144 that, in the embodiment depicted, is a pickup coil 2144. Data from sensor 2144 is transmitted to controller 2146. When and as appropriate, controller 2146 may introduce electrical and/or magnetic energy into shielding material 2142 in order to modify its response.

Figure 27:
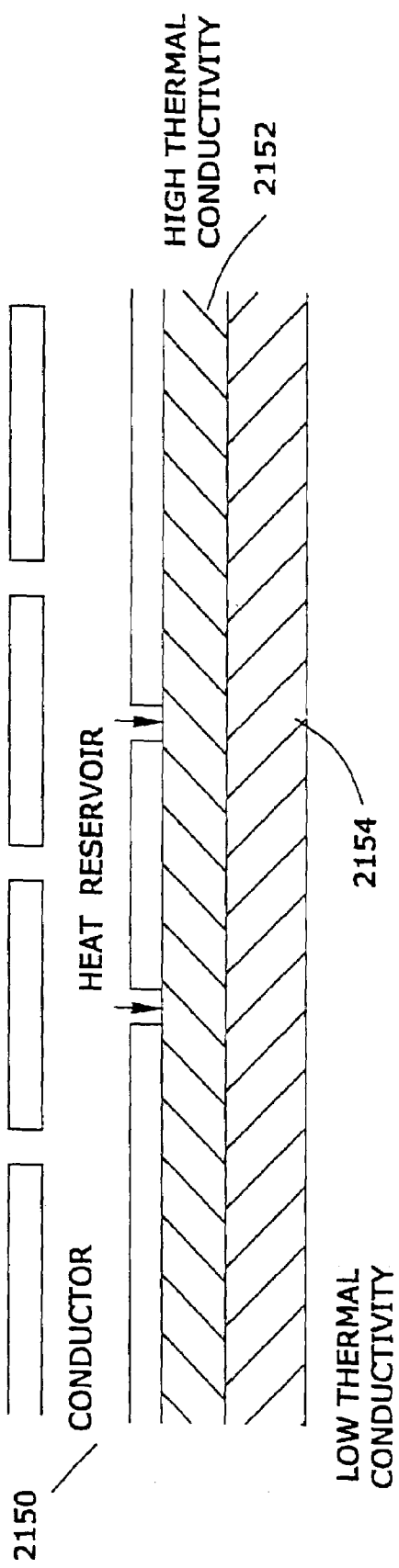
FIG. 27 is a schematic of yet another multilayer structure comprised of nanomagnetic material.

FIG. 27 is a schematic illustration of an assembly 2150. In the embodiment depicted, concentric insulating layers 2152 and 2154 preferably have substantially different thermal conductivities. Layer 2152 preferably has a thermal conductivity that is in the range of from about 10 to about 2000 calories per hour per square centimeter per centimeter per degree Celsius. Layer 2154 has a thermal conductivity that is in the range of from about 0.2 to about 10 calories per hour per square centimeter per centimeter per degree Celsius. Layers 2152 and 2154 are designed by choice of thermal conductivity and of layer thickness such that heat is conducted axially along, and circumferentially around, layer 2152 at a rate that is between 10 times and 1000 times higher than in layer 2154. Thus, in this embodiment, any heat that is generated at any particular site or sites in one or more nanomagnetic shielding layers will be distributed axially along the shielded element, and circumferentially around it, before being conducted radially to adjoining tissues. This will serve to further protect these adjoining tissues from thermogenic damage even if there are minor local flaws in the nanomagnetic shield.

Thus, in one embodiment of the invention, there is described a magnetically shielded conductor assembly, that contains a conductor, at least one layer of nanomagnetic material, a first thermally insulating layer, and a second thermally insulating layer. The first thermal insulating layer resides radially inward from said second thermally insulating layer, and it has a thermal conductivity from about 10 to about 2000 calories-centimeter per hour per square centimeter per degree Celsius The second thermal insulating layer has a thermal conductivity from about 0.2 to about 10 calories per hour per square centimeter per degree Celsius, and the axial and circumferential heat conductance of the first thermal insulating layer is at least about 10 to about 1000 times higher than it is for said second thermal insulating layer.

In another embodiment of the invention, there is provided a magnetically shielded conductor assembly as discussed hereinabove, in which the first thermally insulating layer is disposed between said conductor and said layer of nanomagnetic material, and the second thermally insulating layer is disposed outside said layer of nanomagnetic material.

In another embodiment, there is provided a magnetically shielded conductor assembly as discussed hereinabove wherein the first thermally insulating layer is disposed outside the layer of nanomagnetic material, and wherein the second thermally insulating layer is disposed outside said first layer of thermally insulating material.

Figure 28:
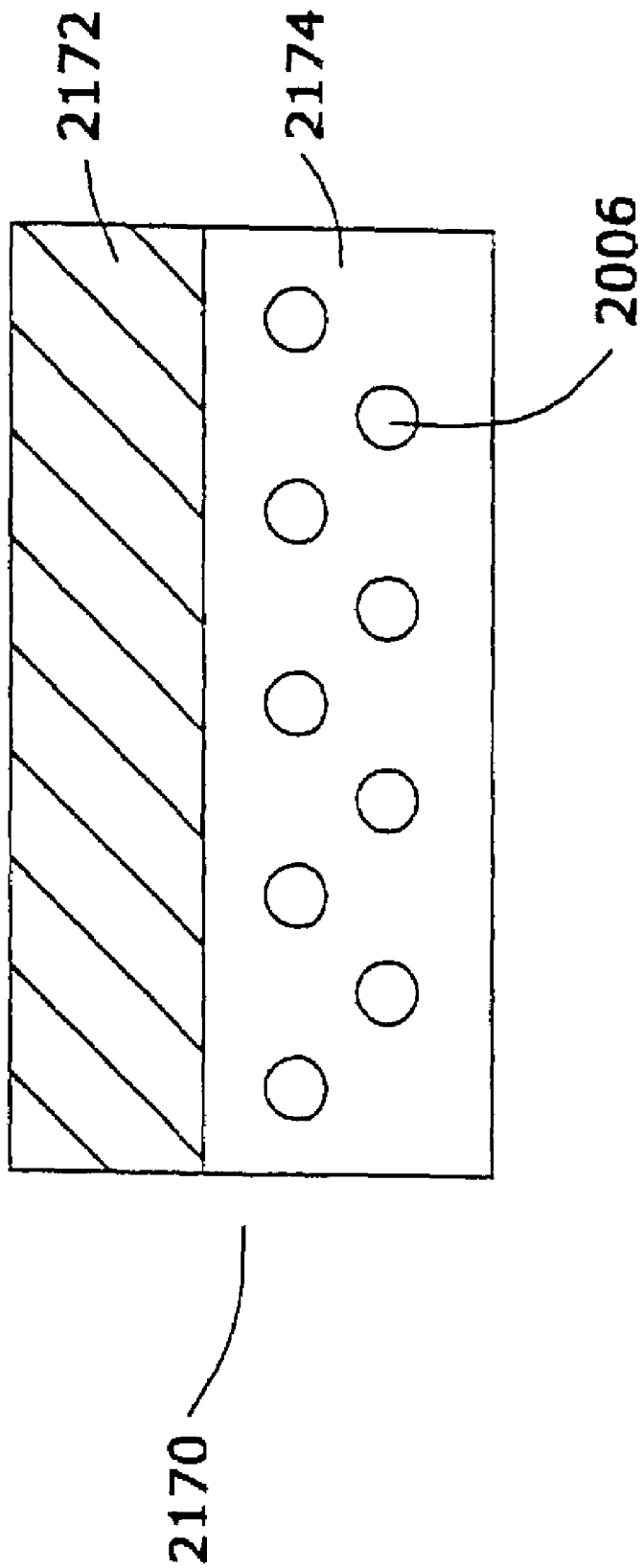
FIG. 28 is a schematic of yet another multilayer structure comprised of nanomagnetic material.

In another embodiment, the shield is comprised of a abrasion-resistant coating comprised of nanomagnetic material. Referring to FIG. 28, it will be seen that shield 2170 is comprised of abrasion resistant coating 2172 and nanomagnetic layer 2174.

A Composite Shield

In this portion of the specification, applicants will describe one embodiment of a composite shield of their invention This embodiment involves a shielded assembly comprised of a substrate and, disposed above a substrate, a shield comprising from about 1 to about 99 weight percent of a first nanomagnetic material, and from about 99 to about 1 weight percent of a second material with a resistivity of from about 1 microohm-centimeter to about $1 \times 10^{25}$ microohm centimeters.

Figure 29:
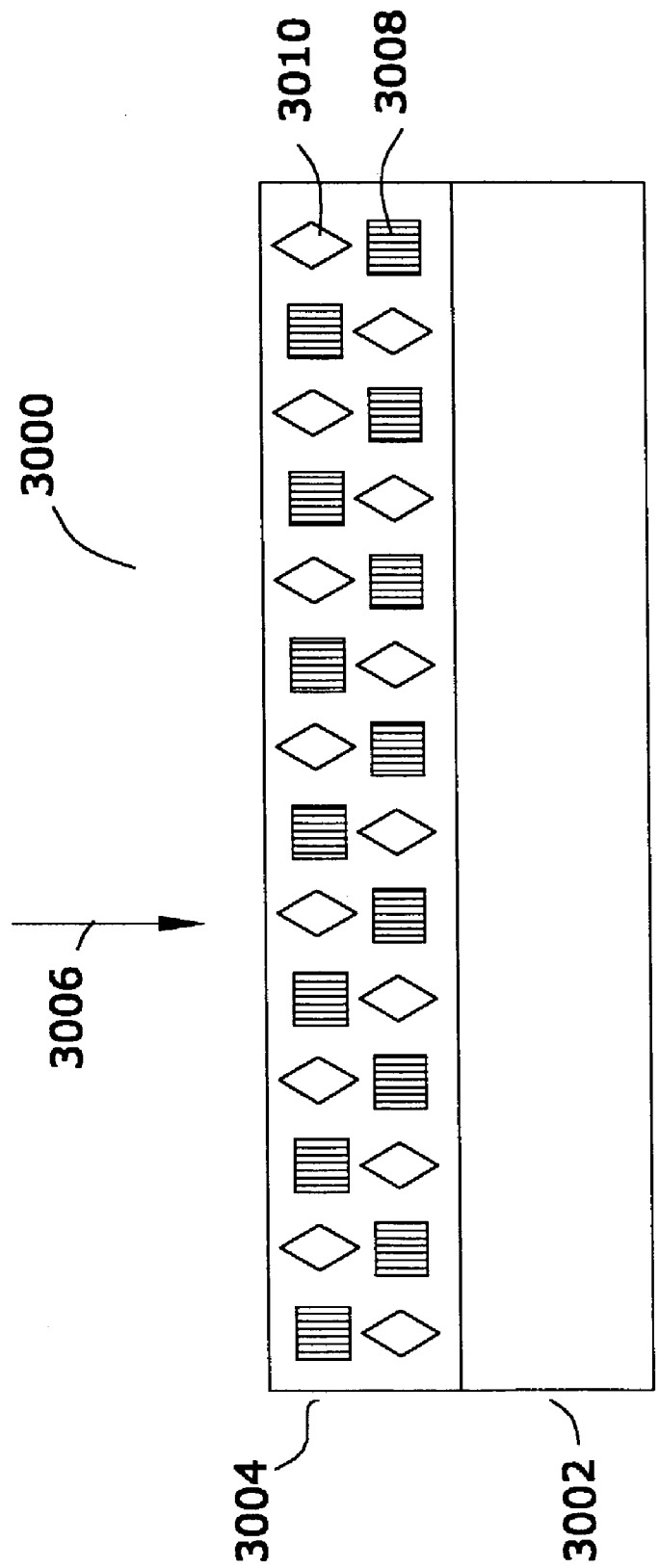
FIGS. 29, 30, and 31 are also schematics of other multiplayer structures comprised of nanomagnetic material.

FIG. 29 is a schematic of a preferred shielded assembly 3000 that is comprised of a substrate 3002. The substrate 3002 may be any one of the substrates illustrated hereinabove. Alternatively, or additionally, it may be any receiving surface which it is desired to shield from magnetic and/or electrical fields. Thus, e.g., the substrate can be substantially any size, any shape, any material, or any combination of materials. The shielding material(s) disposed on and/or in such substrate may be disposed on and/or in some or all of such substrate.

By way of illustration and not limitation, the substrate 3002 may be, e.g., a foil comprised of metallic material and/or polymeric material. The substrate 3002 may, e.g., comprise ceramic material, glass material, composites, etc. The substrate 3002 may be in the shape of a cylinder, a sphere, a wire, a rectilinear shaped device (such as a box), an irregularly shaped device, etc.

In one embodiment, the substrate 3002 preferably a thickness of from about 100 nanometers to about 2 centimeters. In one aspect of this embodiment, the substrate 3002 preferably is flexible.

Referring again to FIG. 29, and in the preferred embodiment depicted therein, it will be seen that a shield 3004 is disposed above the substrate 3002. As used herein, the term "above" refers to a shield that is disposed between a source 3006 of electromagnetic radiation and the substrate 3002.

The shield 3004 is comprised of from about 1 to about 99 weight percent of nanomagnetic material 3008; such nanomagnetic material, and its properties, are described elsewhere in this specification. In one embodiment, the shield 3004 is comprised of at least about 40 weight percent of such nanomagnetic material 3008. In another embodiment, the shield 3004 is comprised of at least about 50 weight percent of such nanomagnetic material 3008.

Referring again to FIG. 29, and in the preferred embodiment depicted therein, it will be seen that the shield 3004 is also comprised of another material 3010 that preferably has an electrical resistivity of from about about 1 microohm-centimeter to about $1 \times 10^{25}$ microohm-centimeters. This material 3010 is preferably present in the shield at a concentration of from about 1 to about 1 to about 99 weight percent and, more preferably, from about 40 to about 60 weight percent.

In one embodiment, the material 3010 has a dielectric constant of from about 1 to about 50 and, more preferably, from about 1.1 to about 10. In another embodiment, the material 3010 has resistivity of from about 3 to about 20 microohm-centimeters.

In one embodiment, the material 3010 preferably is a nanoelectrical material with a particle size of from about 5 nanometers to about 100 nanometers.

In another embodiment, the material 3010 has an elongated shape with an aspect ratio (its length divided by its width) of at least about 10. In one aspect of this embodiment, the material 3010 is comprised of a multiplicity of aligned filaments.

In one embodiment, the material 3010 is comprised of one or more of the compositions of U.S. Pat. Nos. 5,827,997 and 5,643,670.

Thus, e.g., the material 3010 may comprise filaments, wherein each filament comprises a metal and an essentially coaxial core, each filament having a diameter less than about 6 microns, each core comprising essentially carbon, such that the incorporation of 7 percent volume of this material in a matrix that is incapable of electromagnetic interference shielding results in a composite that is substantially equal to copper in electromagnetic interference shielding effectives at 1–2 gigahertz. Reference may be had, e.g., to U.S. Pat. No. 5,827,997, the entire disclosure of which is hereby incorporated by reference into this specification.

In another embodiment, the material 3010 is a particulate carbon complex comprising: a carbon black substrate, and a plurality of carbon filaments each having a first end attached to said carbon black substrate and a second end distal from said carbon black substrate, wherein said particulate carbon complex transfers electrical current at a density of 7000 to 8000 milliamperes per square centimeter for a $Fe^{+2}/Fe^{+3}$ oxidation/reduction electrochemical reaction couple carried out in an aqueous electrolyte solution containing 6 millmoles of potassium ferrocyanide and one mole of aqueous potassium nitrate.

In another embodiment, the material 3010 may be a diamond-like carbon material. As is known to those skilled in the art, this diamond-like carbon material has a Mohs hardness of from about 2 to about 15 and, preferably, from about 5 to about 15. Reference may be had, e.g., to U.S. Pat. No. 5,098,737 (amorphic diamond material), U.S. Pat. No. 5,658,470 (diamond-like carbon for ion milling magnetic material), U.S. Pat. No. 5,731,045 (application of diamond-like carbon coatings to tungsten carbide components), U.S. Pat. No. 6,037,016 (capacitively coupled radio frequency diamond-like carbon reactor), U.S. Pat. No. 6,087,025 (application of diamond like material to cutting surfaces), and the like. The entire disclosure of each of these United States patents is hereby incorporated by reference into this specification.

In another embodiment, material 3010 is a carbon nanotube material. These carbon nanotubes generally have a cylindrical shape with a diameter of from about 2 nanometers to about 100 nanometers, and length of from about 1 micron to about 100 microns.

These carbon nanotubes are well known to those skilled in the art. Reference may be had, e.g., to U.S. Pat. No. 6,203,864 (heterojunction comprised of a carbon nanotube), U.S. Pat. No. 6,361,861 (carbon nanotubes on a substrate), U.S. Pat. No. 6,445,006 (microelectronic device comprising carbon nanotube components), U.S. Pat. No. 6,457,350 (carbon nanotube probe tip), and the like. The entire disclosure of each of these United States patents is hereby incorporated by reference into this specification.

In one embodiment, material 3010 is silicon dioxide particulate matter with a particle size of from about 10 nanometers to about 100 nanometers.

In another embodiment, the material 3010 is particulate alumina, with a particle size of from about 10 to about 100 nanometers. Alternatively, or additionally, one may use aluminum nitride particles, cerium oxide particles, yttrium oxide particles, combinations thereof, and the like; regardless of the particle(s) used, it is preferred that its particle size be from about 10 to about 100 nanometers.

In the embodiment depicted in FIG. 29, the shield 3004 is in the form of a layer of material that has a thickness of from about 100 nanometers to about 10 microns. In this embodiment, both the nanomagnentic particles 3008 and the electrical particles 3010 are present in the same layer.

Figure 30:
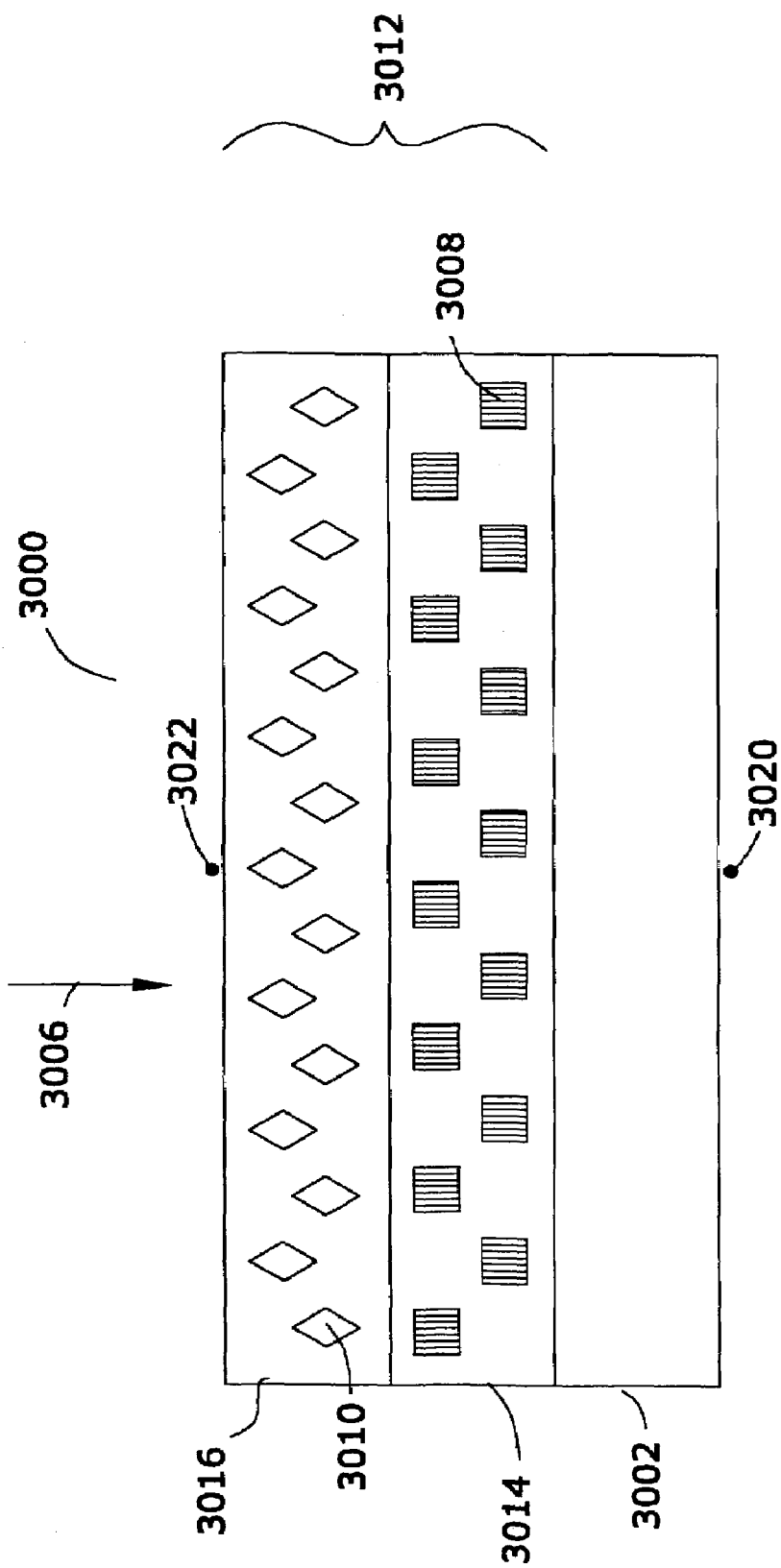

In the embodiment depicted in FIG. 30, by comparison, the shield 3012 is comprised of layers 3014 and 3016. The layer 3014 is comprised of at least about 50 weight percent of nanomagnetic material 3008 and, preferably, at least about 90 weight percent of such nanomagnetic material 3008. The layer 3016 is comprised of at least about 50 weight percent of electrical material 3010 and, preferably, at least about 90 weight percent of such electrical material 3010.

In the embodiment depicted in FIG. 30, the layer 3014 is disposed between the substrate 3002 and the layer 3016. In the embodiment depicted in FIG. 31, the layer 3016 is disposed between the substrate 3002 and the layer 3014.

Each of the layers 3014 and 3016 preferably has a thickness of from about 10 nanometers to about 5 microns.

In one embodiment, the shield 3012 has an electromagnetic shielding factor of at least about 0.5 and, more preferably, at least about 0.9. In one embodiment, the electromagnetic field strength at point 3020 is no greater than about 10 percent of the electromagnetic field strength at point 3022.

Figure 31:
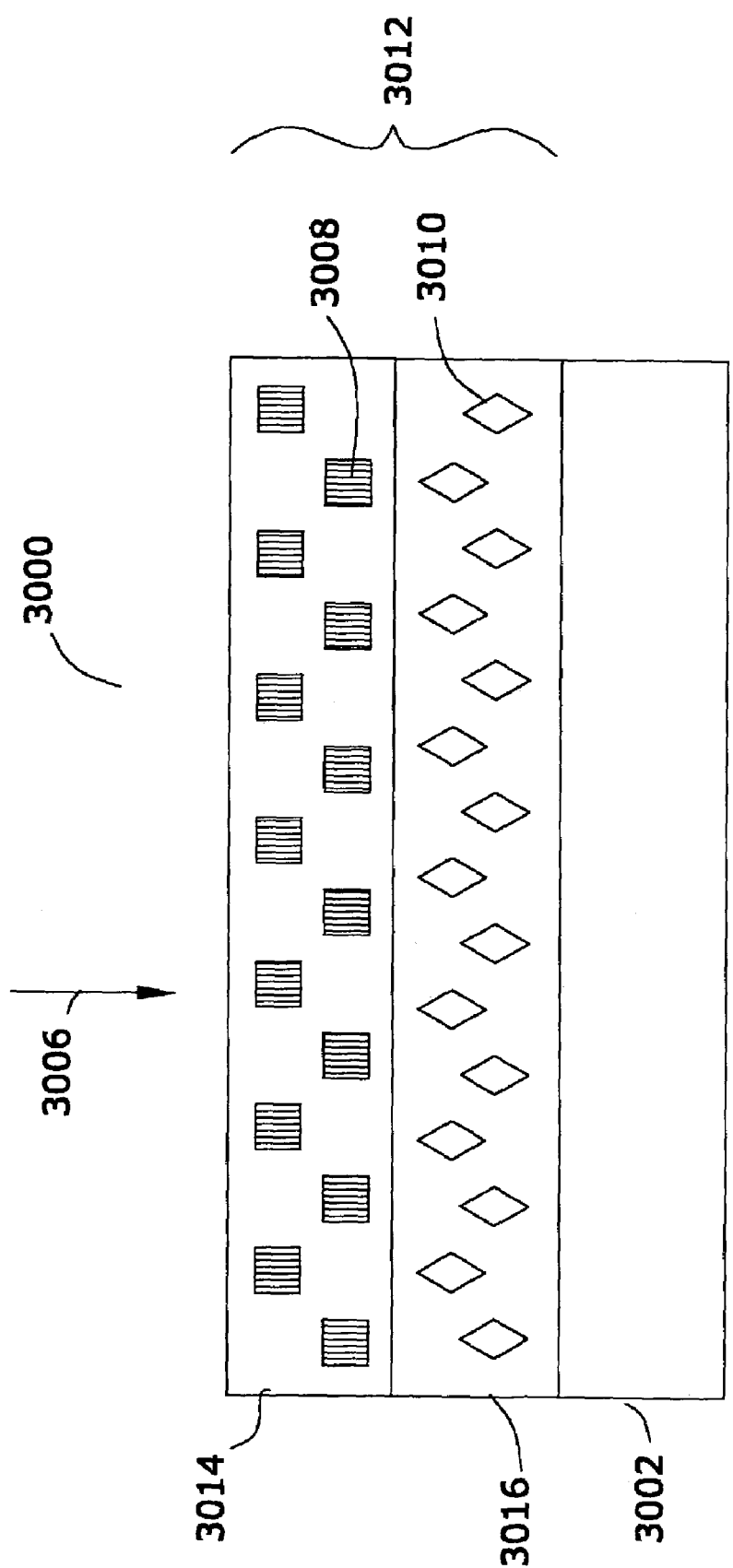

In one preferred embodiment, illustrated in FIG. 31, the nanomagnetic material preferably has a mass density of at least about 0.01 grams per cubic centimeter, a saturation magnetization of from about 1 to about 36,000 Gauss, a coercive force of from about 0.01 to about 5000 Oersteds, a relative magnetic permeability of from about 1 to about 500,000, and an average particle size of less than about 100 nanometers.

Determination of the Heat Shielding Effect of the Magnetic Shield

Figure 32:
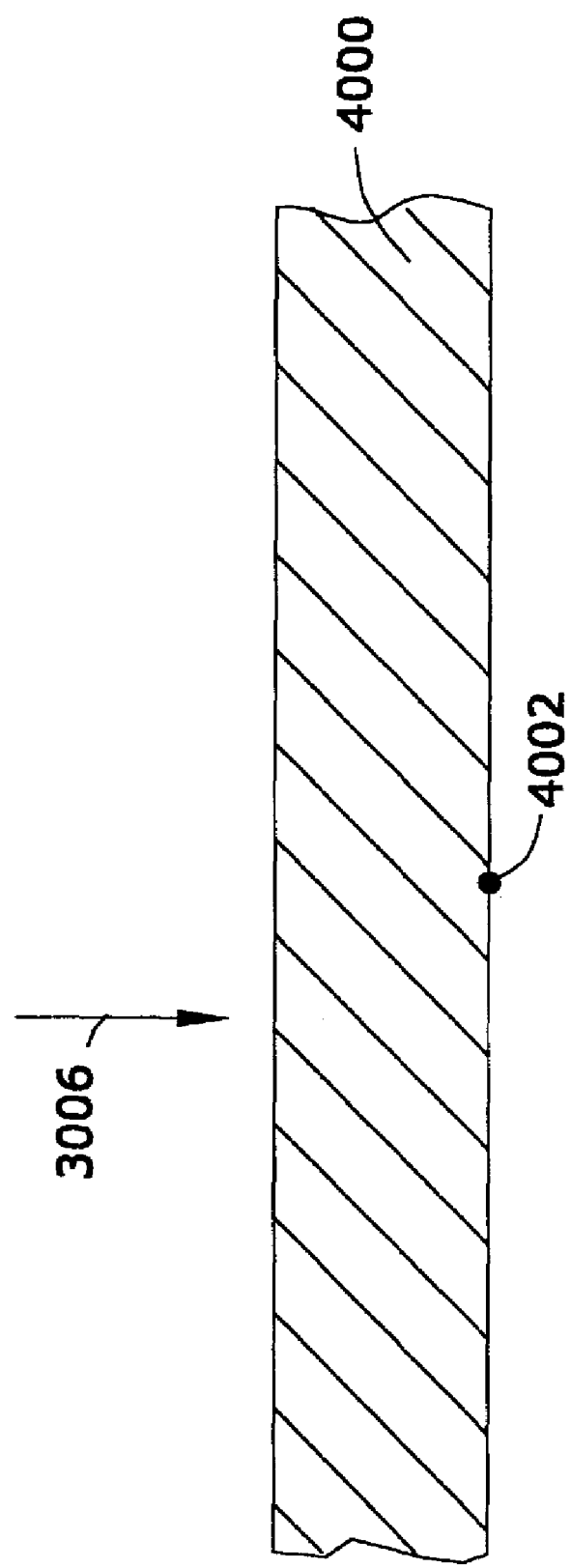
FIG. 32 is a schematic illustration of a means for determining the extent to which the temperature rises in a conductor when exposed to a strong magnetic field.

FIG. 32 is a schematic representation of a test which may be used to determine the extent to which the temperature of a conductor 4000 is raised by exposure to strong electromagnetic radiation 3006. In this test, the radiation 3006 is representative of the fields present during MRI procedures. As is known to those skilled in the art, such fields typically include a static field with a strength of from about 0.5 to about 2 Teslas, a radio frequency alternating magnetic field with a strength of from about 20 microTeslas to about 100 microTeslas, and a gradient magnetic field that has three components—x, y, and z, each of which has a field strength of from about 0.05 to 500 milliTeslas.

The test depicted in FIG. 32 is conducted in accordance with A.S.T.M. Standard Test F-2182-02, "Standard test method for measurement of radio-frequency induced heating near passive implant during magnetic resonance imaging." Referring again to FIG. 32, a temperature probe 4002 is used to measure the temperature of an unshielded conductor 4000 when subjected to the magnetic field 3006 in accordance with such A.S.T.M. F-2182-02.

The same test is then is then performed upon a shielded conductor assembly 4010 that is comprised of the conductor 4000 and a magnetic shield 4004.

The magnetic shield used may comprise nanomagnetic particles, as described hereinabove. Alternatively, or additionally, it may comprise other shielding material, such as, e.g., oriented nanotubes (see, e.g., U.S. Pat. No. 6,265,466).

In the embodiment depicted, the shield 4004 is in the form of a layer of shielding material with a thickness 4006 of from about 10 nanometers to about 1 millimeter. In one embodiment, the thickness 4006 is from about 10 nanometers to about 20 microns.

Figure 33:
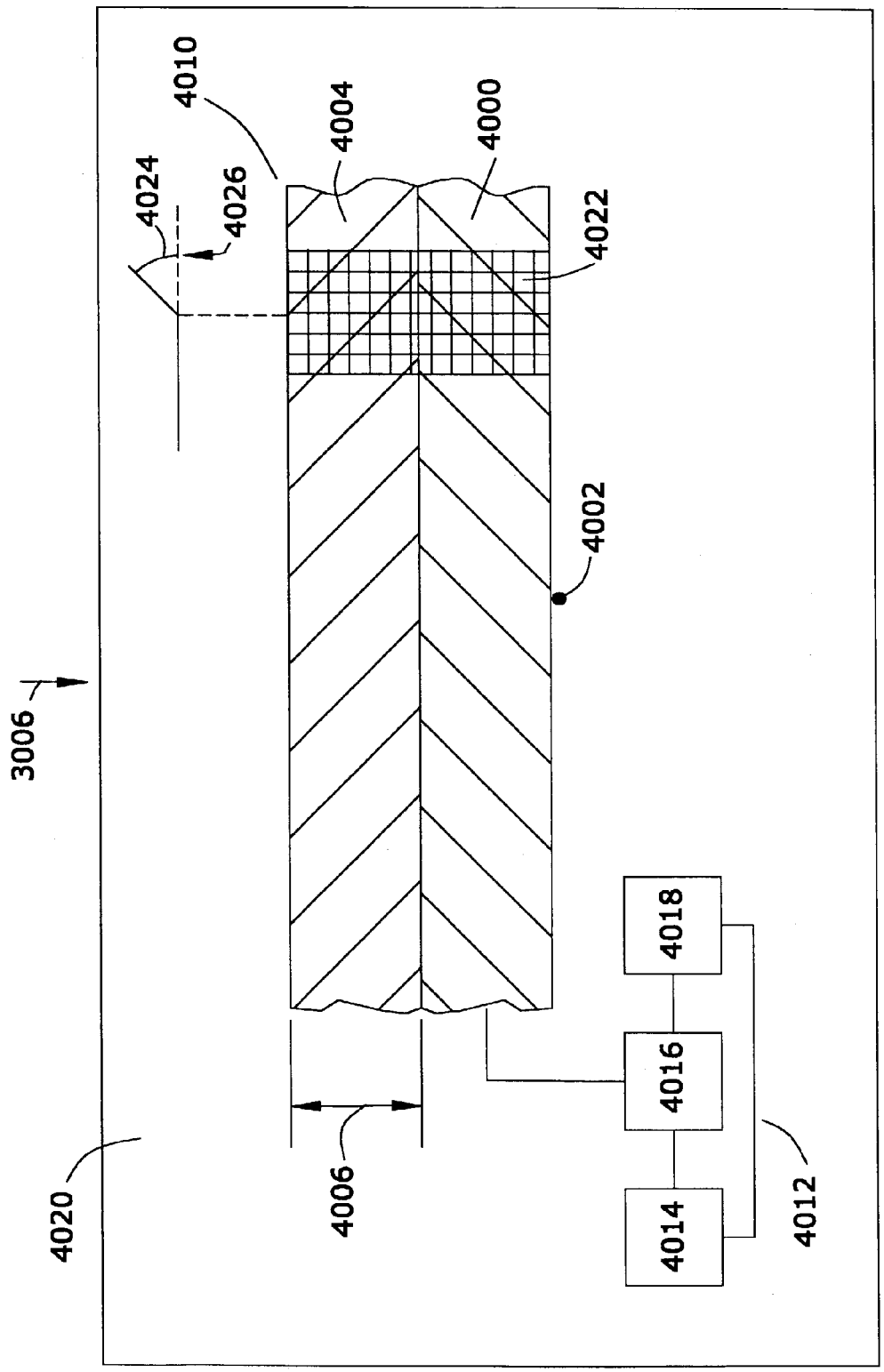
FIG. 33 is a schematic illustration of a means for determining the extent to which the temperature rises in a magnetically shielded inductor when exposed to a strong magnetic field.

In one preferred embodiment, illustrated in FIG. 33, the shielded conductor 4010 is implantable device and is connected to a pacemaker assembly 4012. comprised of a power source 4014, a pulse generator 4016, and a controller 4018. The pacemaker assembly 4012 and its associated shielded conductor 4010 are preferably disposed within a living biological organism 4020. F-2182-02, it is preferably tested ex vivo.

Referring again to FIG. 33, and in the preferred embodiment depicted therein, it will be seen that shielded conductor assembly 4010 comprises means for transmitting signals to and from the pacemaker 4012 and the biological organism 4020.

In one preferred embodiment, the conductor 4000 is flexible, that is, at least a portion 4022 of the conductor 4000 is capable of being flexed at an angle 4024 of least 15 degrees by the application of a force 4026 not to exceed about 1 dyne.

Figure 34:
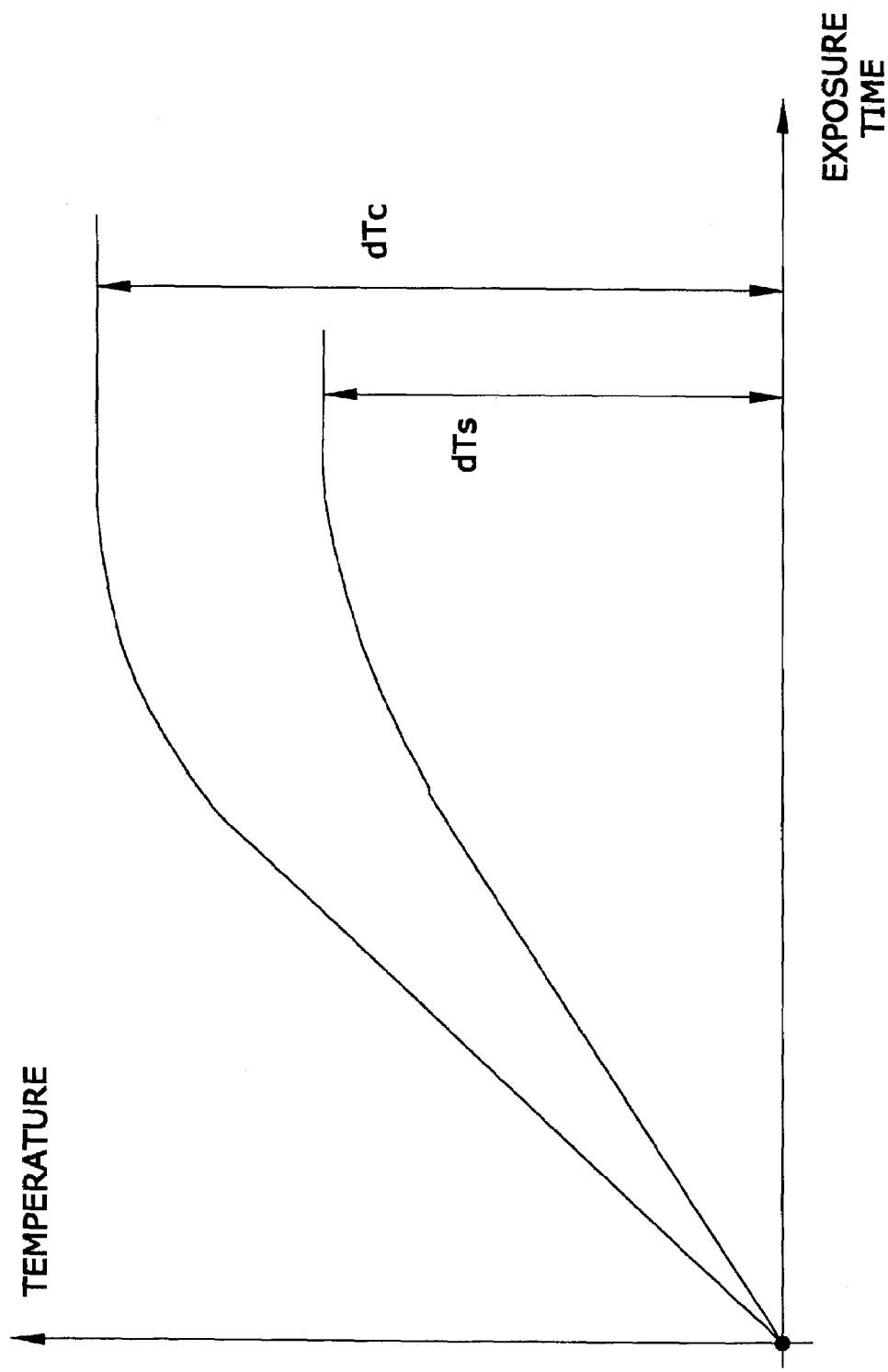
FIG. 34 is a graph showing the relationship of the temperature differentials in a shielded conductor and a non conductor when each of them are exposed to the same strong magnetic field.

Referring again to FIG. 33, when the shielded assembly is tested in accordance with A.S.T.M. 2182-02, it will have a specified temperature increase, as is illustrated in FIG. 34.

As is shown in FIG. 34, the "dTs" is the change in temperature of the shielded assembly 4010 when tested in accordance with such A.S.T.M. test. The "dTc" is the change in temperature of the unshielded conductor 4000 using precisely the same test conditions but omitting the shield 4004. The ratio of dTs/dTc is the temperature increase ratio; and 1–the temperature increase ratio is defined as the heat shielding factor.

It is preferred that the shielded conductor assembly 4010 have a heat shielding factor of at least about 0.2. In one embodiment, the shielded conductor assembly 4010 has a heat shielding factor of at least 0.3.

Figure 36:
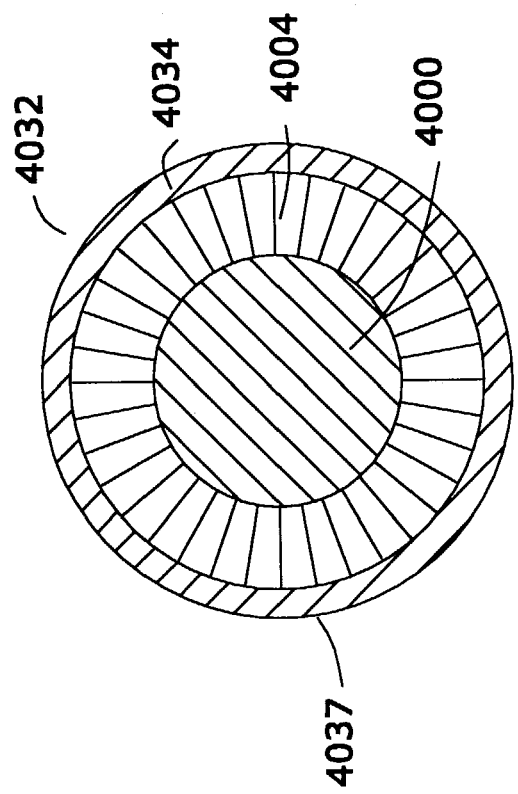
FIG. 36 is a schematic of another preferred magnetic shield assembly of the invention.
Figure 35:
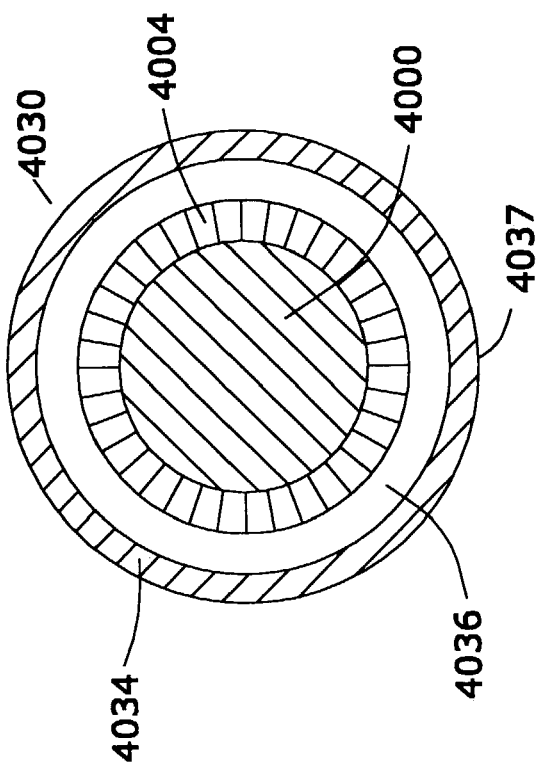
FIG. 35 is a schematic of one preferred magnetic shield assembly of the invention.

FIGS. 35 and 36 are sectional views of shielded conductor assembly 4030 and 4032. Each of these assemblies is comprised of a flexible conductor 4000, a layer 4004 of magnetic shielding material, and a sheath 4034.

The sheath 4034 preferably is comprised of antithombogenic material. In one embodiment, the sheath 4034 preferably has a coefficient of friction of less than about 0.1.

Antithrombogenic compositions and structures have been well known to those skilled in the art for many years. As is disclosed, e.g., in U.S. Pat. No. 5,783,570, the entire disclosure of which is hereby incorporated by reference into this specification, "Artificial materials superior in processability, elasticity and flexibility have been widely used as medical materials in recent years. It is expected that they will be increasingly used in a wider area as artificial organs such as artificial kidney, artificial lung, extracorporeal circulation devices and artificial blood vessels, as well as disposable products such as syringes, blood bags, cardiac catheters and the like. These medical materials are required to have, in addition to sufficient mechanical strength and durability, biological safety which particularly means the absence of blood coagulation upon contact with blood, i.e., antithrombogenicity.

Conventionally employed methods for imparting antithrombogenicity to medical materials are generally classified into three groups of (1) immobilizing a mucopolysaccharide (e.g., heparin) or a plasminogen activator (e.g., urokinase) on the surface of a material, (2) modifying the surface of a material so that it carries negative charge or hydrophilicity, and (3) inactivating the surface of a material. Of these, the method of (1) (hereinafter to be referred to briefly as surface heparin method) is further subdivided into the methods of (A) blending of a polymer and an organic solvent-soluble heparin, (B) coating of the material surface with an organic solvent-soluble heparin, (C) ionical bonding of heparin to a cationic group in the material, and (D) covalent bonding of a material and heparin.

Of the above methods, the methods (2) and (3) are capable of affording a stable antithrombogenicity during a long-term contact with body fluids, since protein adsorbs onto the surface of a material to form a biomembrane-like surface. At the initial stage when the material has been introduced into the body (blood contact site) and when various coagulation factors etc. in the body have been activated, however, it is difficult to achieve sufficient antithrombogenicity without an anticoagulant therapy such as heparin administration."

Other antithrombogenic methods and compositions are also well known. Thus, by way of further illustration, United States published patent application 20010016611 discloses an antithrombogenic composition comprising an ionic complex of ammonium salts and heparin or a heparin derivative, said ammonium salts each comprising four aliphatic alkyl groups bonded thereto, wherein an ammonium salt comprising four aliphatic alkyl groups having not less than 22 and not more than 26 carbon atoms in total is contained in an amount of not less than 5% and not more than 80% of the total ammonium salt by weight. The entire disclosure of this published patent application is hereby incorporated by reference into this specification.

Thus, e.g., U.S. Pat. No. 5,783,570 discloses an organic solvent-soluble mucopolysaccharide consisting of an ionic complex of at least one mucopolysaccharide (preferably heparin or heparin derivative) and a quaternary phosphonium, an antibacterial antithrombogenic composition comprising said organic solvent-soluble mucopolysaccharide and an antibacterial agent (preferably an inorganic antibacterial agent such as silver zeolite), and to a medical material comprising said organic solvent soluble mucopolysaccharide. The organic solvent-soluble mucopolysaccharide, and the antibacterial antithrombogenic composition and medical material containing same are said to easily impart antithrombogenicity and antibacterial property to a polymer to be a base material, which properties are maintained not only immediately after preparation of the material but also after long-term elution. The entire disclosrure of this United States patent is hereby incorporated by reference into this specification.

By way of further illustration, U.S. Pat. No. 5,049,393 discloses antithrombogenic compositions, methods for their production and products made therefrom. The anti-thrombogenic compositions comprise a powderized anti-thrombogenic material homogeneously present in a solidifiable matrix material. The anti-thrombogenic material is preferably carbon and more preferably graphite particles. The matrix material is a silicon polymer, a urethane polymer or an acrylic polymer. The entire disclosure of this United States patent is hereby incorporated by reference into this specification.

By way of yet further illustration, U.S. Pat. No. 5,013,717 discloses a leach resistant composition that includes a quaternary ammonium complex of heparin and a silicone. A method for applying a coating of the composition to a surface of a medical article is also disclosed in the patent. Medical articles having surfaces which are both lubricious and antithrombogenic, are produced in accordance with the method of the patent.

Referring again to FIG. 35, and in the preferred embodiment depicted therein, the sheath 4034 is non contiguous with the layer 4004; in this embodiment, another material 4036 (such as, e.g., air) is present. In FIG. 36, by comparison, the sheath 4034 is contiguous with the layer 4004.

In both of the embodiments depicted in FIGS. 35 and 36, the conductor 4000 preferably has a resistivity at 20 degrees Centigrade of from about 1 to about 100 micro ohm-centimeters.

In one embodiment, not shown, the sheath 4034 is omitted and the shield 4004 itself is comprised of and/or acts as an antithromgenenic composition. In one aspect of this embodiment, the outer surface of sheath 4034 is hydrophobic. In another aspect of this embodiment, the outer surface of the sheath is hydrophilic. Similarly, in the embodiments depicted in FIGS. 35 and 36, the outer surface 4037 of the sheath 4034 can be either hydrophobic or hyrophillic.

In this embodiment, the conductor assembly is comprised of a magnetic shield disposed above said flexible conductor, wherein said magnetic shield is comprised of an antithrombogenic composition, wherein said magnetic shield is comprised of a layer of magnetic shielding material, and wherein said layer of magnetic shielding material, when exposed to a magnetic field with an intensity of at least about 0.5 Teslas, has a magnetic shielding factor of at least about 0.5. The conductor (c) said conductor assembly has a heat shielding factor of at least about 0.2.

Although the invention has been shown and described with respect to a preferred embodiment thereof, it should be understood by those skilled in the art that various changes and omissions in the form and detail thereof may be made therein without departing from the spirit and scope of the invention.

We claim:

1. An implantable device comprised of a power source, means for generating electrical signals, means for communicating said electrical signals with biological matter in a biological organism, and a conductor assembly electrically connected to said biological matter, wherein:
   (a) said conductor assembly is comprised of a conductor that is capable of being flexed at least about 15 degrees and that has a resistivity at 20 degrees Centigrade of from about 1 to about 100 micro ohm-centimeters, (b) said conductor assembly is comprised of a magnetic shield disposed above said flexible conductor, wherein said magnetic shield is comprised of an antithrombogenic composition, wherein said magnetic shield is comprised of a layer of magnetic shielding material, and wherein said layer of magnetic shielding material, when exposed to a magnetic field with an intensity of at least about 0.5 Teslas, has a magnetic shielding factor of at least about 0.5; and (c) said conductor assembly has a heat shielding factor of at least about 0.2 when tested in accordance with A.S.T.M. standard test Standard Test F-2182-02.

2. The implantable device as recited in claim 1, wherein said implantable device is used to monitor and maintain at least one physiologic function.

3. The implantable device as recited in claim 2, wherein said device is comprised of means for generating electrical pulses for stimulating tissue in a biological organism electrically connected to said power source and a conductor assembly for transmitting said electrical pulses to said tissue.

4. The implantable device as recited in claim 1, wherein said conductor has a bend radius of less than 2 centimeters.

5. The implantable device as recited in claim 1, wherein said layer of magnetic shielding material is comprised of at least about 40 weight percent of nanomagnetic material with a mass density of at least about 0.01 grams per cubic centimeter, a saturation magnetization of from about 1 to about 36,000 Gauss, a coercive force of from about 0.01 to about 5,000 Oersteds, and relative magnetic permeability of from about 1 to about 500,000, and an average particle size of less than about 100 nanometers.

6. The implantable device as recited in claim 5, wherein said magnetic shield is comprised of from about 1 to about 99 weight percent of a material with an electrical resistivity of from about 1 microohm-centimeter to about $1 \times 10^{25}$ microohm centimeters, and wherein said conductor assembly is in the form of a cylinder.

7. The implantable device as recited in claim 6, wherein said layer of magnetic shielding material is comprised of at least 50 weight percent of said nanomagnetic material.

8. The implantable device as recited in claim 6, wherein said layer of magnetic shielding material is comprised of from about 40 to about 60 weight percent of a material comprised of particles with an elongated shape and an aspect ratio of at least about 10.

9. The implantable device as recited in claim 6, wherein said layer of magnetic shielding material is comprised of from about 40 to about 60 weight percent of a material comprised of a multiplicity of aligned fibers.

10. The implantable device as recited in claim 1, wherein said magnetic shield is contiguous with said conductor.

11. The implantable device as recited in claim 1, wherein said magnetic shield is comprised of an exterior surface with a Moh's hardness of from about 5 to about 15.

12. The implantable device as recited in claim 1, wherein magnetic shield is comprised of sheath disposed around said layer of magnetic shielding material.

13. The implantable device as recited in claim 1, wherein said magnetic shield is comprised of a material with a dielectric constant of from about 1.1 to about 10.

14. The implantable deivce as recited in claim 1, wherein said magnetic shield is comprised of diamond-like carbon.

15. The implantable device as recited in claim 1, wherein said magnetic shield has a thickness of from about 100 nanometers to about 10 microns.

16. The implantable device as recited in claim 1, wherein said layer of magnetic shielding material, when exposed to a magnetic field with an intensity of at lest about 0.5 Tesla, has a magnetic shielding factor of at least about 0.9.

17. The implantable device as recited in claim 1, wherein said magnetic shield is comprised of an exterior surface that is hydrophobic.

18. The implantable device as recited in claim 1, wherein said magnetic shield is comprised of an exterior surface that is hydrophilic.

* * * * *